United States Patent          (10) Patent No.:     US 10,195,632 B1
Baumgartner et al.           (45) Date of Patent:         Feb. 5, 2019

(54) STRATIFICATION DETECTION AND AEROSOL DISTRIBUTION SYSTEM

(71) Applicants: Paul Baumgartner, Port St. Lucie, FL (US); Jonathan J. Ricciardi, Wausau, WI (US); Carl L. Ricciardi, Tomahawk, WI (US)

(72) Inventors: Paul Baumgartner, Port St. Lucie, FL (US); Jonathan J. Ricciardi, Wausau, WI (US); Carl L. Ricciardi, Tomahawk, WI (US)

( * ) Notice: Subject to any disclaimer, the term of this patent is extended or adjusted under 35 U.S.C. 154(b) by 0 days.

(21) Appl. No.: 15/725,749

(22) Filed: Oct. 5, 2017

Related U.S. Application Data

(60) Provisional application No. 62/404,884, filed on Oct. 6, 2016.

(51) Int. Cl.
| | |
|---|---|
| *A61L 9/14* | (2006.01) |
| *B05B 17/06* | (2006.01) |
| *A61L 9/03* | (2006.01) |
| *A61L 2/22* | (2006.01) |
| *G01K 7/02* | (2006.01) |

(52) U.S. Cl.
CPC ............ *B05B 17/0607* (2013.01); *A61L 2/22* (2013.01); *A61L 9/032* (2013.01); *A61L 9/14* (2013.01); *G01K 7/02* (2013.01); *A61L 2202/14* (2013.01); *A61L 2202/15* (2013.01)

(58) Field of Classification Search
CPC .......... A61L 2/22; A61L 9/14; A61L 2202/14; A61L 2202/15; A61L 2202/25
See application file for complete search history.

(56) References Cited

U.S. PATENT DOCUMENTS

| | | |
|---|---|---|
| 3,561,444 A | 2/1971 | Boucher |
| 4,366,125 A | 12/1982 | Kodera et al. |
| 5,878,355 A | 3/1999 | Berg et al. |
| 5,925,966 A | 7/1999 | Riftin et al. |
| 6,102,992 A | 8/2000 | Berg et al. |
| 7,641,130 B2 | 1/2010 | Ricciardi et al. |
| 7,871,016 B2 | 1/2011 | Ricciardi et al. |
| 8,196,604 B1 | 6/2012 | Ricciardi et al. |
| 8,359,984 B1 | 1/2013 | Wolf, II et al. |
| 8,382,008 B1 | 2/2013 | Riccardi et al. |
| 9,551,996 B2 | 1/2017 | Baumgartner et al. |

(Continued)

*Primary Examiner* — Timothy C Cleveland
(74) *Attorney, Agent, or Firm* — Donald J. Ersler

(57) ABSTRACT

An improved apparatus and methods are presented for a new and improved ultrasonic aerosol generation apparatus and air/gas and deployed aerosol movement system, which is able to increase and improve the reliability and quality of coverage and treatment of the various targeted surfaces within an enclosed space, with the generated and deployed disinfecting aerosol, by providing an improved system to detect one or more of any layers and stratifications of gas(s) and deployed aerosols within the atmosphere of the treated area(s) at any time, and a means to remove and effectively disrupt, the said layers, so the deployed aerosol can effectively treat the targeted area(s), as well as additional enhancements to the systems used for processing the atmosphere in the targeted area(s) after the treatment cycle has completed deploying the aerosol, such as improving the cleaning of the dehumidification device, and the effective operation of the dehumidification and filter components.

21 Claims, 23 Drawing Sheets

(56) References Cited

U.S. PATENT DOCUMENTS

2008/0038166 A1* 2/2008 Hill .................. A61L 2/208
                                                      422/292
2011/0114744 A1* 5/2011 Ricciardi ............ A61L 2/22
                                                      239/4

* cited by examiner

STRATIFICATION DETECTION AND AEROSOL DISTRIBUTION SYSTEM

CROSS-REFERENCES TO RELATED APPLICATIONS

This is a non-provisional application, which claims the benefit of provisional application No. 62/404,884 filed on Oct. 6, 2016.

BACKGROUND OF THE INVENTION

1. Technical Field of the Invention

The present invention relates generally to further improved apparatuses and methods for the generation, and application, of an ultrasonically generated aerosol for uses including but not limited to the sanitization, detoxification, disinfection, high-level disinfection, and/or sterilization, of one or more areas and the surfaces in those areas, as well as the delivery of other types of liquid agents, for various purposes, to one or more areas, and without limitation, the surfaces in those area(s). The present invention includes, but it is not limited to, a new and improved ultrasonic aerosol generation apparatus and air/gas(s) and deployed aerosol movement system, that is able to increase and improve the reliability and quality of the coverage and treatment of the various targeted surfaces within the treated space(s), with the generated and deployed disinfecting aerosol.

2. Discussion of the Prior Art

The prior art has extensively taught that relatively quick disinfection and sterilization of surfaces can be achieved by exposing them to an aerosol of a disinfectant/sterilizing agent created by ultrasonic nebulization. The apparatus described in U.S. Pat. No. 4,366,125 (Kodera et al., 1980), which is incorporated herein by reference in its entirety, including any references cited therein, generates a hydrogen peroxide mist by an ultrasonic waves vibrator. The aqueous hydrogen peroxide is heated as it travels from a tank into a basin (col. 4, line 6-8) where it is turned into a fog or mist as the surface of the germicidal liquid in the basin is acted upon by ultrasonic waves. The fog or mist will adhere to the surface of materials being sterilized or disinfected. The surface is then irradiated with ultraviolet-ray lamps.

U.S. Pat. Nos. 5,878,355 and 6,102,992, each of which is incorporated herein by reference in its entirety, including any references cited therein, disclose a method and device for decontamination of a contaminated process area whereby a fine aerosol of an encapsulant is generated to encapsulate contaminants within a contaminated environment. The aerosol is generated by one or more ultrasonic transducers located below the surface of a reservoir containing a liquid. The output of the transducers is focused to either a point and/or directed toward an area near the surface of the liquid to cause a surface disturbance, which results in the formation of an aerosol from the liquid. The transducers used in these apparatuses are made from lead-zirconate-titanate-four (PZT-4) or other piezoelectric materials. This material is coated with a conductive coating (electrode material) that enables an electrical signal to energize the transducer and causes it to emit high frequency pressure (energy).

U.S. Pat. No. 7,641,130 to Ricciardi et al., discloses methods and apparatus for optimizing aerosol generation with ultrasonic transducers.

Accordingly, there is a clearly felt need in the art for an ultrasonic aerosol generation apparatus, which is able to generate greater volumes of disinfecting aerosol than that of the prior art. The present invention also combines the ability to generate and deploy larger amounts of small diameter aerosol, with a combination of apparatus parts that can constitute a smaller overall package, when compared with the prior art.

U.S. Pat. Nos. 3,561,444, 7,641,130, 7,871,016, 8,196,604, 8,359,984, 8,889,081 and 9,551,996, and U.S. patent application Ser. Nos. 13/277,750 and 14/247,893 are hereby incorporated into this patent application by reference in their entirety, including any references cited therein.

SUMMARY OF THE INVENTION

The present invention includes improved apparatuses and methods for the delivery and application, of an ultrasonically generated aerosol for uses including, but not limited to, the sanitization, disinfection, high-level disinfection, and/or sterilization, of one or more areas and the surfaces in those areas, as well as the delivery of other types of liquid agents, for various purposes, to one or more areas, and the surfaces found therein.

The present invention provides an ultrasonic aerosol generation apparatus and/or any other associated and/or independent apparatus(s), that are able to offer improvements to the current art including, but not limited to, (a) removing and/or effectively disrupting, at any time, at least one or more of any stratified layer(s) of air and/or gas(s), having one or more of any temperature(s), dew point, and/or humidity attributes(s), within the one or more area(s) targeted for deployment of the generated aerosol, (b) removing and/or effectively disrupting, at any time, at least one or more of any stratified layer(s) of the deployed aerosol, having one or more of any temperature(s), dew point, and/or humidity attribute(s), that can form in the targeted area(s) during the deployment of the aerosol from the aerosol generating apparatus, and (c) locating and using, at any time, one or more of any suitable temperature and/or humidity sensor(s) in the treated space(s) to identify one or more of any layer(s) and/or stratified layer(s) of air/gas(s) and/or deployed aerosol, having one or more of any temperature(s), dew points, and/or humidity attribute(s).

The present invention can also effectively, homogenize the distribution of, evenly distribute, effectively mix, and/or effectively distribute, the deployed aerosol within the targeted area(s) at one or more of any effective time(s) during the aerosol deployment cycle, as well as any other effective time during the entire treatment cycle for the targeted space(s), room(s), and/or area(s).

It is preferred, without limitation, that the aerosol is generated within the apparatus and administered into at least one targeted area(s) and/or onto targeted surfaces, by pressurized air or the movement of any air or gas to remove the generated aerosol from the aerosol generating apparatus. The aerosol that is produced, can be of any, sizes, mass concentration or density, and number concentration. It is preferred without limitation that the aerosol is a submicron droplet fog or aerosol of an anti-pathogen, toxin, fungal, sterilization, disinfection, or sporicidal agent(s) or mixtures thereof (herein collectively "Agent(s)"). However, any suitable liquid agent(s) may also be used in the present invention for various purposes such as, but not limited to, the delivery of any medication(s) to any part of any, plant, organism, animal, and/or human being.

According to an embodiment, and without limitation, the liquid that is aerosolized can be, but is not limited to one or more of any, chemical, compound, mixture, or substance, which is a liquid, preferably a solution, and may optionally include but is not limited to any, water, medicines, pharmaceutical or medical products, enzymes, fertilizers, pesticides, fuels, chemical neutralizers, and/or anti-pathogen/toxin/fungal/sporicidal agents, substances, combinations thereof, and the like.

According to a preferred embodiment, and without limitation, a preferred liquid is any suitable PAA or peroxyacetic acid, or any suitable hydrogen peroxide combined with any suitable peroxyacetic acid in an aqueous solution, which can be effective in sanitization, disinfection, high-level disinfection, and/or sterilization, and other applications, preferably approximately between 0.1-40% hydrogen peroxide combined with approximately 0.1-40% peroxyacetic acid in solution, more preferably approximately 0.88% hydrogen peroxide combined with approximately 0.18% peroxyacetic acid in an aqueous solution. Other liquids that may also be used include, but are not limited to, any chlorine dioxide in any solution and/or ozone in any solution.

Without limitation, the generated and deployed fog or aerosol can include any sized aerosol droplets, preferably including substantially of about ten micron to submicron or less sized aerosolized droplets. It is preferred, without limitation, that the aerosol has a higher rather than lower mass concentration or density of droplets. It is also preferred, without limitation, that the aerosol has a higher rather than lower number concentration of droplets.

The apparatus and methods described in the present invention can pertain to any ultrasonic aerosol producing apparatus. They can also pertain to any other aerosol producing apparatus. This apparatus, briefly described, has one or more piezoelectric transducers that are operated in parallel or series. The transducers are submerged in one or more of any suitable and effective tanks or reservoirs, and cause a surface disturbance, which results in the formation of an aerosol of the liquid in the tanks or reservoir(s).

According to an embodiment, and without being limited, one or more of any, ultrasonic aerosol generating apparatus, transducer, transducer design, transducer construction, transducer assembly, and means to hold or mount any transducer inside any tank or reservoir, may be used in the present invention. It is preferred, without limitation, that the transducers are bonded to any effective barrier material such as, but not limited to any glass. It is more preferred without limitation, that the transducer(s) are combined with a protective barrier, all in a manner disclosed in U.S. Pat. No. 7,641,130 (Ricciardi et al.).

The transducer(s) may be operated or driven with various combinations of power, watts, volts peak to peak, and/or frequencies, which result in the generation of an effective amount of aerosolized liquid output. It is preferred, without limitation, that at least an effective combination of attributes such as, but not limited to any, power, watts, volts peak to peak, and/or frequency, is utilized.

Examples of electronic equipment and methods for operating or driving the transducer(s) are discussed in U.S. Pat. Nos. 5,878,355 and 6,102,992 (both of which are incorporated herein by reference in their entirety, including any references cited therein). U.S. Pat. No. 5,925,966, which is incorporated herein by reference in its entirety, including any references cited therein, also provides details of the hardware necessary to operate the transducer(s). Additional electronic equipment, tolerances, and methods for operating or driving the transducer(s) known in the art may also be used. A variable frequency oscillator or signal generator is used to generate a high frequency wave, preferably a sine or square wave. According to an embodiment, and without limitation, a preferred oscillator is a digital function generator/counter capable of producing sine, square, triangle, pulse and ramp waves. A preferred oscillator has an adjustable frequency range from about 0.025 MHz to about 12 MHz, and may be set or designed for a particular need or requirement. It preferably, and without limitation, has variable output amplitude from 5 mV to 20 Vp-p (Volts peak to peak) being delivered to the amplifier, variable symmetry/duty cycle from 5% to 95% in the ramp or pulse mode, continuous or externally controlled outputs. This signal can then be optionally amplified using a power amplifier to increase the power to the optimum aerosol producing power. The volts peak to peak is a measure of power that is supplied to the transducer(s). A direct current (D.C.) offset between −10 v to +10 v can be added to any of the output waveforms.

In one embodiment, and without being limited, the amplifier is a solid-state amplifier that provides up to 2500 watts of linear power with low harmonic and intermodulation distortion and peak to peak voltages of about 20 volts to about 300 volts; however the number of watts could also be increased in order to provide enough power to drive a desired number of transducers and the peak to peak voltages could also be increased, preferably approximately at least about 100 watts of linear power per transducer(s) with about 190 to about 230 Vp-p.

The amplified signal from the amplifier is used to operate or drive one or a plurality of transducer(s), where in an embodiment each transducer(s) is operated at a frequency range between about 0.025 MHz to about 10 MHz or higher, preferably between about 0.5 MHz to about 2.5 MHz, more preferably between about 1.2 MHz and about 2.2 MHz. Moreover, in such an embodiment each transducer(s) has a resonant frequency between about 0.025 and about 10.0 MHz or higher. The operating frequency is the frequency at which the transducer(s) is being driven or operated.

One or more transducers are located in at least one tank or reservoir. It is preferred, without limitation, that at least one transducer is located in each tank or reservoir. It is more preferred, without limitation, that two transducers are located in each tank or reservoir. Without limitation, the output of the transducer(s) may be focused and/or directed to a point and/or any area or location near and/or at the surface of the liquid in a reservoir to cause a surface disturbance, which results in the formation of an aerosol of the liquid in the reservoir. Without being limited, the aerosol can then be blown or otherwise moved with pressurized air/gas(s) out of the tank or reservoir(s), and into one or more targeted areas or chambers.

Without being limited, at least one microprocessor based controller is preferably used to monitor, communicate with, and/or power, various components of the aerosol generating apparatus, including, but not limited to, the components described in the following description. Without limitation, the liquid is heated by one or more of any suitable heater element(s), preferably and without limitation in the reservoir(s) or chamber(s) where the one or more of any transducers are located, to a temperature at least above 80° F., preferably between 90° F.-150° F., and more preferable between about 110° degree F.-130° degree F. The temperature of the liquid is preferably, and without limitation, measured with one or more of any suitable thermocouple(s) or liquid temperature sensing device(s) located at any effective location(s) within the transducer chamber. The at least one transducer is preferably, and without limitation, powered by at least one of any suitable transducer power supply, all in a manner known to those skilled in the art. An aerosol is generated by ultrasonic vibration of the piezoelectric transducer. Any suitable air/gas can be blown, pumped, and/or flowed, into locations such as, but not limited to any, one or more of any reservoir(s) or chamber(s) where the one or more of any transducers are located, and where the generated aerosol is then moved or flowed out of the aerosol generating apparatus and into the one or more treated space(s), room(s), and/or targeted area(s). It is preferred, without limitation, that at least one of any effective blower(s) or fan(s) is effectively connected to the one or more of any suitable reservoir(s) or transducer chamber(s) where the one or more of any transducers are located, to supply the air/gas that removes the generated aerosol from the aerosol generating apparatus. Without being limited, the at least one microprocessor based controller can also communicate with and/or control the one or more of any: (a) downward facing fan(s), (b) temperature sensor(s), (c) dew point sensor(s), (d) relative humidity sensor(s), (e) fan(s) or blower(s) that move any air/gas(s) through any filter(s), and (f) dehumidification system(s) and/or apparatus(s).

It was found that in certain circumstances, the aerosol that is ultrasonically generated and deployed into the treated space(s), room(s), and/or targeted area(s), can stratify or form one or more of any layer(s) and/or formation(s) (Herein called "Layer(s)"), and the deployed aerosol can also take significantly longer to effectively fill the treated space(s), room(s), and/or targeted area(s), as it stratifies. It is plausible that this could also happen with non-ultrasonic aerosol generators as well. Without being limited, this can be observed in circumstances, or combination of one or more conditions, such as, but not limited to, when the treated space(s), room(s), and/or targeted area(s) have an atmosphere that is: any temperature or temperature range that is considered warm and/or above ambient temperature, any temperature or temperature range that is considered hot and/or significantly above ambient temperature, any humidity range that is considered dry and/or below ambient humidity levels. Also without being limited, this is especially found in times like the winter months, when the atmosphere in the targeted space(s), area(s), or treated room(s), is heated, such as, but not limited to the inside of any hospital patient room in the winter.

Without being limited, testing has indicated that this layering or stratification phenomena can be observed when one or more, or combination of, various variables are present such as, but not limited to: (a) the treated space(s), room(s), and/or targeted area(s) have a relative humidity value below 60%, (b) limited air movement or air flow is observed within the treated space(s), room(s), and/or targeted area(s), (c) the treated space(s), room(s), and/or targeted area(s) have a temperature that is higher than 50 degree Fahrenheit, and/or (d) the treated space(s), room(s), and/or targeted area(s) have experienced a recent inrush of heated air.

More particularity, and without limitation, one or more of any "warmer" and/or "drier" pockets and/or layers of air or gas(s) can also rise to one or more location(s) such as, but not limited to any, upper region(s) or location(s) of the treated space(s), room(s), and/or targeted area(s), making it difficult for the deployed aerosol to quickly disperse and/or move through, into, and/or within these region(s) or location(s), and contact all of the surfaces in the targeted area(s) such as, but not limited to any ceiling surfaces and/or any other surfaces near any ceiling(s).

Without limitation, the one or more layers of deployed aerosol that can form, can be any thickness or depth, can form at one or more of any height(s) and/or distance(s) from the floor, and can form at one or more of any location(s), within the treated space(s), room(s), and/or targeted area(s). Without being limited, this layering or stratification of the deployed aerosol can be evident in one or more ways such as, but not limited to, the deployed aerosol in the treated space(s) can form at least one layer of any thickness or depth, at one or more of any heights, but typically at least one layer of deployed aerosol that is present between about three inches to eight feet high measured from the floor.

Without limitation, the deployed ultrasonically generated aerosol can create any, thick, dense, and/or high concentration, cloud of aerosol, and the aerosol can fill the treated space(s), room(s), and/or targeted area(s) in various ways including, but not limited to: (a) from the floor(s) of the treated space(s), room(s), and/or targeted area(s) to the ceiling(s) of the treated space(s), room(s), and/or targeted area(s), (b) from the ceiling(s) of the treated space(s), room(s), and/or targeted area(s) to the floor(s) of the treated space(s), room(s), and/or targeted area(s), and (c) in a homogeneous and uniform dispersion of deployed aerosol within the treated space(s), room(s), and/or targeted area(s). It is preferred, without limitation, that the ultrasonically generated aerosol deployed by the aerosol generating apparatus in the present invention, at least fills the treated space(s), room(s), and/or targeted area(s) from the floor to the ceiling, and more preferably an even fill, homogeneous distribution, and/or equal distribution, of the deployed aerosol within the targeted area(s). Also, and without limitation, the generated aerosol can have any visual consistency, concentration, and/or density. It is preferred without limitation, that the aerosol generating apparatus in the present invention, creates and deploys an aerosol that at least has an effective concentration and density. It is more preferred, without limitation, that the aerosol that is deployed by the aerosol generating apparatus, fills the treated space(s), room(s), and/or targeted area(s) with aerosol until the room becomes opaque to light, almost opaque to light, and/or thickly clouded to a point where it is impossible or at least difficult to see across the treated space(s), room(s), and/or targeted area(s).

Without being limited, the lack of a homogeneous dispersion of the deployed aerosol within the treated space(s), room(s), and/or targeted area(s), and more specifically the presence of one or more layer(s) of the deployed aerosol or stratified layers of the deployed aerosol, within the treated space(s), room(s), and/or targeted area(s), can be detected by ways including, but not limited to, measuring the temperature(s) and/or humidity(s) at more than one locations within the treated room(s) and/or targeted area(s).

The layering or stratification of the deployed aerosol will typically self correct and disappear, if an effective amount of time is able to elapse and/or an effective amount of aerosol is deployed within an effective amount of time, as the aerosol slowly moves within the treated area(s) and overcomes the stratification or layers of aerosol and/or air, and a homogeneous or equal dispersion of the aerosol is finally observed. Unfortunately, many industries such as, but not limited to, the healthcare industry, are pressured to continuously reduce costs, and treatment times for high-level disinfection technologies like that described in the present invention, are connected with facility costs. Therefore, a need exists to quickly eliminate any layers or stratification of any, air, gas(s), and/or aerosol(s), before, during, and/or after, the deployment of any aerosol(s) into the treated space(s), room(s), and/or targeted area(s), and/or during any other parts of the decontamination process for a given space.

Within the prior art, various large-area disinfection technology companies have used one or more blower(s) or fan(s) to move vaporized hydrogen peroxide vapors throughout the treated room(s) and/or targeted area(s). The fans have been reported to point their output either horizontally and/or towards the ceiling, sometimes even moving substances such as the various gas(s) and/or aerosol(s), between various interconnected room(s) or space(s).

However, and without limitation, using the fan(s) and blower(s) to move any generated and deployed aerosol(s) and/or the deployed vaporized hydrogen peroxide vapors, either horizontally and/or pointing toward the ceiling of the treated room(s), can present various problems using aerosol generator(s) such as, but not limited to, the ultrasonic aerosol generating apparatus as described in the current invention. One problem, and without limitation, is that the deployed ultrasonically generated aerosol can create a dense or very dense cloud of aerosol within the treated space(s), room(s), and/or targeted area(s), and moving it through one or more fan(s) or blower(s) can present problems that can adversely effect the deployed aerosol in the treated area(s) such as, but not limited to, (a) the aerosol droplets can coalesce into larger droplets while being moved in a steady stream of carrier air or gas(s), which is not desired for reasons known to those skilled in the art, (b) the aerosol droplets can impact the surfaces of the blower(s) or fan(s) thus removing the deployed aerosol from the atmosphere, (c) an ineffective or insufficient volume and/or amount of the deployed aerosol and/or the aerosol cloud that can form in the treated space(s), room(s), and/or targeted area(s) from the deployed aerosol, is moved by the fan(s) or blower(s) when the aerosol is present, especially as a layer or stratified layer of deployed aerosol that starts at and/or is located at, above, approximate to, and/or or near, the floor of the treated space(s), room(s), and/or targeted area(s), at any measured depth, thickness, and/or height from the floor, as the aerosol is moved primarily in one direction as a steady stream of carrier air or gas(s) intermixed with the aerosol from these fan(s) or blower(s).

Without being limited, the deployed aerosol in the one or more of any targeted area(s) can be moved by one or more of any fan(s), blower(s), air/gas pump(s), or any other effective means for moving air/gas(s), at any effective speed, velocity, and/or quantity, and for any effective length of time. More importantly, and without limitation, it has been observed that moving the deployed aerosol at any excessive velocity, and for one or more of any excessive period(s) of time, can cause the visible deployed aerosol, and/or the visible deployed aerosol cloud that can form in the treated space(s), room(s), and/or targeted area(s) at one or more of any locations and in any form(s) from the deployed aerosol, to disappear within the treated space(s), room(s), and/or targeted area(s). One potential theoretical reason for this visual observation, is that the rapidly moving aerosol droplets continuously bleed off and lose their atmospheres as they move, until the particle itself goes to vapor and disappears, or at least shrinks to a size that cannot be seen by the human eye.

The present invention is an improvement over the prior art by providing multiple enhancements for an improved deployed aerosol movement system. The present invention can also be used by any aerosol generating technology, apparatuses, and methods, known to those skilled in the art.

In the first embodiment of the present invention, an improved means for effectively, removing, mixing together with the other parts of the atmosphere within the targeted area(s) (30), diminishing, and/or disrupting, one or more of any layer(s) that may be present at any time(s) within the atmosphere of the treated space(s), room(s), and/or targeted area(s) such as, but not limited to any, one or more of any layer(s) of any air/gas(s) having one or more of any temperature(s) and/or humidity level(s) present within the targeted area(s), and/or one or more of any layer(s) of the deployed aerosol or stratified layers of the deployed aerosol, having one or more of any temperature(s) and/or humidity level(s), that can form within the treated space(s), room(s), and/or targeted area(s), is provided. This is accomplished by the use of one or more of any fan(s), blower(s), air pump(s), and/or any other effective means for moving any air/gas(s) and/or aerosol within the treated space(s), room(s), and/or targeted area(s), that are facing effectively downward toward the floor of the treated space(s), room(s), and/or targeted area(s) so that their output including, but not limited to any, air and/or gas(s), is also directed downward toward the floor of the treated room(s) and/or targeted area(s) (Herein called "Downward Facing Fan(s)").

Without being limited, one intention of using the downward facing fan(s) and/or blower(s), and without limitation, is to effectively and/or efficiently move an effective volume or mass of air/gas(s) and/or aerosol, within the treated space(s), room(s), and/or targeted area(s), with a velocity that is at least effective, and more preferably a velocity that can effectively, remove, mix together with the other parts of the atmosphere within the treated space(s), room(s), and/or targeted area(s), diminish, and/or disrupt, one or more of any layer(s) of any deployed aerosol and/or any layer(s) of any air/gas of one or more of any temperature(s) and/or humidity level(s), that may be present at any time(s) within the treated space(s), room(s), and/or targeted area(s), so that the deployed aerosol may, evenly disperse, completely distribute, evenly distribute, effectively mix together with the other parts of the atmosphere within the treated space(s), room(s), and/or targeted area(s), effectively distribute, completely disperse, and/or completely homogenize, within the treated space(s), room(s), and/or targeted area(s).

A second intention, and without being limited, of using the downward facing fan(s) and/or blower(s), is to effectively and/or efficiently move an effective volume or mass of air/gas(s) and/or aerosol, within the treated space(s), room(s), and/or targeted area(s), in one or more of any effective directions, and preferably in multiple effective directions, that can effectively, remove, mix together with the other parts of the atmosphere within the treated space(s), room(s), and/or targeted area(s), diminish, and/or disrupt, one or more of any layer(s) of deployed aerosol and/or any layer(s) of air/gas of one or more of any temperature(s) and/or humidity level(s), that may be present at any time(s) within the treated space(s), room(s), and/or targeted area(s), so that the deployed aerosol may evenly disperse, completely distribute, evenly distribute, effectively distribute, completely disperse, and/or completely homogenize, within the treated space(s), room(s), and/or targeted area(s). It is preferred, without limitation, that the air/gas flow that flows out of the downward facing fan(s) impacts the floor and spreads in more than one direction, and preferably a plurality of directions, and more preferably in a 360 degree distribution.

A third intention, of using the downward facing fan(s) and/or blower(s), and without limitation, is to effectively and/or efficiently move an effective volume or mass of air/gas(s) and/or aerosol, within the treated space(s), room(s), and/or targeted area(s), with a velocity and/or in direction(s) that will (a) not adversely or negatively effect or diminish the deployed aerosol's efficaciousness and effectiveness, (b) not adversely or negatively effect or diminish the size of the deployed aerosol so that it is not effective, (c) not cause the deployed aerosol and/or aerosol cloud in the targeted area(s), to diminish, experience a reduction in any opaque qualities, experience a reduction in any cloud qualities, and/or disappear, (d) eliminate and/or reduce the ability of the aerosol to effectively and/or evenly fill the treated space(s), room(s), and/or targeted area(s), and (e) eliminate and/or reduce the ability of the aerosol to effectively and/or evenly fill the treated space(s), room(s), and/or targeted area(s), and effectively and efficaciously treat the various surfaces in those space(s) or area(s).

A fourth intention, of using the downward facing fan(s) and/or blower(s), and without limitation, is to effectively and/or efficiently move, an effective volume or mass of air/gas(s) and deployed aerosol, so that it preferably moves gently and without, disrupting, reducing, and/or damaging the effectiveness and efficacious of the deployed aerosol, and/or cloud of deployed aerosol, that can be located above the floor in the treated space(s), room(s), and/or targeted area(s), from a lower or bottom area, location, and/or region, of the the treated space(s), room(s), and/or targeted area(s), to an upper or top top, area, location, and/or region, of the treated space(s), room(s), and/or targeted area(s).

In a second embodiment of the present invention, and without limitation, the downward facing fan(s) and/or blower(s) can be located at one or more of any effective locations within the treated space(s), room(s), and/or targeted area(s), as one or more independent device(s) or apparatus(s). Without being limited, the downward facing fan(s) and/or blower(s) can be controlled and operated in any manner known to those skilled in the art. It is preferred, without limitation, that these independently located downward facing fan(s) and/or blower(s) are battery powered and wireless controlled, however, they can also be controlled and powered through one or more of any suitable cables all in a manner known to those skilled in the art.

In a third embodiment of the present invention, and without limitation, one or more of any downward facing fan(s) can also be preferably located within the housing or skin of the aerosol generating apparatus. The housing or skin of the aerosol generating apparatus can also include one or more of any effectively sized and located vents, through which any air/gas(s) or atmosphere from within the treated space(s), room(s), and/or targeted area(s), can flow into the aerosol generating apparatus, into and through the downward facing fan(s), and then back into the treated space(s), room(s), and/or targeted area(s). It is preferred, without limitation that the air/gas(s) or atmosphere from within the treated space(s), room(s), and/or targeted area(s) is effectively filtered before it enters, as it enters, and/or as it moves through, the aerosol generating apparatus and out of any downward facing fan(s) and/or dehumidification system or apparatus.

In a fourth embodiment of the present invention, and without limitation, any part or portion of any output from one or more of any dehumidification apparatus(s) can also be channeled, moved, and/or ducted, to and/or flow through and out of, the one or more of any downward facing fan(s). It is preferred, without limitation, that the one or more of any dehumidification apparatus(s) is located within the housing or skin of the aerosol generating apparatus. However, the dehumidification apparatus(s) can also be any independent or stand-alone apparatus(s) that can operate together with the one or more downward facing fan(s). It is also preferred, without limitation, that the air/gas(s) flow that leaves the dehumidification apparatus(s) is initially captured within the housing or skin of the aerosol generating apparatus, but is then moved out from within the skin or housing of the aerosol generating apparatus through the operation of the one or more of any downward facing fan(s), that are preferably separate from the dehumidification system. The output or airflow from the dehumidification apparatus(s) can be flowed to and through the downward facing fan(s) at any times, and preferably at least at one or more of any effective time(s), and more preferably during the dehumidification stage or step of the treatment of the one or more of any treated space(s), room(s), and/or targeted area(s). Without being limited, this can provide advantages such as, but not limited to, using the warm or hot dehumidified air to help dry any wet floor(s) within the treated space(s), room(s), and/or targeted area(s) after the aerosol has been deployed into the treated space(s), room(s), and/or targeted area(s). Also without being limited, this can provide advantages such as, but not limited to, decreasing the amount of time to effectively dry one or more surfaces within the treated room(s) and/or targeted area(s).

In a fifth embodiment of the present invention, and without limitation, an improved means for sensing the presence, absence, and/or removal, of the one or more of any layer(s) that may be present at any time(s) within the atmosphere of the treated space(s), room(s), and/or targeted area(s) such as, but not limited to any, one or more of any layer(s) of any air/gas(s) having one or more of any temperature(s) and/or relative humidity(s), and/or one or more of any layer(s) of the deployed aerosol or stratified layers of the deployed aerosol, that can also form within the atmosphere of the treated space(s), room(s), and/or targeted area(s), having one or more of any temperature(s) and/or relative humidity(s), can be used in the present invention.

Without being limited, the improved means for sensing the presence, absence, and/or removal, of these various layer(s) can include, but is not limited to, locating one or more of any temperature sensor(s), dew point sensor(s), and/or humidity, sensor(s), within the treated space(s), room(s), and/or targeted area(s). It is preferred, without limitation, that these various sensor(s) are at least located in one or more of any effective location(s). It is more preferred, without limitation, that the temperature, dew point, and/or humidity, sensor(s), are not only located at more than one different and effective locations within the treated space(s), room(s), and/or targeted area(s), but they are also located at various effective distances measured from the floor and/or ceiling within the treated space(s), room(s), and/or targeted area(s). Without being limited, these various temperature, dew point, and/or humidity sensors, can indicate the presence and/or absence of the one or more of any layer(s) of the deployed aerosol or stratified layers of the deployed aerosol, within the treated space(s), room(s), and/or targeted area(s), in ways such as, but not limited to, (a) showing or reporting one or more difference(s) in the temperature, dew point, and/or relative humidity, data within more than one locations within the treated space(s), room(s), and/or targeted area(s) indicating the presence of one or more of any layer(s) within these area(s), (b) showing or reporting identical or similar temperature, dew point, and/or relative humidity, data within more than one locations within the treated space(s), room(s), and/or targeted area(s) indicating the absence of one or more of any layer(s) within these area(s) and a uniform or homogeneous dispersion of deployed aerosol.

For example, and without limitation, an even or homogeneous distribution or dispersion of the deployed aerosol within the atmosphere of the treated space(s), room(s), and/or targeted area(s), is typically indicated by temperature and/or humidity data such as, but not limited to, data that is close to being the same, data that is similar, data that is about the same, data that is almost identical, and data that is the same.

In another example, and without limitation, the presence of the one or more of any layer(s) that may be present at any time(s) within the atmosphere of the treated space(s), room(s), and/or targeted area(s) such as, but not limited to any, one or more layer(s) of any air/gas(s) having one or more of any temperature(s) and/or relative humidity, and/or one or more of any layer(s) of the deployed aerosol or stratified layers of the deployed aerosol, that can also form within the treated space(s), room(s), and/or targeted area(s), is typically indicated by temperature and/or humidity data such as, but not limited to, data that is different and/or significantly different.

Accordingly, it is an object of the present invention to provide an improved deployed aerosol movement system, which is able to detect the presence and/or removal or absence of the one or more of any layer(s) that may be present at any time(s) within the treated space(s), room(s), and/or targeted area(s) such as, but not limited to any, one or more airborne layer(s) of any air/gas(s) having one or more of any temperature(s) and/or relative humidity, present within the targeted area(s), and/or one or more airborne layer(s) of the deployed aerosol or stratified layers of the deployed aerosol, that can also form within the treated space(s), room(s), and/or targeted area(s).

Accordingly, it is also an object of the present invention to provide an improved deployed aerosol movement system, which can effectively, remove, mix together with the other parts of the atmosphere within the treated space(s), room(s), and/or targeted area(s), diminish, and/or disrupt, one or more of any layer(s) of deployed aerosol and/or layer(s) of air/gas of one or more of any temperature(s), that may be present at any time(s) anywhere within the treated space(s), room(s), and/or targeted area(s), by using one or more downward facing fan(s), so that the deployed aerosol may evenly disperse, evenly and effectively distribute, completely distribute, effectively mix together with the other parts of the atmosphere within the treated space(s), room(s), and/or targeted area(s), completely disperse, and/or completely homogenize, within the treated space(s), room(s), and/or targeted area(s).

It is a further object of the present invention to provide an improved deployed aerosol movement system, that is enhanced by flowing the air/gas(s) output from a dehumidification system to and through one or more of any downward facing fans for advantages such as, but not limited to, assisting in the drying of various surface(s) within the treated space(s), room(s), and/or targeted area(s).

These and additional objects, advantages, features and benefits of the present invention will become apparent from the following specification.

DETAILED DESCRIPTION OF THE PREFERRED EMBODIMENTS

The present invention includes apparatuses and methods related to a new and improved ultrasonic aerosol generation apparatus and air/gas(s) and deployed aerosol movement system, that is able to increase and improve the reliability and quality of the coverage and treatment of the various targeted surfaces within the treated space(s), with the generated and deployed disinfecting aerosol, more particularity, and without limitation, an aerosol (40) of liquid (45) that is created with ultrasound or piezoelectric transducers (10), for a wide range of uses including but not limited to: (a) the sanitization, disinfection, high-level disinfection, or sterilization of one or more areas and the surfaces in those areas, (b) the delivery of other types of liquid (45) in the form of an aerosol (40) for various purposes, such as, but not limited to, the application of pesticides, fungicides, moisture, fuel, chemical neutralizers, medication, fertilizer, and/or any other suitable particles, to one or more areas and surfaces within those area(s). The attributes of the one or more of any: targeted area(s), targeted space(s), treated space(s), sealed and treated space(s), treated area(s), sealed and treated room(s), targeted room(s), treated room(s), room(s), area(s), and/or space(s) (Herein called "Targeted Area(s)") (30), to which the aerosol (40) is delivered or applied, can vary and can include, but is not limited to any: spaces that are open, enclosed, semi-enclosed, unsealed, sealed, or partially sealed. It is preferred, without limitation, that the area in which the aerosol (40) is administered in the present invention is enclosed and effectively sealed to prevent the leakage of the aerosol (40) from the enclosed and/or treated area(s) or targeted area(s) (30).

Referring initially to FIGS. 1-8, any suitable aerosol generating machine and/or the aerosol generating apparatus (1), can be operated either outside, partially inside and partially outside, or within, any area in which the aerosol (40) is deployed or administered. It is preferred, without limitation, that the aerosol generating apparatus (1) is any suitable ultrasonic aerosol generating apparatus (1), and more preferably any suitable ultrasonic aerosol generating apparatus (1) as described in the present invention. It is preferred, without limitation, that the aerosol generating apparatus (1) is operated inside the targeted area(s) (30).

Figure 1:
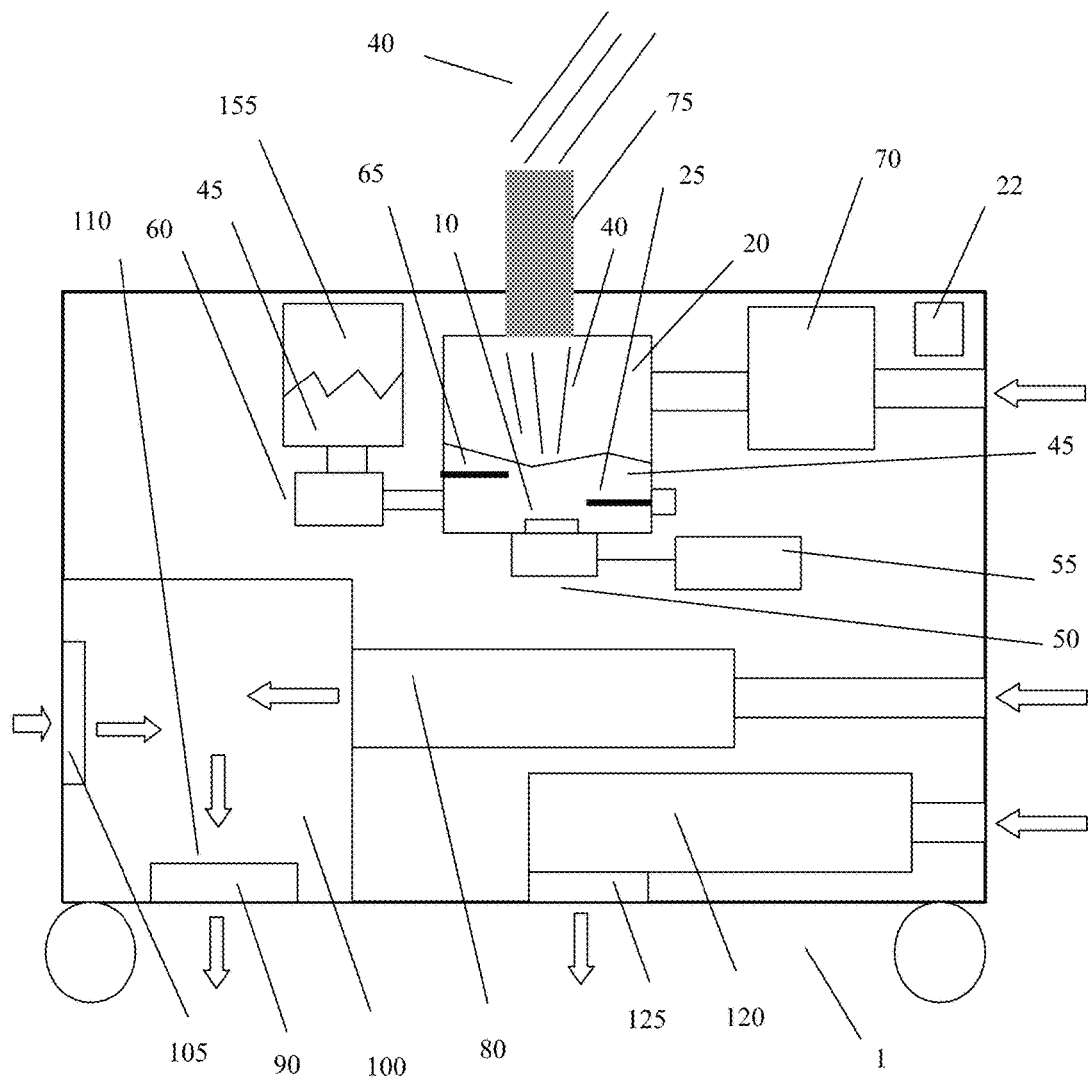
FIG. 1 is a cross sectional view of an ultrasonic aerosol generator apparatus including a dehumidification apparatus, a common intake compartment, downward facing fans, charcoal or carbon filter, and microprocessor control.
Figure 1A:
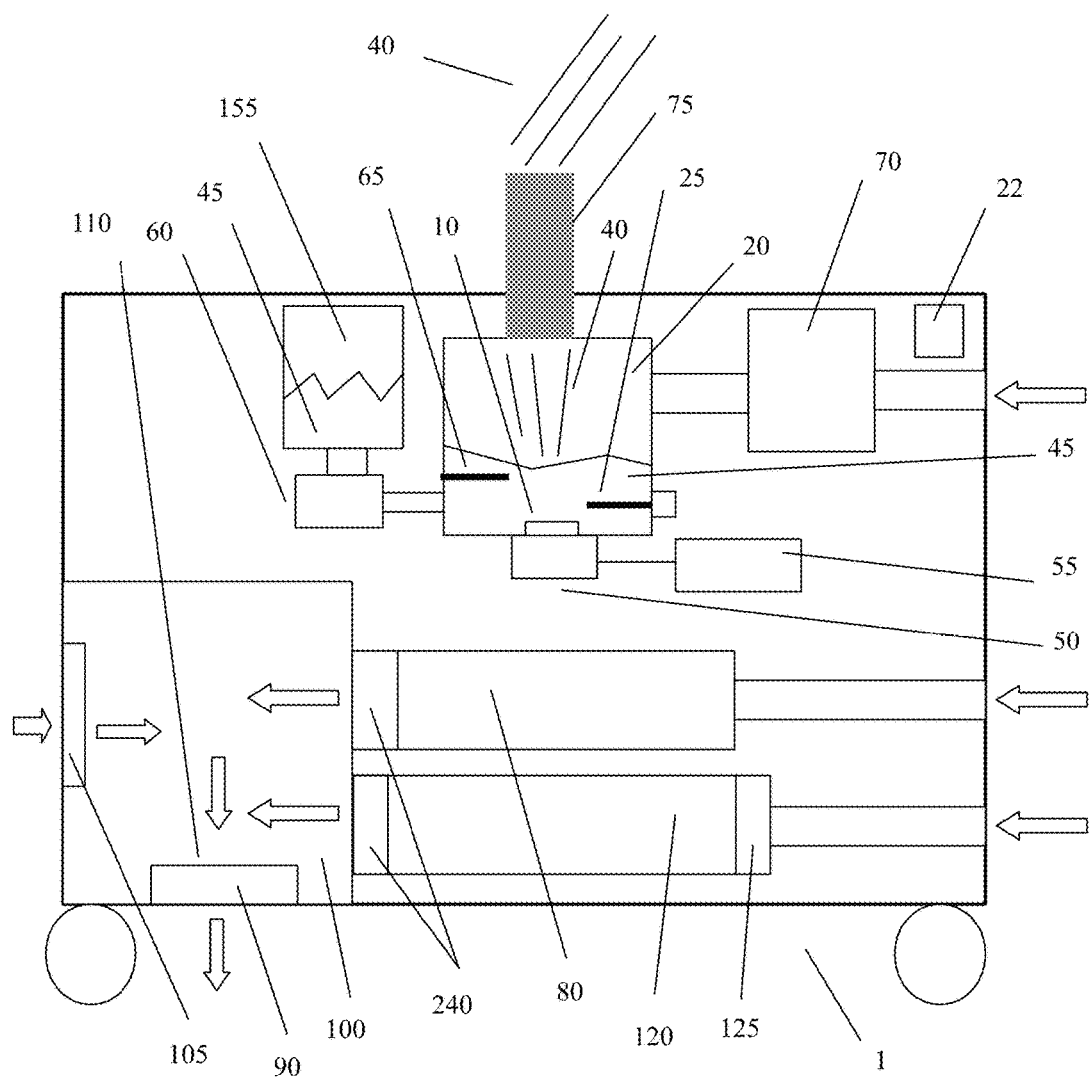
FIG. 1a is a cross sectional view of an ultrasonic aerosol generator apparatus including a dehumidification apparatus, a common intake compartment, sideward facing fans, charcoal or carbon filter, and microprocessor control.
Figure 2:
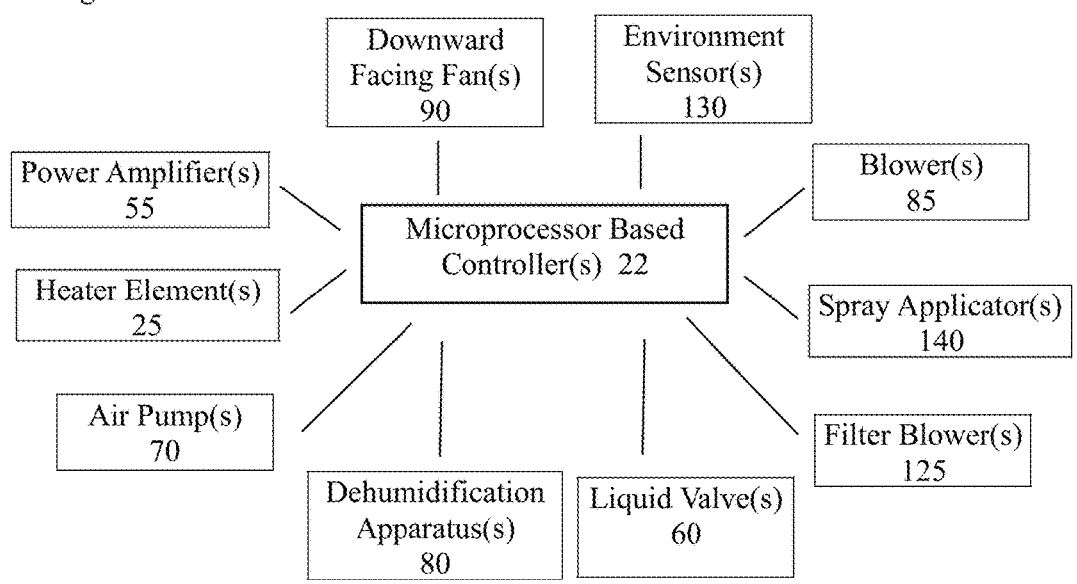
FIG. 2 is a block diagram illustrating communication and power components of an ultrasonic aerosol generating apparatus.
Figure 3:
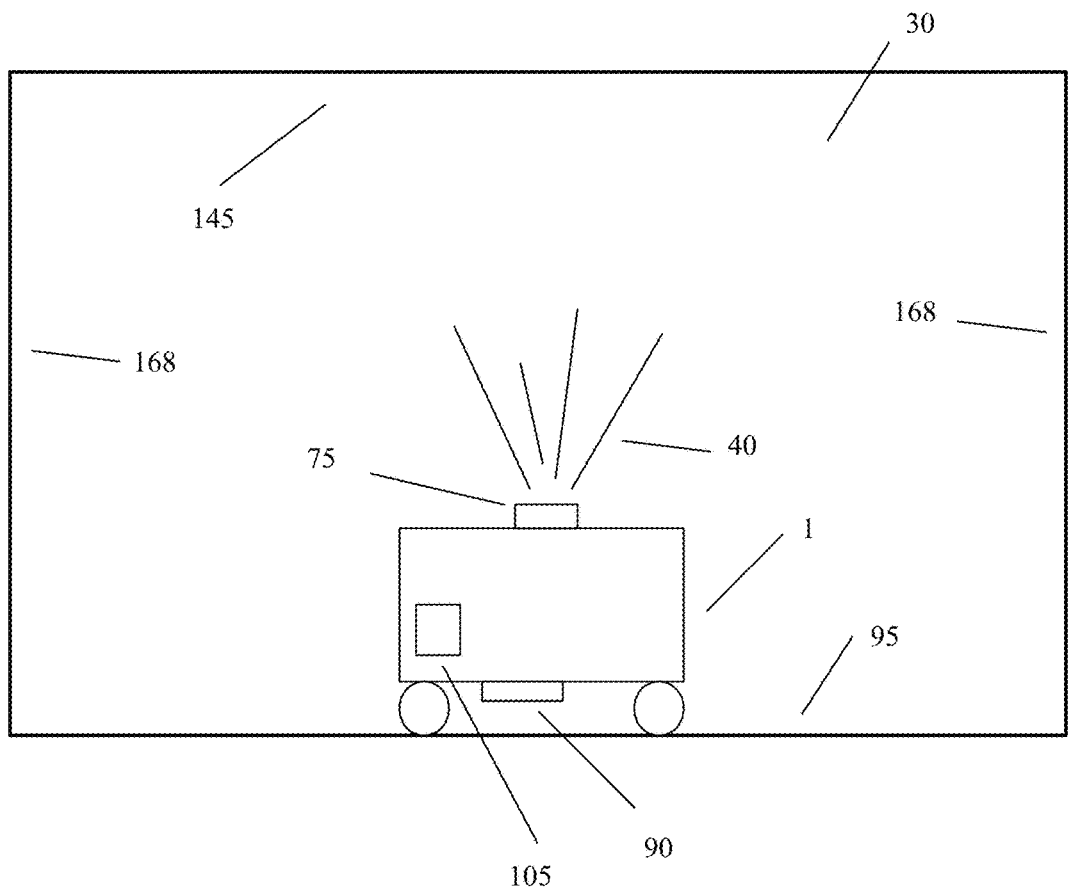
FIG. 3 is a front view of an ultrasonic aerosol generator positioned in an enclosure or room.

With reference now to the drawings, and particularly to FIG. 1, there is shown a perspective view of an aerosol generation apparatus (1). With reference to FIGS. 1,3,4, and FIGS. 6-8, and without limitation, the aerosol generation apparatus (1) preferably includes at least one transducer chamber (20) that can hold any effective volume and depth of the liquid (45) to be generated into an aerosol (40) by the one or more of any effective transducer(s) (10), all in a manner known to those skilled in the art. Without being limited, the one or more transducer(s) (10) may be located, coupled, mounted on and/or in, at any effective locations with one or more of any suitable and effective transducer holding, sealing, housing, and/or mounting device(s) or assembly(s) (Herein called "Transducer Mounting Assembly) (50), all in a manner known to those skilled in the art.

According to an embodiment, and without limitation, it is preferred that the transducer(s) (10) used in the present invention, are at least similar in form, function, and assembly with various parts, to those described in U.S. Pat. No. 7,641,130 and the face of the transducer(s) can be protected by any suitable and effective barrier(s).

Without being limited, a power amplifier (55) supplies the at least one ultrasonic transducer (10) with electrical power. Any suitable transducer (10), transducer design, assembly of transducer related parts, and transducer housing(s) and/or mounting fixture(s), may be used in the present invention. Also without being limited, the transducer(s) (10) can be made of any suitable piezoelectric material, preferably a lead-zirconate-titanate (PZT) material, and more preferably lead-zirconate-titanate-four (PZT-4). It is also preferred, without limitation, that the transducer(s) (10) is coated with any suitable conductive coating (not shown) that enables an electrical signal to energize or drive the transducer(s) (10) causing it to emit any pressure and/or energy of any desired character.

Without limitation, the power amplifier (55) can also include one or more of any suitable oscillator or powered oscillator. Without being limited, it is preferable to supply the ultrasonic transducer (10) with at least any suitable voltage and wattage, and more preferably and without limitation, any voltage between 20 to 300 volts peak to peak and wattage between 1 to 600 watts. Without limitation, the one or more transducer(s) (10), can be operated at any suitable and effective frequency, preferably at a frequency range between about 0.025 MHz to about 10 MHz or higher, more preferably between about 0.5 MHz to about 2.5 MHz, and even more preferably between about 1.2 MHz and about 2.2 MHz.

The at least one microprocessor based controller (22) is preferably used to monitor, power, and/or control, various components, such as, but not limited to, those described in the following description and in the present invention. The transducer chamber (20) is preferably filled with liquid (45) through at least one of any suitable liquid valve (60). The liquid (45) is preferably gravity fed to the liquid valve (60) from any suitable supply tank or reservoir (155). Without limitation, at least one of any effective heater element(s) or any other effective means for heating liquid (Herein called "Heater Element") (25), can be located in one or more of any effective location(s) within the transducer chamber (20). Also, without being limited, the liquid (45) is at least heated at any suitable location within the transducer chamber (20) by the at least one of any effective heater element(s) (25) to a preferable temperature of at least above 80 degree F., a more preferable temperature between 90° F.-150° F., and very preferable about 110° degree F., but any other effective temperature(s) may also be used at any times. The temperature of the heated liquid (45) in the transducer chamber (20), is measured with at least one of any suitable temperature sensor such as, but not limited to any, thermocouple (65). The at least one ultrasonic transducer (10) is at least powered by any effective power amplifier (55). An aerosol (40) is generated by vibration and/or or any effective activation of the ultrasonic transducer(s) (10) forming an aerosol (40) from the liquid (45) above the transducer(s) (10) that is supplied in the at least one transducer chamber(s) (20). Air/gas is pumped or flowed into the transducer chamber (20) via one or more of any effective, fan(s), blower(s), or any other effective means to move air/gas (Herein called "Air Pump(s)") (70). It is preferred, without limitation, that the one or more air pump(s) (70) are effectively connected to the one or more transducer chamber(s) (20). It is also preferred, without limitation, that the air pump(s) (70) are able to effectively flow or move air/gas(s) or the atmospheric gas(s) from within the treated room(s) and/or targeted area(s) (30) into and through the one or more transducer chamber(s) (20). The air/gas pumped or flowed into the transducer chamber (20) pushes or otherwise moves or flows the aerosol (40) generated by the vibration of the at least one ultrasonic transducer(s) (10) through the at least one outlet pipe (75), and into the treated room(s) and/or targeted area(s) (30) where the aerosol (40) is deployed.

Figure 4:
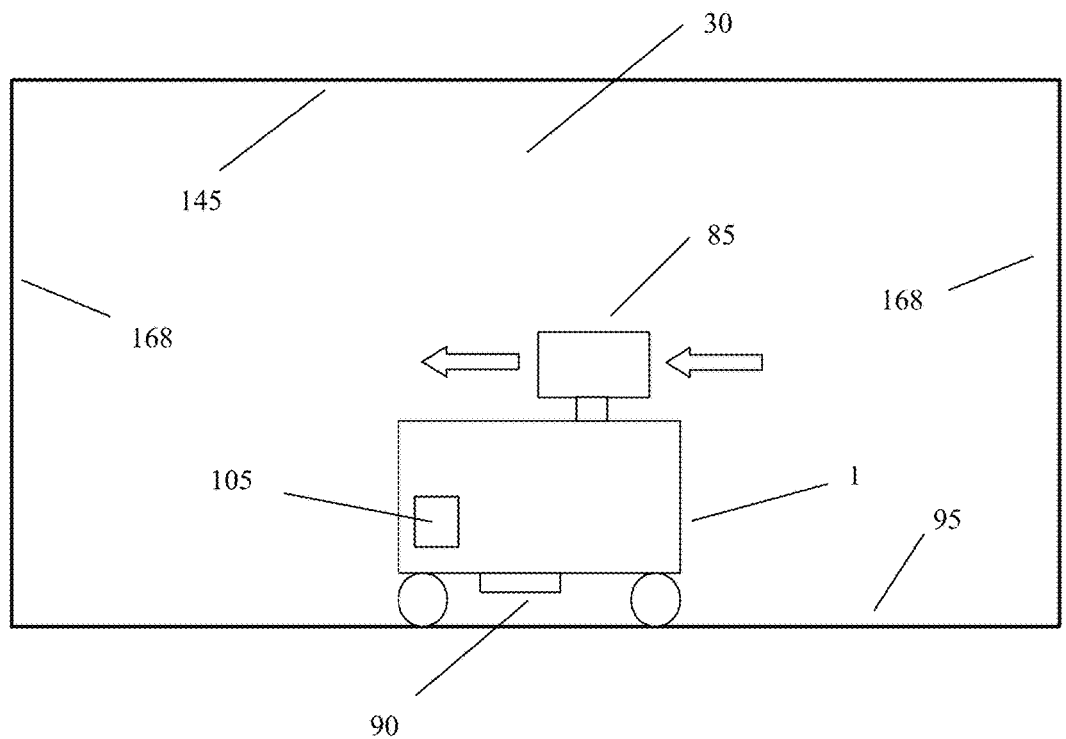
FIG. 4 is a front view of an ultrasonic aerosol generator positioned in an enclosure or room with at least one fan or blower having a horizontal output mounted to a top thereof.

With reference to FIG. 4 and according to an embodiment, and without limitation, one or more of any fan(s), blower(s), pump(s), and/or any other means (Herein after called "Blower(s)") (85), for effectively moving any air/gas(s) and/or aerosol(s) (40) anywhere within the treated room(s) and/or targeted area(s) (30), can be a part of any aerosol generating apparatus (1) design. It is preferred, without limitation, that the blower(s) (85) are at least effective. Without being limited, any of the one or more blower(s) (85) can be operated independently and/or at the same time as any of the one or more downward facing fan(s) (90). However, it is preferred, without limitation, that only the one or more of any downward facing fan(s) are operated.

Without being limited, the one or more of any blower(s) (85) can be effectively and suitable mounted to one or more of any suitable and effective location(s) within the aerosol generating apparatus (1), and/or to or on one or more of any suitable and effective exterior location(s) of the aerosol generating apparatus (1). Also, and without limitation, the output or air/gas(s) flow that moves from the one or more of any blower(s) (85) can be directed or pointed in one or more of any direction(s), angle(s), and/or orientation(s), preferably that is at least effective. Without limitation, the one or more of any blower(s) (85) can also be positioned and/or located at one or more of any angle(s), orientation(s), and/or geometry(s), preferably that is at least effective. Without being limited, the output of the blower(s) (85) can also be directed or pointed to one or more of any locations inside and/or outside of the aerosol generating apparatus (1). Without being limited, the one or more blower(s) (85) can also point in one or more of any directions toward or at the ceiling(s) at any effective angle(s), and they can also be motorized in a manner known in the art, so they can move and point their air/gas stream or output to or at various locations while operating.

Without being limited, the blower(s) (85) can be controlled and/or powered by the at least one microprocessor based controller (22). Also, without being limited, the blower(s) (85) can be used for purposes such as, but not limited to, assisting with moving of any aerosol(s) (40) and/or gas(s) within the treated room(s) and/or targeted area(s) (30) at any time(s). Without being limited, the blower(s) (85) can be any size(s) and have any volume of output measured in units such as, but not limited to, cubic feet per minute (cfm), preferably that is effective. The blower(s) (85) can be operated at one or more of any time(s) and for one or more of any length of time(s). It is preferred, without limitation, that the blower(s) (85) are at least operated within the treated room(s) and/or targeted area(s) (30), and at one or more of any effective time(s), and for one or more of any effective amount of time(s).

Figure 9:
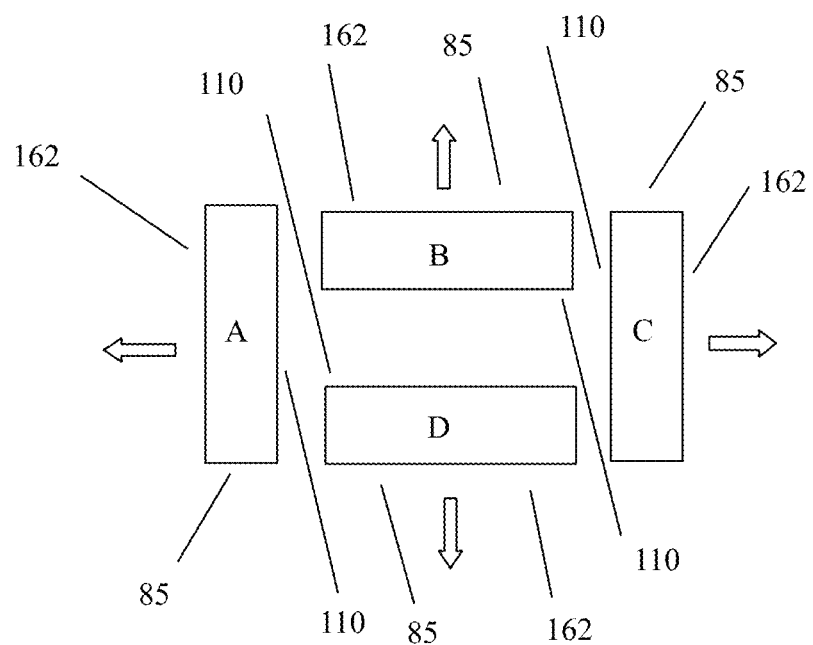
FIG. 9 is a top view of four blowers blowing outward into an enclosure of an ultrasonic aerosol generator.
Figure 10:
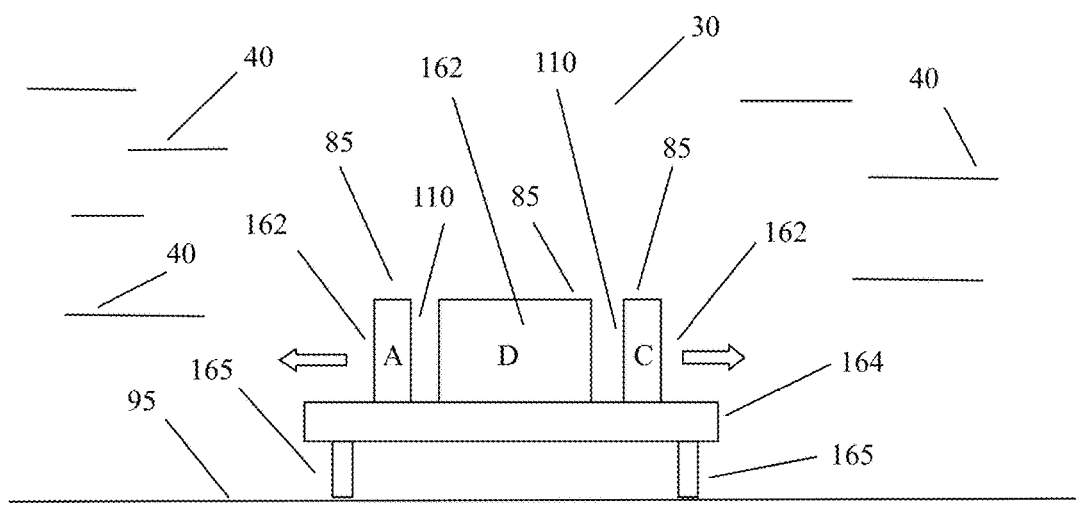
FIG. 10 is a side view of four blower blowing outward into an enclosure of an ultrasonic aerosol generator for dispersing aerosol contained in an enclosure.
Figure 11:
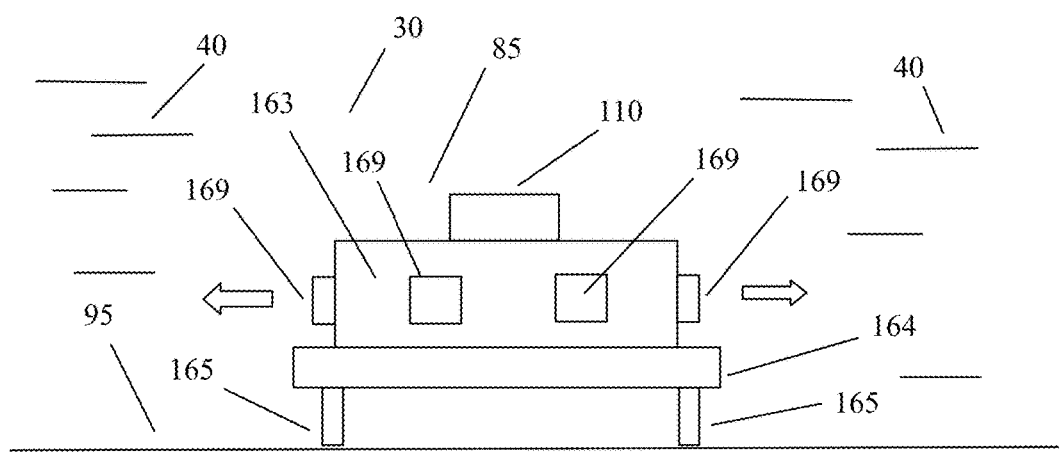
FIG. 11 is a side view of an ultrasonic aerosol generator for dispersing aerosol with a modified blower, an air/gas director with multiple air/gas outlets pointing in multiple directions in an enclosure immersed with deployed aerosol.
Figure 12:
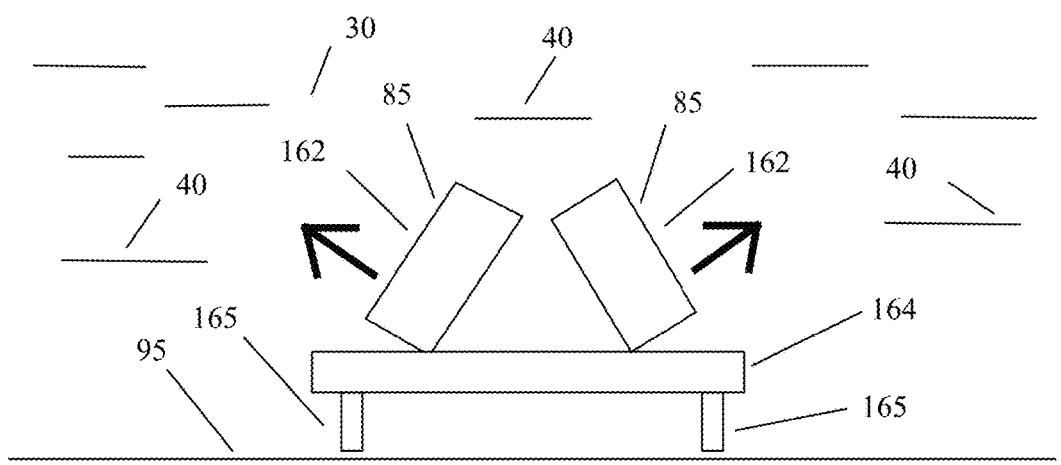
FIG. 12 is a side view of an ultrasonic aerosol generator with a modified blower assembly with multiple blowers angled upward in an enclosure immersed with deployed aerosol.
Figure 13:
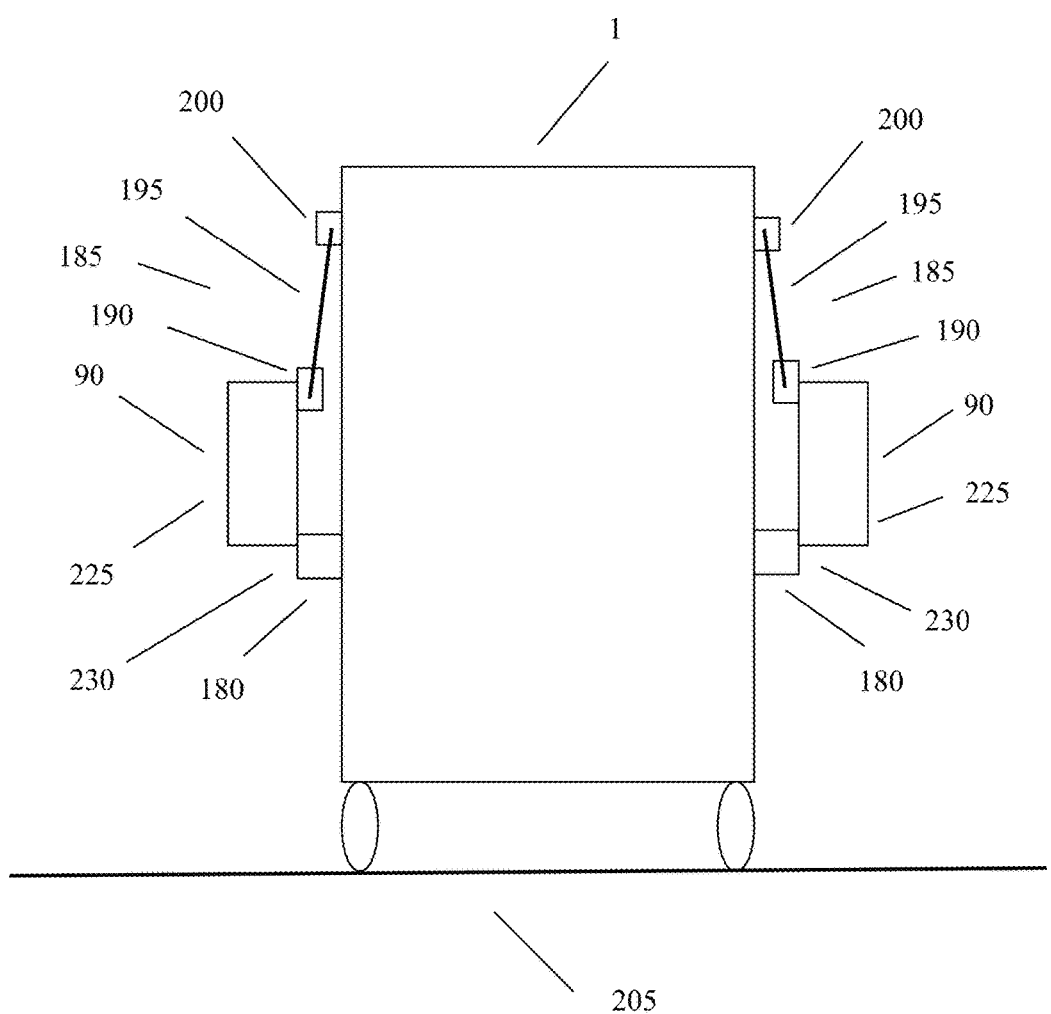
FIG. 13 is a front view of an ultrasonic aerosol generator with downward pivoting outboard fans in a stowed orientation.
Figure 14:
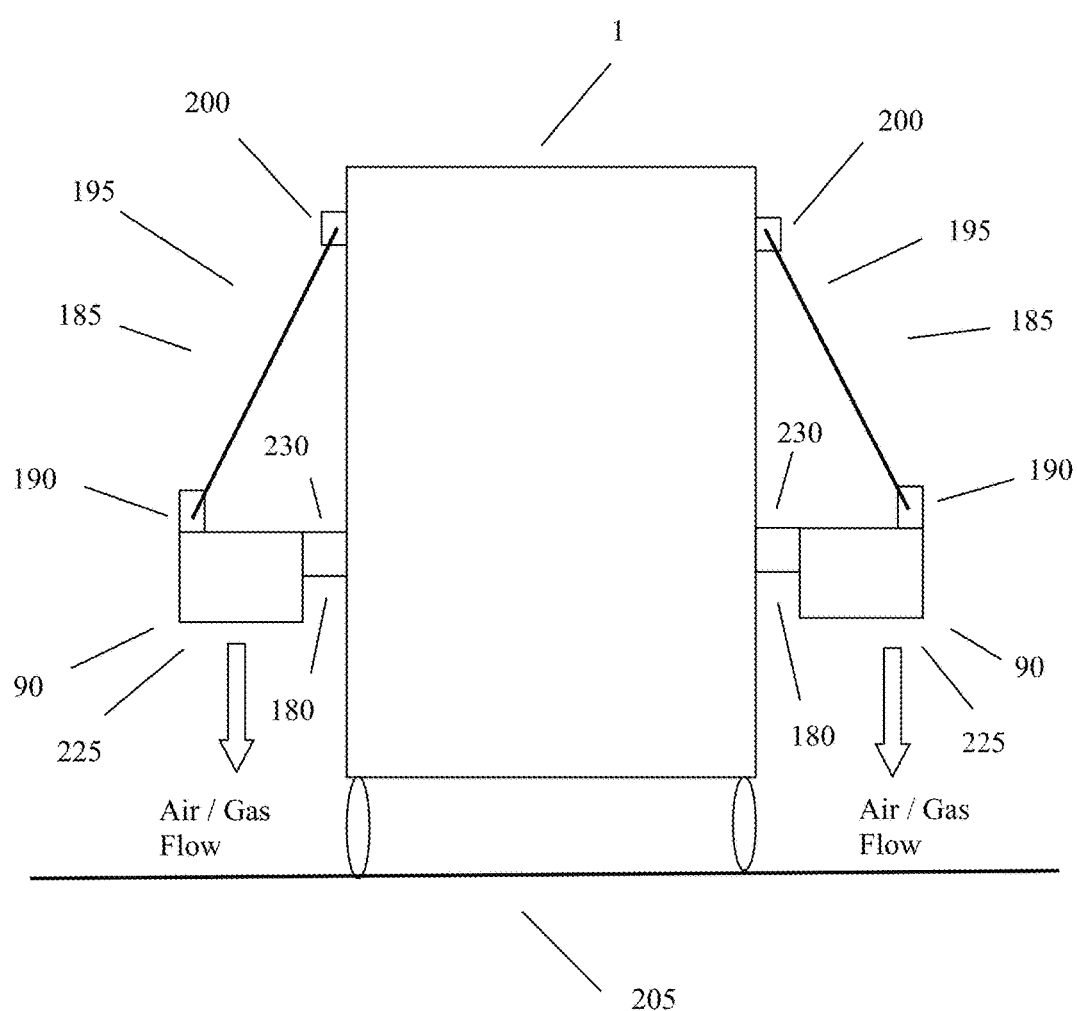
FIG. 14 is a front view of an ultrasonic aerosol generator with downward pivoting outboard fans in an activated orientation.

With reference to FIG. 4 and FIGS. 9-12, and according to an embodiment, and without limitation, the one or more of any blower(s) (85) can also be located independent from the aerosol generating apparatus (1), and can also be positioned and/or located at one or more of any angle(s), orientation(s), and/or geometry(s), preferably that is effective. Referring to FIGS. 9-10 and FIG. 12, and without limitation, the blower(s) (85) can have one or more of any intake(s) (110) through which substance(s) such as, but not limited to, the air/gas(s) or atmosphere within the treated room(s) and/or targeted area(s) (30) can flow into the blower(s) (85), and one or more of any outlets (162) through which substance(s) such as, but not limited to, the air/gas(s) or atmosphere within the treated room(s) and/or targeted area(s) (30) can flow out of the blower(s) (85).

Without being limited, the blower(s) (85) can be located and/or positioned at one or more of any effective distance(s) from the floor(s) (95) of the treated room(s) and/or targeted area(s) (30), preferably, and without limitation, between 0-80 inches or more from the floor(s) (95) of the treated room(s) and/or targeted area(s) (30), more preferably, and without limitation, between 0-60 inches from the floor(s) (95) of the treated room(s) and/or targeted area(s) (30), even more preferably, and without limitation, between 0-28 inches from the floor(s) (95) of the treated room(s) and/or targeted area(s) (30), very preferably, and without limitation, between 0-34 inches from the floor(s) (95) of the treated room(s) and/or targeted area(s) (30), extremely preferably, and without limitation, between 0-30 inches from the floor(s) (95) of the treated room(s) and/or targeted area(s) (30). It is also preferred, without limitation, that the upper most or highest part of the blower(s) (85) does not exceed these various maximum distances measured from the floor(s) (95) of the treated room(s) and/or targeted area(s) (30).

Referring to FIG. 4 and FIGS. 10-12, and without limitation, it is preferably intended to locate and/or position the one or more of any blower(s) (85) so that they move any effective quantity of air/gas(s) and deployed aerosol (40), at any effective velocity and/or speed, in one or more of any effective direction(s) from or moving away from the blower(s) (85), preferably in a 360 degree dispersion, deployment, and/or output radius, and also preferably along the the floor(s) (95) of the treated room(s) and/or targeted area(s) (30) and within one or more of any layer(s) of deployed aerosol (40), so that any effective quantity of air/gas(s) and aerosol (40) at least reaches one or more of any walls (168) and/or any effective vertical or angled surface(s), within the treated room(s) and/or targeted area(s) (30) (Herein called "Wall(s)") (168), and moves up and along and/or up and in any effective proximity to the walls (168), and then effectively beyond and/or above the one or more of any layer(s) or stratified layer(s) of any air/gas(s) and/or aerosol(s) (40), and more preferably and without limitation, effectively, near, close to, approximate to, and/or to, the one or surface(s) of the one or more more ceiling(s) (145), so that the deployed aerosol (40) can, evenly disperse, effectively distribute, effectively and evenly distribute, mix together with the other parts of the atmosphere within the targeted area(s) (30), completely disperse, and/or completely homogenize, within the targeted area(s) (30), without the size, performance, optical appearance, effectiveness, and/or efficacy of the aerosol (40) and/or treatment process, being adversely effected.

Referring to FIGS. 10-12, and without being limited, the one or more of any blower(s) (85) can also be suitably and effectively connected, positioned, and/or located, at one or more of any angle(s), orientation(s), and/or geometry(s), to one or more of any suitable, chassis(s), frame(s), and/or structure(s) (Herein called "Mounting Structure(s)") (164), that can effectively, hold, locate, and/or position, the one or more blower(s) (85). The mounting structure(s) (164) can also have, without limitation, one or more of any suitable and effective foot(s), leg(s), and/or support structure(s) (Herein called "Support Structure(s)") (165). The one or more blower(s) (85) can also be, without limitation, connected in one or more of any suitable and effective location(s) and/or position(s), to one or more of any effective means to disperse or direct the airflow that leaves the blower(s) (85) (Herein called "Air/gas Director(s)") (163) in one or more directions, and preferably in all directions or a 360 degree dispersion or distribution pattern.

Referring to FIG. 11, and without limitation, the inlet or intake (110) of the blower(s) (85), is located above the air/gas director(s) (163). In addition, and without limitation, the air/gas director(s) (163) have one or more, and preferably a plurality, of any effective outlets(s) (Herein called "Director Outlet(s)") (169), that can have any effective, size, shape, orientation(s), design(s), geometry(s), and direction(s) of output(s).

With reference to FIG. 1, FIG. 4, and FIGS. 6-8 and according to an embodiment, and without limitation, it is more preferred, without limitation, that at least an effective number of the one or more blower(s) (85), are mounted and/or incorporated into the design of the aerosol generating apparatus (1), and that their output, or the flow of the air/gas(s) that flow out of the blower(s) (85) is pointing downward, about downward, angled downward, and/or effectively downward, toward the floor(s) (95) of the treated room(s) and/or targeted area(s) (30) (otherwise called the "downward facing fan(s)") (90). Without being limited, the downward facing fan(s) (90) can also be independently located at one or more of any location(s) within the treated room(s) and/or targeted area(s) (30). Without being limited, the downward facing fan(s) (90) can be controlled and/or powered by the at least one microprocessor based controller (22).

Without being limited, the downward facing fan(s) (90) can be used for purposes such as, but not limited to, assisting with the effective moving of any aerosol(s) (40) and/or gas(s) within the treated room(s) and/or targeted area(s) (30) at any time(s). More specifically, and without being limited, the downward facing fan(s) (90) can be used for purposes such as, but not limited to: (a) effectively, moving, mixing together with the other parts of the atmosphere within the targeted area(s) (30), locating, removing, and/or disrupting, one or more of any layers of any air/gas(s) (Herein called "Air/gas(s) Layer(s)") (166), having any temperature(s) and/or humidity(s), that may be present at one or more of any locations and/or heights, within the treated room(s) and/or targeted area(s) (30), and (b) effectively, moving, mixing together with the other parts of the atmosphere within the targeted area(s) (30), locating, removing, and/or disrupting, one or more of any layers of any air/gas(s) and/or aerosol(s) (40) (Herein called "Aerosol Layer(s)") (167), having any temperature(s) and/or humidity(s), that may be present at one or more of any locations and/or heights, within the treated room(s) and/or targeted area(s) (30), and (c) effectively, moving, mixing together with the other parts of the atmosphere within the targeted area(s) (30), and/or locating, any aerosol(s) (40) that may be present at one or more of any locations and/or heights, having any temperature(s) and/or humidity(s), within the treated room(s) and/or targeted area(s) (30), so that the deployed aerosol (40) may, evenly disperse, evenly mix, effectively distribute or mix, effectively and evenly distribute, mix together with the other parts of the atmosphere within the targeted area(s) (30), completely disperse, and/or completely homogenize, within the targeted area(s) (30), without the size, performance, optical appearance, effectiveness, and/or efficacy of the aerosol (40) and/or treatment process, being adversely effected (Herein called "Evenly Dispersed Aerosol") (170).

Referring to FIG. 1, FIGS. 3-4, and FIGS. 6-8, and without limitation, it is preferably intended to locate and/or position the one or more of any downward facing fan(s) (90) so that they move any effective quantity of air/gas(s) and deployed aerosol (40), at any effective velocity and/or speed, in one or more of any effective direction(s) from or moving away from the downward facing fan(s) (90), preferably in a 360 degree dispersion, deployment, and/or output radius, and also preferably along the the floor(s) (95) of the treated room(s) and/or targeted area(s) (30) and within one or more of any layer(s) of deployed aerosol (40), so that any effective quantity of air/gas(s) and aerosol (40) at least reaches one or more of any walls (168) and/or any effective vertical or angled surface(s), within the treated room(s) and/or targeted area(s) (30) (Herein called "Wall(s)") (168), and moves up and along and/or up and in any effective proximity to the walls (168), and then effectively beyond and/or above the one or more of any layer(s) or stratified layer(s) of any air/gas(s) and/or aerosol(s) (40), and more preferably and without limitation, effectively, near, close to, approximate to, and/or to, the one or surface(s) of the one or more more ceiling(s) (145), so that the deployed aerosol (40) can, evenly disperse, effectively distribute, effectively and evenly distribute, mix together with the other parts of the atmosphere within the targeted area(s) (30), completely disperse, and/or completely homogenize, within the targeted area(s) (30), without the size, performance, optical appearance, effectiveness, and/or efficacy of the aerosol (40) and/or treatment process, being adversely effected.

Without being limited, the downward facing fan(s) (90) and/or the opening or outlet(s) (162) from which the flow of any air/gas(s) and/or aerosol (40) exits the downward facing fan(s) (90) can be located at any distance(s), preferably any effective distance(s) from the floor (95) of the targeted area(s) (30), more preferably located between about 0.10 inches to twenty feet or more above the floor(s) (95) within the treated room(s) and/or targeted area(s) (30), even more preferably located between about 0.25 inches to four feet above the floor(s) (95) within the treated room(s) and/or targeted area(s) (30), very preferably located between about 0.25 inches to two feet above the floor(s) (95) within the treated room(s) and/or targeted area(s) (30).

Without being limited, the air/gas(s) exiting the one or more of any downward facing fan(s) (90) can be directed in one or more of any downward direction(s) and/or angle(s). It is preferred, without limitation, that the output or outward flow of any air/gas(s) from any downward facing fan(s) (90) is directed against the floor (95) close to or about at a vertical orientation, and the air/gas(s) are able to flow outwards in a 360 degree pattern along the floor(s) (95) after impacting the floor(s) (95), preferably in an equal dispersion of air/gas(s) in all directions.

Without being limited, the downward facing fan(s) (90) can have any volume (ie: cubic feet per minute (cfm)) of output or outward flow. It is preferred, without limitation, that the output or outward flow from the downward facing fan(s) (90) is at least effective. It is more preferred, without limitation that the volume (ie: cubic feet per minute (CFM)) of output or outward flow is between 1 to 10,000 CFM or more. It is even more preferred, without limitation that the volume (ie: cubic feet per minute (CFM)) of output or outward flow is between 1 to 3,000 CFM or more. It is extremely preferred, without limitation that the volume (ie: cubic feet per minute (CFM)) of output or outward flow is between 2 to 2,000 CFM.

Without being limited, it is also preferred, without limitation, that the output, output volume, and/or airflow, that flows out from the downward facing fan(s) (90) is set, configured, and/or established so that one or more of any layer(s) of any deployed aerosol (40) and/or any layer(s) of any air/gas(s), of one or more of any temperature(s) and/or humidity level(s), that may be present at any time(s) within the treated room(s) and/or targeted area(s) (30), are not only effectively and/or efficiently removed, mixed together with the other parts of the atmosphere within the targeted area(s) (30), diminished, and/or disrupted, but this is accomplished so that the deployed aerosol (40) may evenly disperse, mix together with the other parts of the atmosphere within the targeted area(s) (30), completely disperse, and/or completely homogenize, within the targeted area(s) (30), without an adverse effect on things such as, but not limited to, the effectiveness and efficacy of the aerosol (40), the effectiveness and efficacy of the treatment process, the opacity of the aerosol (40), the density of the aerosol (40), the volume of the aerosol (40), the thickness of the deployed aerosol (40) or aerosol (40) cloud, the size of the aerosol (40) droplets.

With reference to FIG. 1, FIGS. 4, and 6-8 and according to an embodiment, and without limitation, the one or more of any downward facing fan(s) (90) can operate at one or more of any, time(s), step(s), and/or period(s) of time(s), and preferably for any effective amount of time, before, during, and/or after the deployment of any aerosol (40) into the treated room(s) and/or targeted area(s) (30).

Referring to FIGS. 1-4, FIGS. 6-8, and FIGS. 13-19, and according to an embodiment, and without limitation, at least one downward facing fan(s) (90) can also be controlled by at least one suitable PLC and/or microprocessor based controller(s) (22), and operated for one or more of any effective duration(s) of time(s), at one or more of any effective time(s), during the deployment of any aerosol (40) and/or vapor(s) from the aerosol generating apparatus (1) into any treated room(s) and/or targeted area(s) (30). For example, and without limitation, the PLC and/or microprocessor based controller(s) (22) can be programmed in a manner known to those skilled in the art, to operate the downward facing fan(s) (90) at any time(s) during and/or after the deployment of any aerosol (40) and/or vapor(s) from the aerosol generating apparatus (1) into the at least one treated room(s) and/or targeted area(s) (30). More specifically, it is preferred without limitation, that the PLC and/or microprocessor based controller(s) (22) can be programmed in a manner known to those skilled in the art, so that after any effective amount(s) and/or period(s) of time(s) the aerosol (40) and/or vapor(s) is deployed from the at least one aerosol generating apparatus(s) (1) into the one or more of any suitable treated room(s) and/or targeted area(s) (30), the at leas one downward facing fan(s) (90) can be operated for any effective amount of time(s). Without being limited, the deployment(s) of any aerosol (40) and/or vapor(s) into the one or more treated room(s) and/or targeted area(s) (30) can be paused or stopped during the operation of the one or more of any downward facing fan(s) (90).

In addition, it is more preferred without limitation, that the PLC and/or microprocessor based controller(s) (22) can also be programmed in a manner known to those skilled in the art, so that one or more of any additional and effective deployment(s) of any aerosol (40) and/or vapor(s) into the one or more treated room(s) and/or targeted area(s) (30), as well as one or more of any additional and effective operation(s) of the downward facing fan(s) (90) within the one or more treated room(s) and/or targeted area(s) (30), can occur at any effective time(s) and for any effective duration of time(s), after any initial deployment(s) of any aerosol (40) and/or vapor(s) into the treated room(s) and/or targeted area(s) (30) and/or any initial operation(s) of any downward facing fan(s) (90).

However, it is preferred, without limitation, to operate the downward facing fan(s) (90) as a calculated percentage of the the volume of the treated room(s) and/or targeted area(s) (30), when their operation is desired or needed. It is preferred, without limitation that at least an effective percent volume of the air/gas(s) and/or atmosphere within the treated room(s) and/or targeted area(s) (30) is moved during the operation of the downward facing fan(s) (90).

Without being limited, laboratory testing, has determined that the one or more time(s) when the downward facing fan(s) (90) are operated, and the duration or length of the one or more operation time(s) for the downward facing fan(s) (90), is impacted by various variables such as, but not limited to, (a) the cubic feet volume (cfm) or volume output for the downward facing fan(s) (90), (b) the volume of the treated room(s) and/or targeted area(s) (30), (c) the atmospheric temperature within the treated room(s) and/or targeted area(s) (30), (d) the dew point of or within the atmosphere within the treated room(s) and/or targeted area(s) (30), (e) the relative humidity of or within the atmosphere within the treated room(s) and/or targeted area(s) (30), that can be recorded at one or more of any location(s) within the treated room(s) and/or targeted area(s) (30), at one or more of any time(s), before, during, and/or after, the deployment of the aerosol (40) into the treated room(s) and/or targeted area(s) (30).

Without being limited, it has been found that operating the downward facing fan(s) (90) as a calculated percentage of the the volume of the treated room(s) and/or targeted area(s) (30), yields effective treatment results in the treated room(s) and/or targeted area(s) (30), and it can be calculated by taking the cubic feet volume (cfm) output specification for the output of the downward facing fan(s) (90) and multiplying it by a conversion factor known in the art to convert to seconds, then multiplying that resultant value by the operation time for the downward facing fan(s) (90), and then dividing that resultant value of this mathematical operation by the cubic volume of the treated room(s) and/or targeted area(s) (30), and then multiplying this outcome by one-hundred. For example, and without limitation, where the treated room(s) and targeted area(s) (30) "Volume" is about 2,500 ft^3, and the downward facing fan(s) (90) "Volume Output" is about 600 cubic feet per minute (cfm), and the "Operation Time" is about 10 seconds, a value of about four percent of the interior atmosphere or air/gas(s) volume should be moved in the treated room(s) and targeted area(s) (30), as shown and calculated below:

$$[[(600 \text{ ft}^3/1*1 \text{ min}/(60 \text{ sec}))*(10 \text{ sec})]/2500 \text{ ft}^3]*100$$

Without being limited, it is preferred, without limitation, that the downward facing fan(s) (90) are operated so that between 0.1 to 90 percent, more preferred between 0.25 to 30 percent, even more preferred between 1 to 25 percent, very preferred between 0.5 to 20 percent, and extremely preferred between 1 to 20 percent, of the air/gas(s) in the treated room(s) and/or targeted area(s) is moved by the downward facing fan(s) (90), at one or more of any time(s), for various and effective purposes as earlier mentioned in the present invention, in order to, mix together with the other parts of the atmosphere within the targeted area(s) (30), evenly disperse, completely disperse, and/or completely homogenize, the aerosol(s) (40) within the targeted area(s) (30) and/or any layer(s) of any type that may be present in the targeted area(s) (30).

Figure 5:
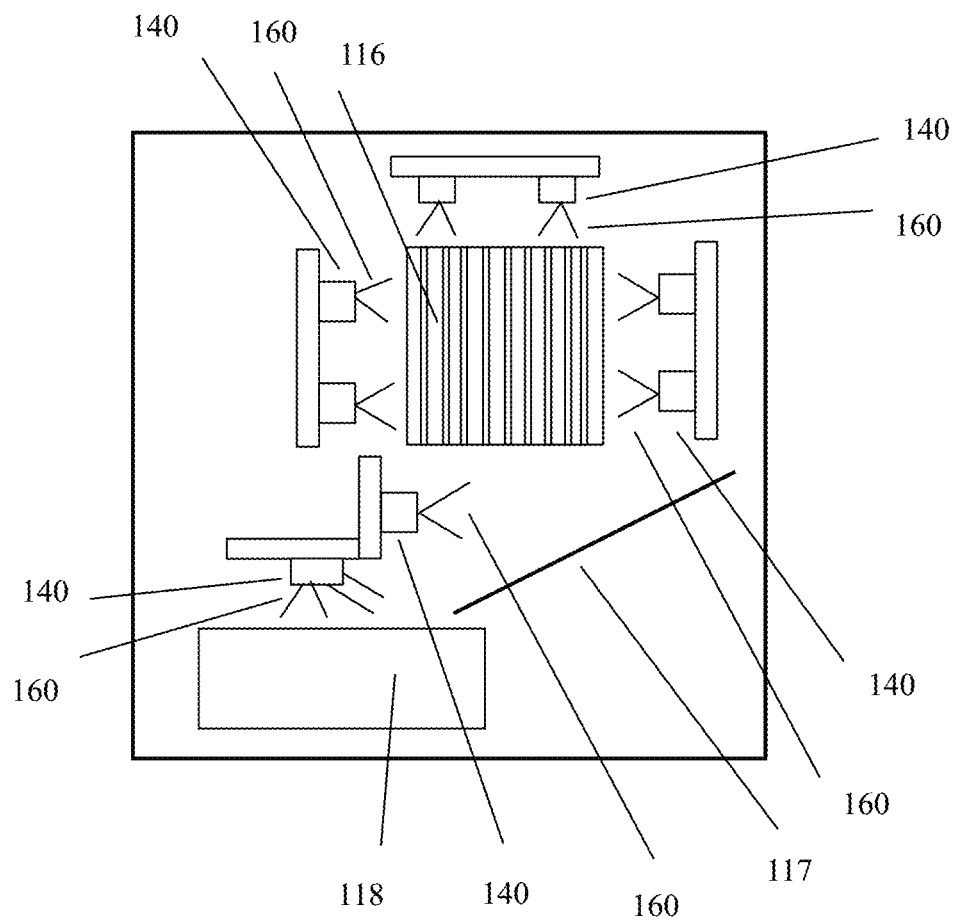
FIG. 5 is a cross sectional view of a dehumidification apparatus, where various components inside thereof can be disinfected by various spray or mist mechanism.

With reference to FIG. 1 and FIG. 5 and according to an embodiment, and without limitation, the aerosol generating apparatus (1) can also include one or more of any dehumidification apparatus(s) (80). Without being limited, the dehumidification apparatus(s) (80) can be or have any attributes or performance characteristics such as, but not limited to any: size, design, air flow, efficiency, performance, and capabilities. Without being limited, the dehumidification apparatus(s) (80) can also treat any volume of space. It is preferred, without limitation, that the dehumidification apparatus (80) is at least effective.

Without being limited, the dehumidification apparatus (80) can be operated at any time, preferably at any effective time and for any effective period of time. It is preferred, without limitation, that after the aerosol (40) has been effectively deployed into the treated room(s) and/or targeted area(s) (30), and more preferably after the aerosol (40) has had a chance to dwell within the treated room(s) and/or targeted area(s) (30) for an effective amount of time, the one or more dehumidification apparatus(s) (80) can operate, preferably for any effective amount of time, and dehumidify the air/gas(s) or atmosphere within the treated room(s) and/or targeted area(s) (30), until any relative humidity is reached that is considered suitable, effective, and/or desired.

With reference to FIG. 5 and according to an embodiment, and without limitation, the design and/or interior design of the dehumidification apparatus(s) (80) can also include one or more of any, aerosol and/or mist generating device(s), sprayer(s), spray nozzle(s), mister(s), liquid jet(s), coarse sprayer(s), and/or any other suitable means known in the art for spraying, jetting, aerosolizing, and/or applying liquid (Herein called "Spray Applicator(s)") (140), that can be used for deploying any effective, spray, liquid output, liquid jet, liquid stream, aerosol, and/or mist (Herein called "Mist") (160), of any liquid disinfectant and/or sanitizer liquid onto and/or into, the various parts of the dehumidification apparatus(s) (80) such as, but not limited to any, condensation coil(s) (116), condensation catch plate(s) (117) and/or catch tray(s) (118). Without being limited, any effective decontamination and/or treatment liquid such as, but not limited to any, disinfectant and/or sanitizer can be used. Also, without being limited, the one or more spray applicator(s) (140) can operate for any effective duration of time.

Without being limited, the various spray applicator(s) (140), can be used for purposes such as, but not limited to, offering a secondary source for disinfecting and/or sanitizing, any, location(s), parts, and/or component(s), within the dehumidification apparatus(s) (80) such as, but not limited to any, (a) coil(s), chill coil(s), pipe(s), chill pipe(s), and/or any other suitable structure(s) (Herein called "Condensation Coil(s)") (116) that are used to condense things such as, but not limited to any, water vapor, humidity, chemical vapor(s), gas(s), hydrogen peroxide vapor, and/or peroxyacetic acid vapor, from any air/gas(s) and/or atmosphere from within the targeted area(s) (30), (b) plate(s), and/or any other suitable structure(s) (Herein called "Condensation Catch Plate(s)") (117) that are used to catch any dripping condensation or condensate that originates from or drips off of, the one or more of any condensation coil(s) (116), (c) catch tray(s), pan(s), basin(s), and/or any other suitable part(s) or component(s) (Herein called "Catch Tray(s)") (118) that are used to catch and/or hold any liquid that flows from the condensation catch plate(s) (117).

Referring to FIG. 5, and without limitation, it is preferred, without limitation, that one or more of any spray applicator(s) (140) is directed effectively at one or more of any locations or parts of the dehumidification apparatus(s) (80) such as, but not limited to any, condensation coil(s) (116), catch plate(s) (117), and/or catch tray(s) (118), and more preferably including any effective locations such as, but not limited to the, front, sides, top, bottom, inside, amongst, around, intertwined, and/or back, of the one or more of any condensation coil(s) (116). Without being limited, one or more of any effective ultraviolet light source(s) or UV light(s) (not shown) can also be used at one or more of any effective locations within or inside the dehumidification apparatus(s) (80), in conjunction with any of the spray applicator(s) (140).

Without being limited, the spray applicator(s) (140) can deploy any aerosol, spray, and/or mist, with one or more of any characteristics such as, but not limited to any effective, size(s), density(s), concentration(s), deployment cone size(s), deployment rate(s). Without being limited, the one or more spray applicator(s) (140) can also effectively move back and forth and/or effectively pivot in one or more of any directions, preferably from their mounted location(s), all in a manner known to those skilled in the art.

Also, and without limitation, the one or more of any spray applicator(s) (140) can be mounted, positioned, and/or located at one or more of any angle(s), direction(s), and/or orientation(s). It is preferred, without limitation, that the at least one or more of any spray applicator(s) (140) are at least effective. It is preferred, without limitation, that the spray applicator(s) (140) are located at any effective distance(s) from the one or more of any targeted surface(s), part(s) and/or component(s). Without being limited, the spray applicator(s) (140) can be controlled, operated, and/or powered by the at least one microprocessor based controller (22).

With reference to FIG. 1 and according to an embodiment, and without limitation, the various air/gas(s) output or exhaust from the dehumidification apparatus (80) can be directed, moved, channeled, ducted, and/or flowed, to one or more of any locations, preferably that are effective, either outside of the aerosol generating apparatus (1), and/or inside of the aerosol generating apparatus (1). It is preferred, without being limited, that the various air/gas(s) output or exhaust from the one or more dehumidification apparatus(s) (80) is at least directly or indirectly moved, channeled, ducted, and/or flowed, to the outside of the aerosol generating apparatus (1). It is more preferred, without limitation, that the various air/gas(s) output or exhaust from the one or more dehumidification apparatus(s) (80) is at least directly or indirectly moved, channeled, ducted, and/or flowed, to and/or into the one or more of any air/gas inputs and/or intake orifice(s) (Herein called "Intake(s)) (110) of one or more of any downward facing fan(s) (90). It is even more preferred, without limitation, that the various air/gas(s) output or exhaust from the one or more dehumidification apparatus(s) (80) is at least directly or indirectly moved, channeled, ducted, and/or flowed, to and/or into one or more of any area(s), space(s), and/or compartment(s) (Herein called "Intake Compartment(s)") (100), that also communicates with and/or effectively interfaces with, at least the one or more intake(s) (110) of the one or more of any downward facing fan(s) (90).

Without being limited, moving the various air/gas(s) output or exhaust from the one or more dehumidification apparatus(s) (80) into the one or more of any air/gas inputs and/or intake orifice(s) or intake(s) (110) of the one or more of any downward facing fan(s) (90), and directing the output of the downward facing fan(s) (90) towards the floor(s) (95) of the treated room(s) and/or targeted area(s) (30) can offer various advantages such as, but not limited to, using the dehumidified and/or heated air/gas(s) output or exhaust, from the dehumidification apparatus(s) (80), to accelerate drying the floors around, near, and/or in proximity to, the downward facing fan(s) (90) and/or the aerosol generating apparatus (1).

Without being limited the intake compartment(s) (100) can be located in one or more of any effective locations within, or at least a part of, the aerosol generating apparatus(s) (1). Also, and without being limited, the intake compartment(s) (100) can be effectively sealed. Without limitation, the intake compartment(s) (100) can effectively interface, preferably effectively seal, with both the one or more of any air/gas(s) output(s) or exhaust from the dehumidification apparatus (80), and the one or more of any downward facing fan(s) (90) and/or their air/gas inputs and/or intake orifice(s) or intake(s) (110).

Also, and without being limited, one or more of any filters (Herein called "Intake Filter(s)") (105) can effectively interface, at one or more of any locations, with the aerosol generation apparatus (1) and/or one or more of its intake compartment(s) (100), so any quantity of any air/gas(s) or atmosphere from inside the treated room(s) and/or targeted area(s) (30) can flow, pass, and/or move, through the intake filter(s) (105), and into the various location(s) of the aerosol generation apparatus (1) such as, but not limited to, the intake compartment(s) (100). It is preferred, without limitation, that the intake filter(s) (105) are at least effective. Without being limited, the intake filter(s) (105) can filter for one or more things such as, but not limited to any, dust, carbon dust, particles, biological organism(s), virus(s), and/or aerosol(s). Without being limited, any air/gas(s) from the atmosphere or any air/gas(s) within the treated room(s) and/or targeted area(s) (30) can be filtered by any suitable filter known in the art (not shown) before it flows into and/or through any parts, component(s), and/or location(s), of the aerosol generating apparatus (1) such as, but not limited to any, dehumidification apparatus (80), activated charcoal filter(s) (115), and/or any transducer chamber(s) (20).

Also referring to FIG. 1, and according to an embodiment, and without limitation, the aerosol generating apparatus (1) can also include one or more of any suitable filter(s) to filter the air/gas(s) or atmosphere within the treated room(s) and/or targeted area(s) (30), to remove one or more of any airborne substance(s) such as, but not limited to any, gas(s), and/or vapor(s) (Herein called "Activated Carbon Filter(s)") (120). It is preferred, without limitation, that the activated carbon filter(s) (120) are at least effective.

Also, referring to FIG. 1*a*, and without being limited, one or more of any suitable and effective filters (Herein called "Output Filter(s)") (240), such as, but not limited to any HEPA filter(s) known to those skilled in the art, can also be suitably and effectively used, located, and positioned, in any suitable and effective manner(s) known to those skilled in the art, to effectively filter any air/gas(s) that exits the one or more of any dehumidification apparatus(s) (80) and/or one or more of any activated carbon filter(s) (120), and preferably and without limitation, filters any air/gas(s) that exits any dehumidification apparatus(s) (80) and/or any activated carbon filter(s) (120) before the various air/gas(s) enters the one or more of any intake compartment(s) (100), and more preferably and without limitation, filters any air/gas(s) that exits any dehumidification apparatus(s) (80) and/or any activated carbon filter(s) (120) at least before the various air/gas(s) exits the aerosol generating apparatus(s) (01). Without being limited, one or more of any air/gas outlet(s) for any intake compartment(s) (100), through which any air/gas(s) can pass out of the intake compartment(s) (100), can also include one or more of any suitable and effective charcoal activated filter(s) (not shown) and/or one or more of any output filter(s) (240), to suitably and effectively filter any air/gas(s) leaving the intake compartment(s) (100), all in a manner known to those skilled in the art. Also, and without being limited, the dehumidification apparatus(s) (80) can also include one or more of any suitable and effective source(s) of pressurized air such as, but not limited to any, fan(s), air pump(s), and/or blower(s), all in a manner known to those skilled in the art.

Without being limited, one or more of any suitable fan(s) or blower(s) (Herein called "Filter Blower(s)") (125) can be directly and/or indirectly interfaced effectively with the activated carbon filter(s) (120), and are used to move the air/gas(s) or atmosphere from within the treated room(s) and/or targeted area(s) (30) through the activated carbon filter(s) (120). Without being limited, the filter blower(s) (125) can be controlled and/or powered by the at least one microprocessor based controller (22). It is preferred, without limitation, that the filter blower(s) (125) are at least effective.

Without being limited, the filter blower(s) (125) and activated carbon filter(s) (120) can be operated at any time, preferably at any effective time and for any effective period of time. It is preferred, without limitation, that after the aerosol (40) has been deployed into the treated room(s) and/or targeted area(s) (30), and more preferably after the aerosol (40) has effectively dwelled within the treated room(s) and/or targeted area(s) (30) for any effective amount of time, the air/gas(s) or atmosphere from within the treated room(s) and/or targeted area(s) (30) is not moved through the activated carbon filter(s) (120) until after the relative humidity in the treated room(s) and/or targeted area(s) (30) is preferably at least below ninety percent (90%), and more preferably below eighty-five percent (85%), and even more preferably below eighty percent (80%). Without being limited, this can prevent the activated carbon filter(s) (120) from becoming saturated with liquid from the aerosol (40) droplets and/or excessive humidity.

With reference to FIG. 1*a*, air goes through the carbon activated filter (120) and then through the filter blower (125). Exhaust from the filter blower (125) enters the intake compartment (100) and the air from the filter blower (125) exits the intake compartment through the at least one downward facing fan (90). The combined airflow from the filter blower (125) and the dehumidifier (80), maintain approximately equal airflow for the downward facing fan (90). Further, the downward facing fan (90) helps dry and evacuate the inner electronics. The downward facing fan (90) also ensures that an inside of a cabinet of the aerosol generating apparatus (1) remains free and condensation and residue. A controlled heater unit (not shown) may be placed adjacent to the carbon activated filter (120) to control filter saturation, thus improving the efficiency of the carbon activated filter (120). Warm dry air generated the controlled heated unit is also beneficial when directed to the floor area after the destratification process by the downward facing fan (90).

Also, with reference to FIGS. 5, 5*a*, and 5*b*, and without limitation, one or more, but preferably and without limitation, more than one, and even more preferably, and without limitation, at least an effective number, of any spray applicator(s) (140), but preferably and without limitation, at least any effective spray applicator(s) (140), can be located in and/or at one or more of any location(s), but preferably and without limitation, at least at one or more of any effective location(s), to effectively sanitize, disinfect, high-level disinfect, sterilize, and/or effectively treat, the one or more of any condensation coil(s) (116) and/or any associated and/or connected part(s).

Without being limited, FIG. 5*a* shows a side view, and FIG. 5*b* shows a top view, of one or more of any condensation coil(s) (116), and any effective number of, and more preferably and without limitation, more than one of, any effective spray applicator(s) (140) that are effectively positioned and located at one or more of any effective location(s) such as, but not limited to, between, along, below, on the side(s) of, and/or above, the one or more condensation coil(s) (116), to effectively treat the condensation coil(s) (116) and/or any associated and/or connected part(s), but more preferably and without limitation, to effectively sanitize, disinfect, high-level disinfect, and/or sterilize, preferably, and without limitation, all of the exterior surface(s), and/or at least all of the targeted surface(s), of the condensation coil(s) (116) and/or any other part(s), associated part(s), and/or connected part(s).

Without being limited, one or more of any spray applicator(s) (140) can also be located and positioned at one or more of any suitable and effective location(s) such as, but not limited to, embedded within and/or amongst, the one or more of any condensation coil(s) (116), but it is preferred, without limitation, that the spray applicator(s) (140) are at least effectively located and positioned, above, along, and/or below, any condensation coil(s) (116), and it is more preferred without limitation, that one or more of any effective spray applicator(s) (140) are effectively located and positioned at least at one or more of any effective location(s) such as, but not limited to, above, below, inside, along the side(s) of, embedded within, amongst, between, along, around, intertwined, and/or in any effective proximity to, any condensation coil(s) (116), and it is even more preferred, without limitation, that one or more of any effective spray applicator(s) (140) are effectively located and positioned at least at one or more effective location(s) to effectively surround and/or treat any condensation coil(s) (116).

Figure 5A:
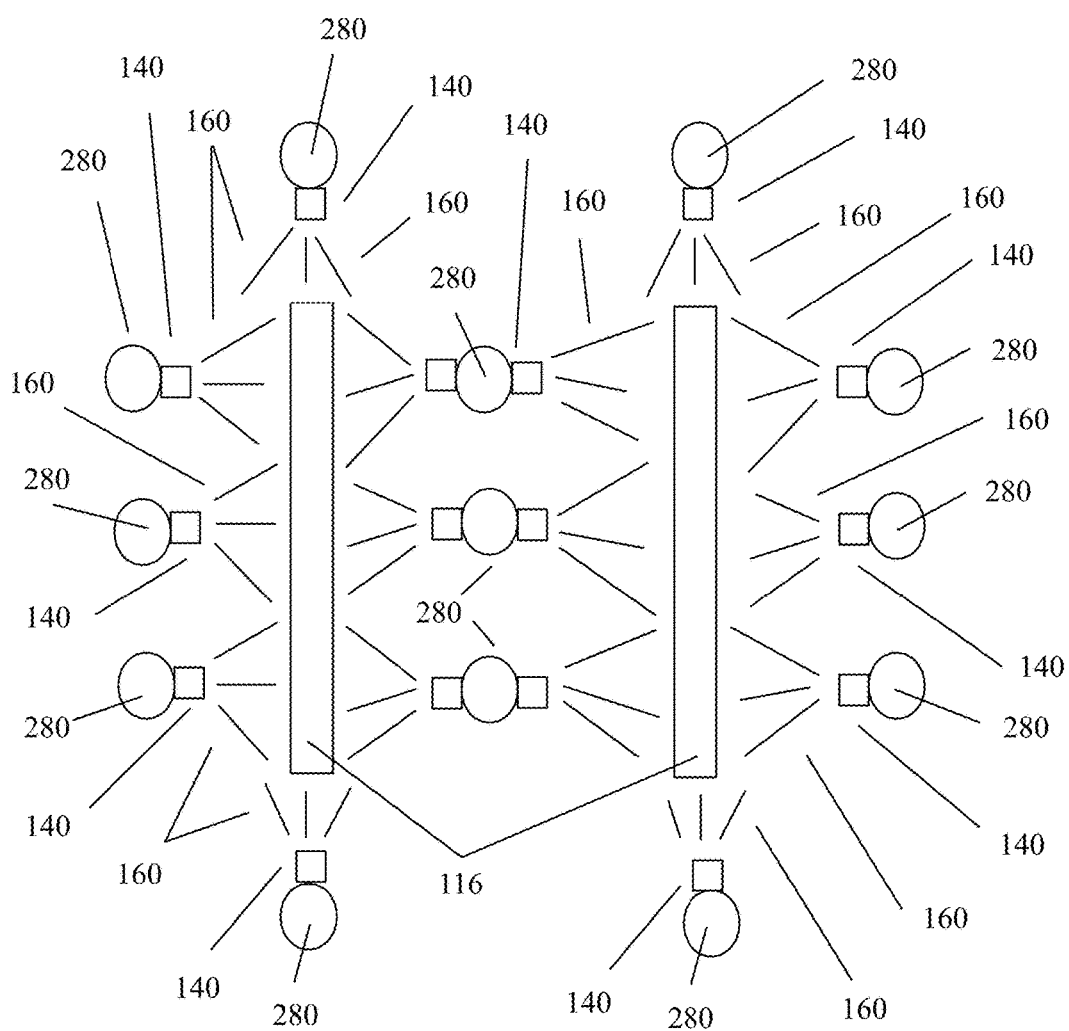
FIG. 5a is a side view of a dehumidification coil being disinfected by a spray mist mechanism.
Figure 5B:
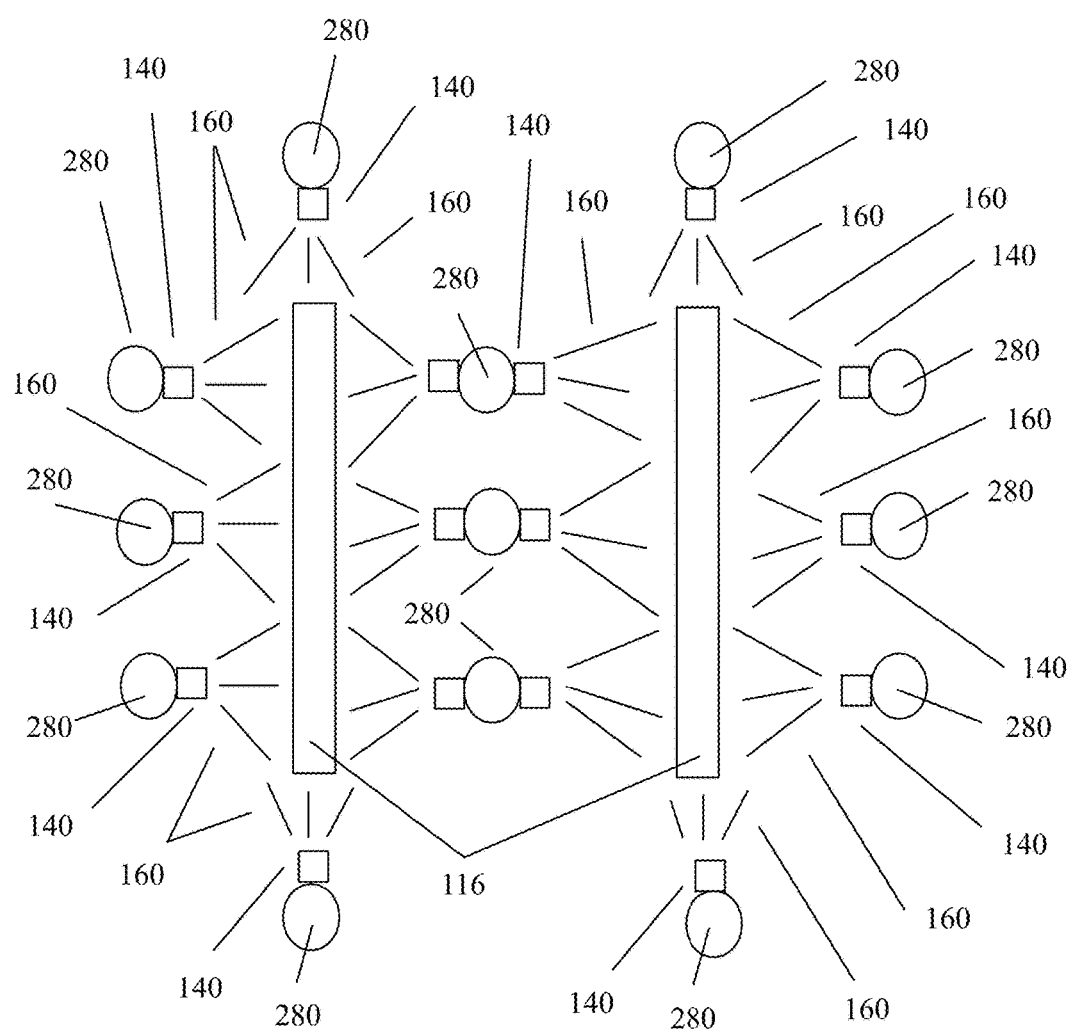
FIG. 5b is a top view of a dehumidification coil being disinfected by a spray mist mechanism.

Referring to FIGS. 5, 5a, and 5b, and without limitation, the spray applicator(s) (140) can be suitably connected to one or more of any suitable, tube(s), pipe(s), conduit(s), and/or tunnel(s) (Herein called "Applicator Supply Line(s)") (280), that can suitably connect to one or more of any suitable source(s) of any suitable and effective applied agent(s) and/or liquid(s) (Herein called "Coil Treatment Liquid(s)") (183), such as, but not limited to any, sanitizer(s), disinfectant(s), high-level disinfectant(s), and/or sterilant(s), that can also be, without being limited, heated to any effective temperature(s).

Without being limited, the coil treatment liquid(s) (183) can be heated to one or more of any effective temperature(s) at any effective time(s) using one or more of any effective means for heating the coil treatment liquid(s) (183) known to those skilled in the art, at one or more of any suitable and effective location(s). It is preferred, without limitation, that the coil treatment liquid(s) (183) are at least heated to any effective temperature(s) so that they are effective and do not freeze or form any ice when applied. It is more preferred, without limitation, that the coil treatment liquid(s) (183) are heated to any effective temperature(s) between, at, and/or about, the freezing point of the coil treatment liquid(s) (183) and the boiling point of the coil treatment liquid(s) (183).

It is even more preferred, without limitation, that the coil treatment liquid(s) (183) are heated to any effective temperature(s) of at least 33 degree Fahrenheit or higher. It is very preferred, without limitation, that the coil treatment liquid(s) (183) are heated to any temperature(s) between 50 to 208 degree Fahrenheit. It is extremely preferred, without limitation, that the coil treatment liquid(s) (183) are heated to any temperature(s) between 80 to 195 degree Fahrenheit. It is also preferred, without limitation, that the coil treatment liquid(s) (183) are heated to one or more of any suitable and effective temperature(s) between, at, and/or about, any freezing point(s) of the coil treatment liquid(s) (183) and any boiling point(s) of the coil treatment liquid(s) (183), and then applied to any targeted surface(s) at any suitable and effective temperature(s), and at any suitable and effective time(s).

Without being limited, one or more of any effective spray applicator(s) (140), located at one or more any effective location(s), can also be used to treat, sanitize, disinfect, and/or sterilize, one or more of any applicator supply line(s) (280), spray applicator(s) (140), and/or any associated and/or connected part(s), at one or more of any suitable and effective location(s), at any suitable and effective time(s). Without being limited, the condensation coil(s) (116), can also include one or more of any, chilled surfaces and/or structure(s), such as, but not limited to one or more of any suitable and effective, plate(s), chill plate(s), chilled plate(s), refrigerated plate(s), cooled plate(s), condensation forming plate(s), and/or any other condensation surface(s), all in a manner known to those skilled in the art.

Also, with reference to FIGS. 5, 5a, and 5b, and without limitation, one or more, but preferably and without limitation, more than one, and even more preferably, and without limitation, at least an effective number, of any spray applicator(s) (140), but preferably and without limitation, at least any effective number of any effective spray applicator(s) (140), can be located in and/or at one or more of any location(s), but preferably and without limitation, at least at one or more of any effective location(s), to effectively, sanitize, disinfect, high-level disinfect, sterilize, and/or effectively treat, the one or more of any condensation coil(s) (116) and/or any associated and/or connected part(s).

Without being limited, and without limitation, FIG. 5a shows a side view of one or more of any condensation coil(s) (116), and any effective number of, and more preferably and without limitation, more than one of, any effective spray applicator(s) (140) that are effectively positioned and located at one or more of any effective location(s) such as, but not limited to anywhere, above, below, between, along, and/or at the sides of, the one or more condensation coil(s) (116), to effectively treat the condensation coil(s) (116) and/or any associated and/or connected part(s), but more preferably and without limitation, to effectively, sanitize, disinfect, high-level disinfect, and/or sterilize, preferably, and without limitation, all of the surface(s) and/or at least all of the targeted surface(s) of the condensation coil(s) (116) and/or any associated and/or connected part(s).

Without being limited, and without limitation, FIG. 5b shows a top and/or bottom view of one or more of any condensation coil(s) (116), and any effective number of, and more preferably and without limitation, more than one of, any effective spray applicator(s) (140) that are effectively positioned and located at one or more of any effective location(s) such as, but not limited to anywhere, above, below, between, along, and/or at the sides of, the one or more condensation coil(s) (116), to effectively treat the condensation coil(s) (116) and/or any associated and/or connected part(s), but more preferably and without limitation, to effectively, sanitize, disinfect, high-level disinfect, and/or sterilize, preferably, and without limitation, all of the surface(s) and/or at least all of the targeted surface(s) of the condensation coil(s) (116) and/or any associated and/or connected part(s).

Without being limited, the one or more of any spray applicator(s) (140) can be located and positioned at one or more of any location(s) such as, but not limited to, above, below, between, along, and/or effectively near one or more of any sides of, the one or more of any condensation coil(s) (116), and at one or more of any effective, orientation(s), angle(s), and/or directions. Without being limited, the spray applicator(s) (140) can be positioned and located at one or more of any suitable and effective location(s) using one or more of any suitable and effective means and/or apparatus(s) such as, but not limited to any, bracket(s), holder(s), clamp(s), and/or any other suitable and effective means, part(s), design(s), and/or apparatus(s), known to those skills in the art.

It is preferred, without limitation, that the spray applicator(s) (140) are at least effectively located and positioned anywhere, above, between, along, and/or effectively near one or more of any sides of, any condensation coil(s) (116), and it is more preferred without limitation, that one or more of any effective spray applicator(s) (140) are effectively located and positioned at least at one or more of any effective location(s), above, below, inside, amongst, between, along, around, intertwined amongst, in effective proximity to, and/or effectively approximate to the sides of, any condensation coil(s) (116), and it is even more preferred, without limitation, that one or more of any effective spray applicator(s) (140) are effectively located and positioned at least at one or more of any effective location(s) to effectively, completely surround and/or partly surround, and sanitize, disinfect, high-level disinfect, and/or sterilize, any condensation coil(s) (116).

Referring to FIGS. 5, 5a, and 5b, and without limitation, the spray applicator(s) (140) can be suitably connected to one or more of any suitable, tube(s), pipe(s), conduit(s), and/or tunnel(s) (Herein called "Applicator Supply Line(s)") (280), that can suitably connect to one or more of any suitable source(s) of any suitable and effective applied agent(s) and/or liquid(s) such as, but not limited to any, sanitizer(s), disinfectant(s), high-level disinfectant(s), and/or sterilant(s), that can also be, without being limited, heated to any effective temperature(s). Without being limited, any number of spray applicator(s) (140), at any effective location(s), can also be used to treat, sanitize, disinfect, and/or sterilize, the exterior of any applicator supply line(s) (280) and/or any associated and/or connected part(s).

Without being limited, the condensation coil(s) (116), can also include, but is not limited to any, cooled, chilled, and/or refrigerated, surfaces and/or structure(s), such as, but not limited to any one or more of any suitable and effective, plate(s), tube(s), pipe(s), and/or conduit(s).

Figure 20:
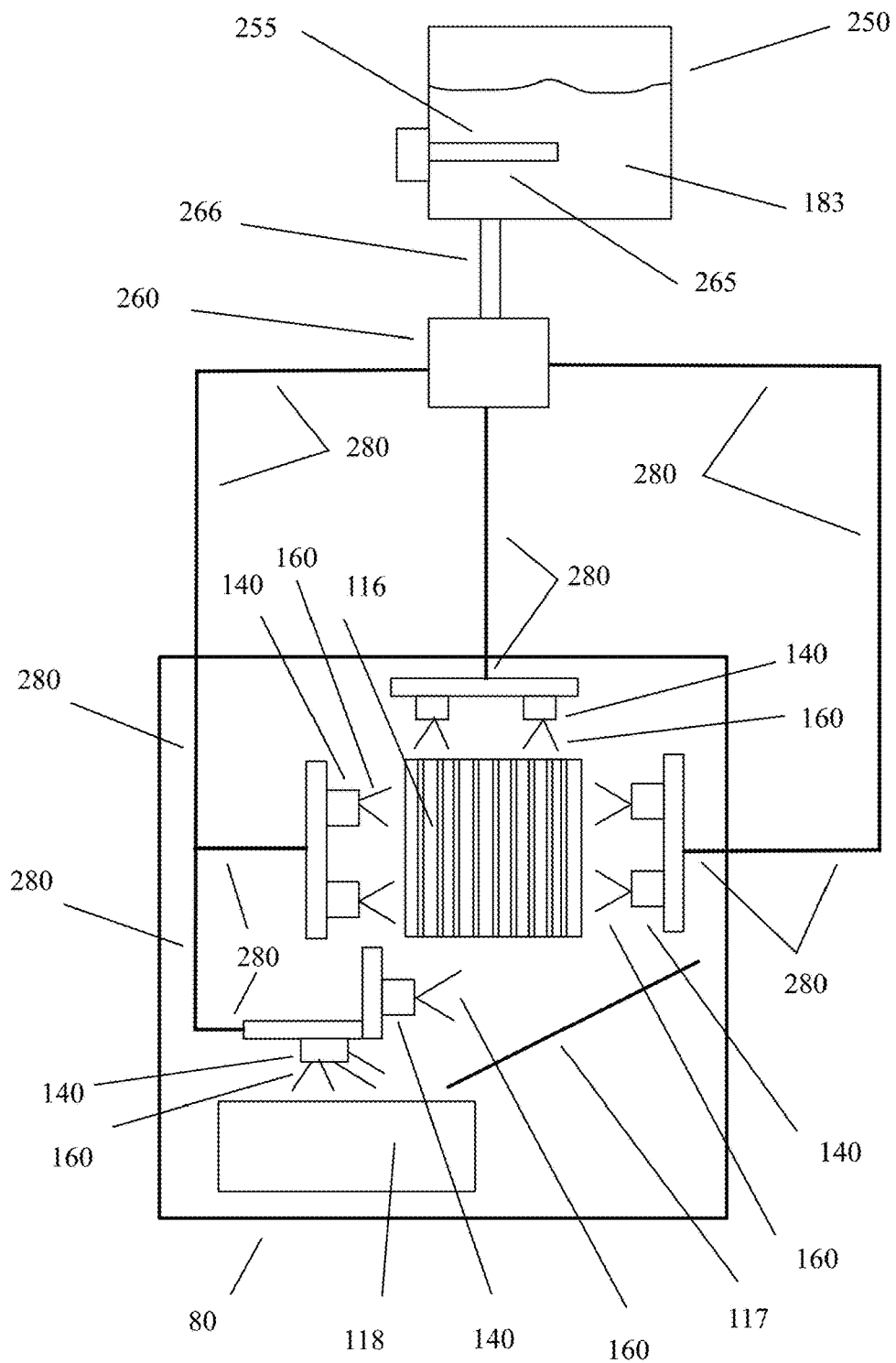
FIG. 20 is a cross sectional view of cooling coils inside a dehumidifier being sprayed with a heat treatment liquid.

Referring to FIG. 20, and without limitation, the one or more of any suitable and effective applicator supply line(s) (280) can suitably and effectively connect with one or more of any suitable and effective means to hold any coil treatment liquid(s) (183) such as, but not limited to any, tank(s), vessel(s), container(s), and/or any other suitable and effective means for holding and/or storing any liquid(s) known to those skilled in the art (Herein called "Treatment Liquid Tank(s)") (250). Without being limited, the coil treatment liquid(s) (183) can be heated in one or more of any suitable and effective location(s), at any suitable and effective time(s), using one or more of any suitable and effective means (Herein called "Treatment Liquid Heater(s)") (255), all in a manner known to those skilled in the art. It is preferred, without limitation, that the coil treatment liquid(s) (183) is effectively heated in one or more of any suitable and effective treatment liquid tank(s) (250), using one or more of any suitable and effective means (255) to heat the liquid (183) inside the treatment liquid tank(s) (250) such as, but not limited to any, suitable and effective heater element(s) (265), all in a manner known to those skilled in the art. It is preferred, without limitation, that at least one treatment liquid heater(s) (255) is suitably and effectively, connected, interfaced, located and/or positioned, with and/or within the treatment liquid tank(s) (250), all in a manner known to those skilled in the art.

Without being limited, the coil treatment liquid(s) (183) can also be heated at and/or in one or more of any suitable and effective location(s), at any suitable and effective time(s), during its journey and/or movement to the one or more spray applicator(s) (140), all in a manner known to those skilled in the art. Without being limited, the treatment liquid tank(s) (250) can be any suitable and effective, size(s), shape(s), material(s) of construction, and/or design(s), all in a manner known to those skilled in the art.

Without being limited, the coil treatment liquid(s) (183) can be pumped, flowed, and/or moved, from one or more of any treatment liquid tank(s) (250) to one or more of any spray applicator(s) (140), using any suitable and effective means known to those skilled in the art, and at any suitable and effective, flow rate(s), velocity(s), speed(s), volume(s) per unit of time(s), pressure(s), all in a manner known to those skilled in the art. It is preferred, without limitation, that the coil treatment liquid(s) (183) is pumped, at any suitable and effective time(s), to the one or more of any spray applicator(s) (140), using one or more of any suitable and effective pressurized means and/or pump(s) (Herein called "Pump(s)") (260), all in a manner known to those skilled in the art. Without being limited, the one or more of any pump(s) (260) can suitably and effectively connect to the treatment liquid tank(s) (250) via one or more of any suitable and effective, pipe(s), conduit(s), and/or tube(s) (Herein called "Pump Supply Tube(s)") (266), all in a manner known to those skilled in the art.

Without being limited, heating the coil treatment liquid(s) (183) to any suitable and effective temperature(s) before applying it to any targeted surfaces such as, but not limited to any, condensation coil(s) (116), can provide advantages such as, but not limited to, preventing the coil treatment liquid(s) (183) from freezing on various surfaces such as, but not limited to any, condensation coil(s) (116), and/or accelerating the drying of any treated surface(s) after they have been in contact with the heated coil treatment liquid(s) (183).

Without being limited, the coil treatment liquid(s) (183) can include one or more of any suitable and effective, liquid compound(s), solution(s), and/or agent(s), such as, but not limited to any, sanitizer(s), disinfectant(s), high-level disinfectant(s), and/or sterilant(s), known to those skilled in the art. It is preferred, without limitation, that the coil treatment liquid(s) (183) is any suitable and effective, peracetic acid solution(s) and/or bleach solution(s), all in a manner known to those skilled in the art.

Without being limited, the one or more of any surface(s) treated by the spray applicator(s) (140), such as, but not limited to any condensation coil(s) (116), can also be effectively rinsed and/or treated with any suitable and effective alcohol solution(s) after they undergo a first treatment by any coil treatment liquid(s) (183). It is preferred, without limitation, that the said alcohol solution(s) is also applied by the one or more of any suitable and effective spray applicator(s) (140) and it is also effectively heated to any suitable and effective temperature(s).

Figure 6:
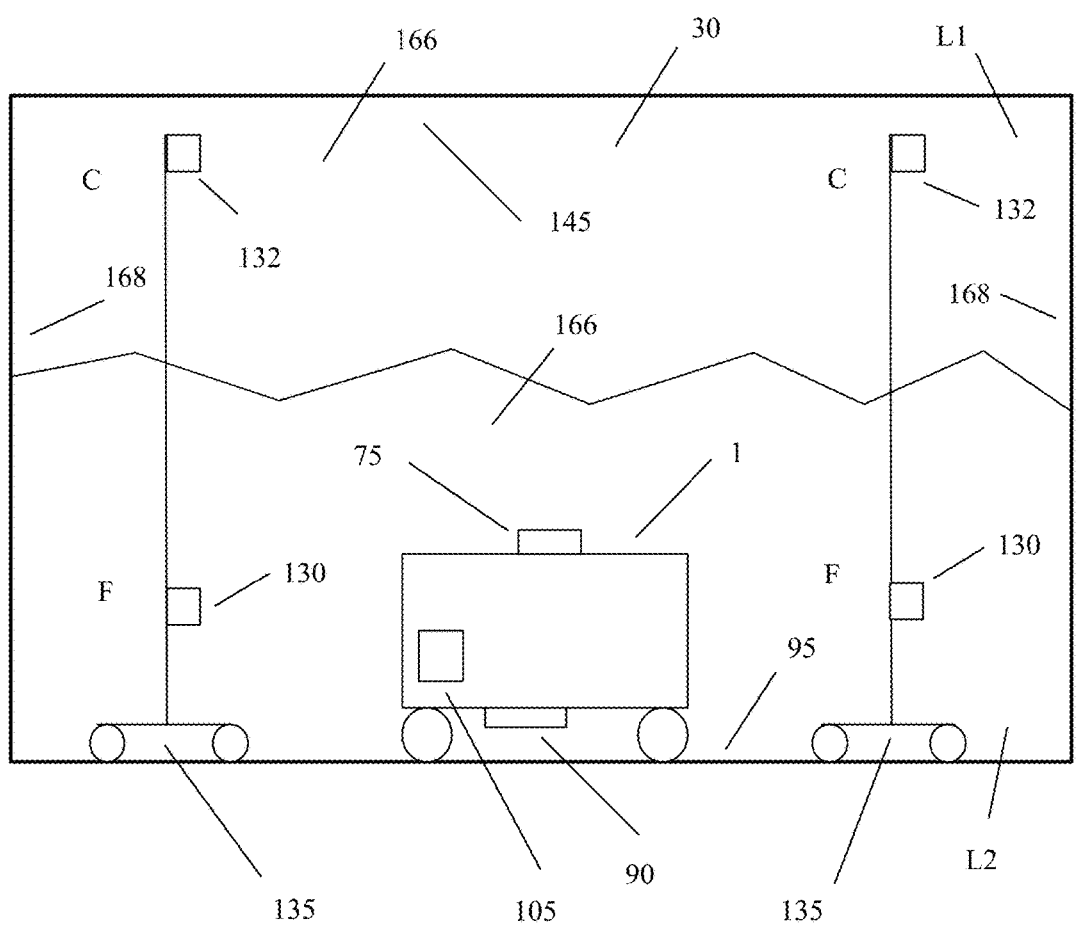
FIG. 6 is a front view of an ultrasonic aerosol generator positioned inside an enclosure or room, where at least one layer of air/gas is located in an upper portion thereof.
Figure 7:
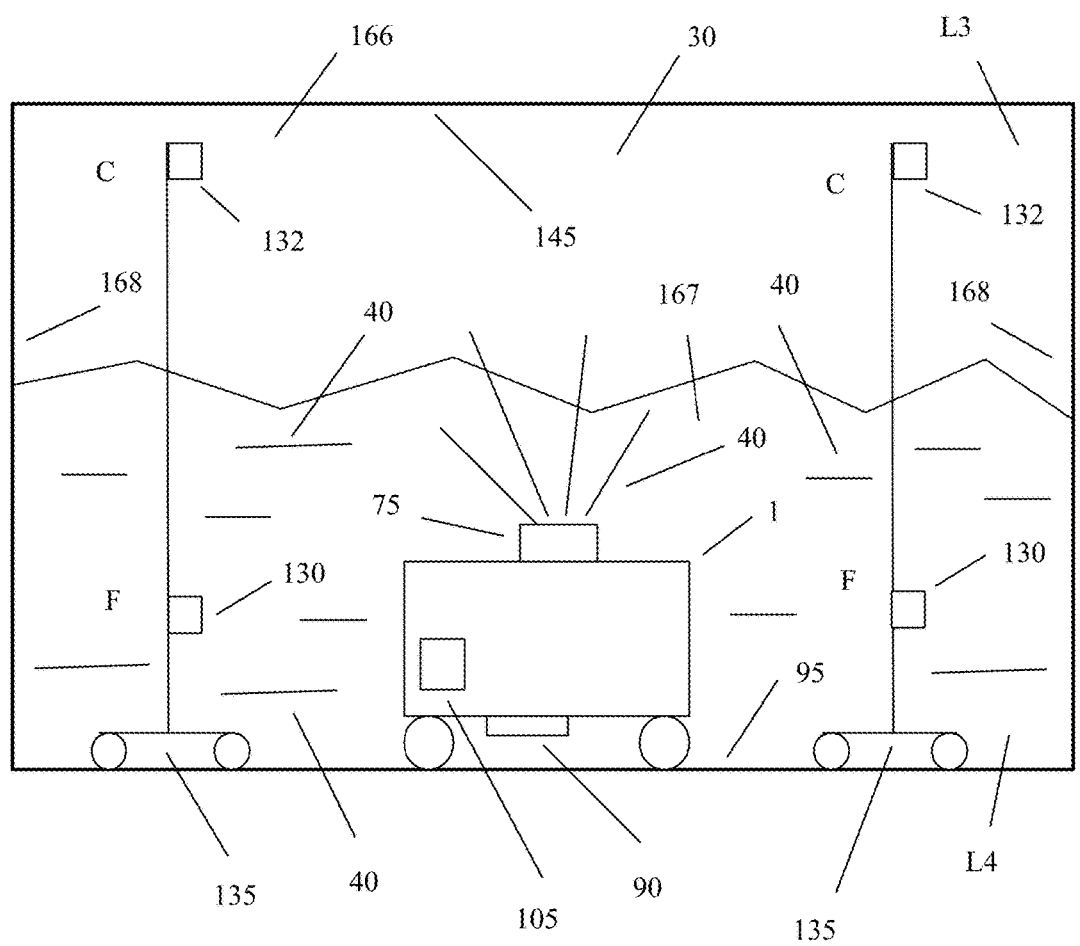
FIG. 7 is a front view of an ultrasonic aerosol generator positioned inside an enclosure or room, where at least one layer of air/gas is located in an upper portion thereof and an ultrasonic aerosol generator is generating a disinfecting aerosol.
Figure 8:
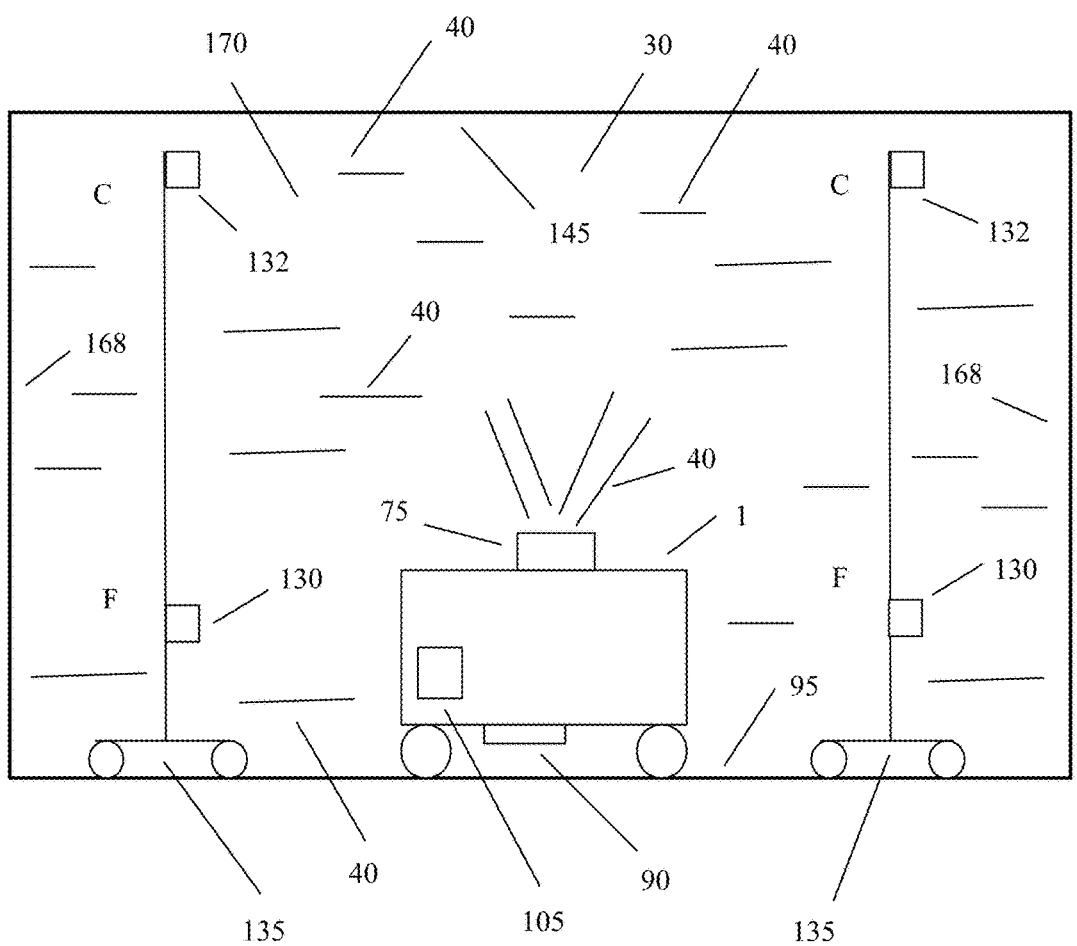
FIG. 8 is a front view of an ultrasonic aerosol generator positioned in an enclosure or where the deployed aerosol is evenly and effectively dispersed therein.

With reference to FIGS. 6-8 and according to an embodiment, and without limitation, one or more of any environment condition sensor(s) (Herein called "Environment Sensor(s)") (130, 132) can be used to sense, monitor, and/or report, one or more of any environment condition(s), at one or more of any suitable and effective location(s), within the treated room(s) and/or targeted area(s) (30) at any time, such as, but not limited to any, temperature(s), dew point(s), and/or humidity(s). Without being limited, there is at least one lower environmental sensor (130) and at least one lower environmental sensor (132).

The one or more of any environment sensor(s) (130, 132) can be located at one or more of any location(s) and/or height(s) within the treated room(s) and/or targeted area(s) (30). It is preferred, without limitation, that the environment sensor(s) (130, 132) are at least located at any effective location(s) and/or height(s) within the treated room(s) and/or targeted area(s) (30).

Without being limited, the one or more of any environment sensor(s) (130, 132 can communicate with one or more of any aerosol generating apparatus (1) and/or one or more of any remote control and communication device(s) or apparatus(s), in any effective way known to those skilled in the art. Also, and without limitation, the environment sensor(s) (130, 132) can be powered and/or communicate with the at least one microprocessor based controller (22) and/or the aerosol generating apparatus (1), via any wired means, all in a manner known to those skilled in the art. However, it is preferred, without limitation, that the environment sensor(s) (130, 132) are battery powered and communicate via any effective wireless means with the microprocessor based controller (22), all in a manner known to those skilled in the art.

Referring to FIG. 6-8 it is preferred, without limitation, that at least one temperature sensor(s) and/or at least one humidity sensor(s), preferably both, are located in at least one effective location(s) and height(s) within the treated room(s) and/or targeted area(s) (30), and another at least one temperature sensor(s) and/or at least one humidity sensor(s), preferably both, are located in at least another different effective location(s) and height(s) within the treated room(s) and/or targeted area(s) (30).

Also, and referring to FIGS. 6-8 it is more preferred, without limitation, that at least one environmental sensor(s) (130, 132) that includes the at least one temperature sensor(s) and the at least one humidity sensor(s), is located at any effective distance, near, from, in relation to, and/or within any effective proximity to, the ceiling (145) of the treated room(s) and/or targeted area(s) (30), as denoted by the letter "C", and another at least one environmental sensor(s) (130, 132) that includes the at least one temperature sensor(s) and the at least one humidity sensor(s), is located at any effective distance, near, from, in relation to, and/or within any effective proximity to, the floor(s) (95) of the treated room(s) and/or targeted area(s) (30), as denoted by the letter "F".

It is also preferred, without limitation, that the various environmental sensor(s) (130, 132), preferably two or more, as denoted by Letter "C" and Letter "F", are suitably and effectively, located, mounted, and/or connected, to one or more of any effective means to hold, position, connect, and/or mount, the various environmental sensor(s) (130), such as, but not limited to, one or more of any tripod(s), feet(s), pole(s), support pole(s), hanging apparatus(s), support mechanism(s), stand(s), and/or support stand(s) (Herein called "Mounting Stand(s)") (135). Without being limited, one or more environmental sensor(s) (130, 132) can, without limitation, be located on or attached, at one or more of any height(s) and/or location(s), to one or more of any mounting stand(s) (135). Without being limited, the various environmental sensors (130, 132) can be located at any effective distance(s), either vertically and/or horizontally from each other, preferably any distance(s) that is at least effective.

Without being limited, the one or more environmental sensor(s) (130, 132) can be located at any distance(s), preferably that is effective, from the ceiling(s) (145) of the treated room(s) and/or targeted area(s) (30). It is preferred, without limitation that the environmental sensor(s) (130, 132) are located between about 0.25 to eighty inches or more, from the ceiling(s) (145). It is more preferred, without limitation, that the environmental sensor(s) (130, 132) are located between about one to sixty inches from the ceiling(s) (145). In addition, the one or more environmental sensor(s) (130, 132) can also, without limitation, be located in various locations or areas including, but not limited to, near or approximate to any, floor(s), lowest area(s), or lowest surface(s) in the treated room(s) and/or targeted area(s) (30) (Herein called "Floors") (95), within one or more space(s) or area(s) where the aerosol (40) is deployed. Without being limited, the one or more environmental sensor(s) (130, 132) can also be located at any distance(s), preferably that is effective, from the floor(s) (95). It is preferred, without limitation, that the environmental sensor(s) (130, 132) are located between about 0.25 to sixty inches or more from the floor (95). It is even more preferred that the environmental sensor(s) (130, 132) are located between about one to fifty inches from the floor (95).

It is also preferred, without limitation, that one or more of the environmental sensor(s) (130, 132) is located as effectively and/or possibly close to the highest point(s) or ceiling(s) (145) of the treated room(s) and/or targeted area(s) (30). Without being limited, one or more additional environmental sensor(s) (130, 132) can also be located and simultaneously operated at any other suitable and effective height(s) and location(s) within the treated room(s) and/or targeted area(s) (30). It is even more preferred, that if more than one environmental sensor(s) (130, 132) is attached or directly or indirectly connected to, the same mounting stand(s) (135), at least one of these environmental sensor(s) (130, 132) is located as effectively and/or possibly close to the highest point(s) or ceiling(s) (145) of the treated room(s) and/or targeted area(s) (30), and at least one of another environmental sensor(s) (130, 132) is located as effectively and/or possibly close to the lowest point(s) or floor(s) (95) of the treated room(s) and/or targeted area(s) (30).

Referring to FIG. 6-8, and without limitation, the environmental sensor(s) (130, 132) can report or indicate the presence and/or absence, of one or more of any layers of air/gas(s) and/or deployed aerosol(s) (40) that can be present within the treated room(s) and/or targeted area(s) (30).

Referring to FIG. 6, and without limitation, this figure shows a targeted area(s) (30) before the aerosol (40) is deployed and the room is treated. More specifically, at least one layer of air/gas is denoted by the term "L1", having one or more of any characteristics such as, but not limited to any, temperature, humidity, and/or or thickness, and it is located near and/or at the top of the targeted area(s) (30). At least another one layer of air/gas is denoted by the term "L2", having one or more of any characteristics such as, but not limited to any, temperature, humidity, and/or or thickness, and it is located near and/or close to the bottom of the targeted area(s) (30) and/or floor(s) (95).

Without being limited, in this situation, the various environmental sensor(s) (130, 132) reports or shows a difference and/or a significant difference for temperature, and/or humidity, for one or more of the various environmental sensor(s) (130, 132) located near the floor (95) as denoted by the letter(s) "F", and one or more of the various environmental sensor(s) (130, 132) located near the ceiling (145) as denoted by the letter(s) "C". It is preferred, without limitation, that to confirm the presence of at least one layer(s) of any air/gas(s) and/or aerosol(s) in this situation, at least a difference, but preferably a significant difference, exists for at least some, but preferably all, data reported by all the various environmental sensor(s) (130, 132) denoted by the letter "F" and all of the data reported by all the various environmental sensor(s) (130, 132) denoted by the letter "C".

Referring to FIG. 7, and without limitation, this figure shows the treated room(s) and/or targeted area(s) (30) after any amount of aerosol (40) has been is deployed, preferably at least after a quarter of the time had elapsed for an aerosol (40) deployment cycle that was determined for an effective room treatment. More specifically, at least one layer of air/gas is denoted by the term "L3", having characteristics such as any, temperature, humidity, and/or or thickness, and it is located near, in proximity to, and/or at the top, of the targeted area(s) (30). At least one layer of deployed aerosol (40) is denoted by the term "L4", having characteristics such as any, temperature, humidity, and/or or thickness, and it is located near, in proximity to, and/or close to, the bottom of the targeted area(s) (30) and/or floor(s) (95).

Without being limited, in this situation, the various environmental sensor(s) (130, 132) reports or shows a difference and/or a significant difference for temperature, and/or humidity, for one or more of the various environmental sensor(s) (130, 132) located near the floor (95) as denoted by the letter "F", and the one or more of the various environmental sensor(s) (130, 132) located near the ceiling (145) as denoted by the letter "C". It is preferred, without limitation, that to confirm the presence of at least one layer(s) of any air/gas(s) and/or aerosol(s) in this situation, at least a difference, but preferably a significant difference, exists for at least some, but preferably all, data reported by all the various environmental sensor(s) (130, 132) denoted by the letter "F" and all of the data reported by all the various environmental sensor(s) (130, 132) denoted by the letter "C".

Referring to FIG. 8, and without limitation, this figure shows the treated room(s) and/or targeted area(s) (30) after the aerosol (40) has been effectively deployed, and the aerosol (40) is evenly dispersed, effectively mixed together with the other parts of the atmosphere within the targeted area(s) (30), completely dispersed, and/or completely homogenized, within the targeted area(s) (30), and at least no layers that can have any significant effect on the efficacy of the room treatment, and preferably no layer(s) at all, of any air/gas(s) and/or aerosol (40) are present.

Without being limited, in this situation, the various environmental sensor(s) (130, 132) do not report or show a difference and/or a significant difference for temperature and/or humidity, for the various environmental sensor(s) (130, 132) located near the floor (95) as denoted by the letter "F", and one or more of the various environmental sensor(s) (130, 132) located near the ceiling (145) as denoted by the letter "C". It is preferred, without limitation, that to confirm the absence of any layer(s) of any air/gas(s) and/or aerosol(s) in this situation, no significant differences exists for at least most, but preferably all, data reported by all the environmental sensor(s) (130, 132) denoted by the letter "F" and all of the data reported by all the environmental sensor(s) (130, 132) denoted by the letter "C".

With reference to FIGS. 6-8 and according to an embodiment, and without limitation, the atmospheric humidity and/or any humidity level, within the room(s) and/or targeted area(s) (30) before or during the deployment of the aerosol (40) can adversely effect the effectiveness of the treatment process within the targeted area(s) (30), in ways such as, but not limited to, "low humidity" levels or humidity that is below an effective value and/or effective range, can extend the needed time that is necessary to achieve any effective and/or efficacious deployment of the aerosol (40) into the treated room(s) and/or targeted area(s) (30) and/or the treatment of these space(s) and the various surface(s) within these space(s). Without being limited, this can be encountered in situations such as, but not limited to, the cold winter months when room(s) or space(s) in facilities, like hospitals, can be drier than in the summer months.

Without being limited, this issue can be overcome by performing the following activities to pre-treat the targeted area(s) (30) before they are completely treated, officially treated, and/or all of the process steps are taken to effectively treat and/or decontaminate the targeted area(s) (30), and increase the relative humidity level(s) to at least an effective value(s) and/or within an effective range of value(s), before the main or primary and/or originally intended treatment process for a given volume occurs, such as, but not limited to: (1) Sensing the temperature and/or humidity within the targeted area(s) (30) with one or more of any environmental sensor(s) (130, 132), located at one or more of any location(s) within the targeted area(s) (30), (2) Deploying any effective amount of aerosol into the targeted area for any effective duration of time, (3) (Optionally) Operating the one or more of any downward facing fan(s) (90), at one or more of any effective location(s), for any effective duration of time, to effectively mix and/or effectively distribute the deployed aerosol (40) and resultant humidity, into the air or atmosphere within the targeted area(s) (30). Without being limited, these activities when performed before starting the main or primary process cycle, including the main or primary aerosol deployment cycle, after any pre-treatment of the room with any aerosol deployment into the targeted area(s) (30), has been shown to offer advantages such as, but not limited to, increasing the effectiveness of the deployment of the aerosol (40) and the treatment process, as well as decreasing the time to effectively complete the entire treatment cycle or process.

With reference to FIGS. 6-8, and according to an embodiment, and without limitation, to detect and/or confirm the presence of at least one or more layer(s) of any, air/gas(s) (166) and/or aerosol(s) (167), within the targeted area(s) (30), at least a difference, but preferably a significant difference, exists for at least some, but preferably all, air/gas(s) temperature data reported by all of the various environmental sensor(s) (130, 132) such as, but not limited to, the data reported by at least one, but preferably all, of the various environmental sensor(s) (130) denoted by the letter "F", and the data reported by at least one, but preferably all, of the various environmental sensor(s) (132) denoted by the letter "C", where it is preferred, without limitation, that the temperature difference(s) between environmental sensor(s) (130) or those denoted by the letter "F", and environmental sensor(s) (132) or those denoted by the letters "C", to indicate the presence of one or more of any air/gas(s) layer(s) (166) and/or aerosol (40) layer(s) (167) is preferably between about zero to 25 degree Fahrenheit or more, more preferably between about zero to 15 degree Fahrenheit, even more preferably between about zero to 10 degree Fahrenheit, very preferably between about 0.1 to 8 degree Fahrenheit, and extremely preferably between about zero to 5 degree Fahrenheit.

Also, with reference to FIG. 7, and according to an embodiment, and without limitation, the relative humidity(s) and/or temperature(s) in one or more of any location(s) within the one or more treated space(s) or targeted area(s) (30) such as, but not limited to, the one or more of any layer(s) of deployed aerosol (40) or aerosol layer(s) (167), as well as the one or more of any layer(s) of any air/gas(s) (166), can have any temperature(s) and/or relative humidity(s) or relative humidity value(s), and preferably a relative humidity value and/or temperature that is at least effective. Without being limited, it is preferred, that the relative humidity or relative humidity value that is recorded in one or more of any layer(s) of deployed aerosol (40) or aerosol layer(s) (167), at one or more of any location(s), is at least between about 40 to 100 percent, and more preferably between about 75 to 100 percent, and even more preferably at least 80 percent or more.

In addition, and without limitation, the relative humidity or relative humidity value that is recorded in one or or more of any location(s) in the one or more of any air/gas layer(s) (166) that can be located at one or more of any location(s) above the deployed aerosol (40) or aerosol layer(s) (167) is at least effective, and more preferably between about 3 to 100 percent, and even more preferably between about 30 to 100 percent, and very preferably at least 30 percent or more, and extremely preferably between about 50 to 100 percent.

With reference to FIGS. 6-8, and according to an embodiment, and without limitation, to detect and/or confirm the presence of at least one or more layer(s) of any, air/gas(s) (166) and/or aerosol(s) (167), within the targeted area(s) (30), at least a difference, but preferably a significant difference, exists for at least some, but preferably all, humidity data reported by all of the various environmental sensor(s) (130, 132) such as, but not limited to, the data reported by at least one, but preferably all, of the various environmental sensor(s) (130) denoted by the letter "F", and the data reported by at least one, but preferably all, of the various environmental sensor(s) (132) denoted by the letter "C", where it is preferred, without limitation, that the humidity and/or relative humidity difference(s) between environmental sensor(s) (130) or those denoted by the letter "F", and environmental sensor(s) (132) or those denoted by the letters "C", to indicate the presence of one or more of any air/gas(s) layer(s) (166) and/or aerosol (40) layer(s) (167) is preferably at least between about zero to 100 percent, more preferably between about 0.01 to 100 percent, even more preferably between about 0.01 to 99 percent, and very preferably between about 1 to 99 percent, and extremely preferably between about 10 to 90 percent.

With reference to FIGS. 6-7, and according to an embodiment, and without limitation, the humidity can also be equivalent, close to equivalent, close, and/or significantly close to the same values, for both: (a) air/gas layer(s) (166), and/or (b) the one or more of any layer(s) of deployed aerosol (40) or aerosol layer(s) (167) within the treated or targeted area(s) (30) and the one or more of any air/gas layer(s) (166), where only one or more of any air/gas(s) temperature difference(s) detected in the treated or targeted area(s) (30), may indicate the presence of one or more of any layer(s) of deployed aerosol (40) or aerosol layer(s) (167) and/or one or more of any air/gas layer(s) (166).

With reference to FIGS. 6-7, and according to an embodiment, and without limitation, the air/gas(s) temperature values can also be equivalent, close to equivalent, close, and/or significantly close to the same values, for both: (a) air/gas layer(s) (166), and/or (b) the one or more of any layer(s) of deployed aerosol (40) or aerosol layer(s) (167) within the treated or targeted area(s) (30) and the one or more of any air/gas layer(s) (166), where only one or more of any humidity difference(s) detected in the treated or targeted area(s) (30), may indicate the presence of one or more of any layer(s) of deployed aerosol (40) or aerosol layer(s) (167) and/or one or more of any air/gas layer(s) (166).

With reference to FIG. 8, and according to an embodiment, and without limitation, to detect and/or confirm an effective, even dispersion and/or homogeneous mixing, of the deployed aerosol (40) within the treated or targeted area(s) (30), and the absence of the one or more layer(s) of any, air/gas(s) (166) and/or aerosol(s) (167), within the targeted area(s) (30), preferably no difference(s) or at least no significant difference(s), exists for preferably most, more preferably a majority, and even more preferably all, temperature and/or humidity data reported by all of the various environmental sensor(s) (130, 132) such as, but not limited to, the data reported by at least one, but preferably all, of the various environmental sensor(s) (130) denoted by the letter "F", and the data reported by at least one, but preferably all, of the various environmental sensor(s) (132) denoted by the letter "C". Without being limited, FIG. 8 represents the preferred outcome after effectively deploying the aerosol (40) into the one or more of any targeted area(s) or treated space(s) (30), where the deployed aerosol (40) is effectively dispersed, evenly dispersed, equally dispersed, and/or homogenized, throughout the targeted area(s) or treated space(s) (30).

Also referring to FIG. 8, and without being limited, it is preferred that the relative humidity or relative humidity value that is recorded in one or or more of any location(s) in the deployed aerosol (40) that has effectively and completely filled the one or more of any targeted area(s) or treated space(s) (30), is at least effective, and more preferably is between about 50 to 100 percent, and even more preferably is between about 70 to 100 percent, and very preferably is at least 80 percent or more, and extremely preferably is between about 90 to 100 percent.

With reference to FIG. 7-8, and according to an embodiment, and without limitation, the formation or presence of one or more of any layer(s) (167) of deployed aerosol (40), or any stratification of the deployed aerosol (40), within the one or more of any targeted area(s) or treated space(s) (30), can occur for one or more of any reason(s) including, but not limited to: (a) the deployed aerosol (40) is colder than the atmosphere within the targeted area(s) or treated space(s) (30), and/or (b) the presence or creation of one or more of any temperature gradient(s) and/or layer(s) or pocket(s) of any air/gas(s) (166) within the targeted area(s) or treated space(s) (30), having one or more of any temperature(s) to create said gradient(s) and/or layer(s) (166), that are typically located at one or more of any location(s) or distance(s) above and/or below, but typically above, the one or more layer(s) of the deployed aerosol (167).

Without being limited, the stratification of the aerosol (40) within the targeted area(s) or treated space(s) (30), forming one or more of any layer(s) of the deployed aerosol (167) within the targeted area(s) or treated space(s) (30), can have at least one temperature gradient(s) and/or at least one temperature difference(s), and preferably a significant difference, in air/gas temperatures when comparing temperatures such as, but not limited to, the air/gas temperature within the layer of the deployed aerosol (167) and the temperature of the air/gas layer(s) (166) that is located above the one or more layer(s) of the deployed aerosol (167).

Also without being limited, the stratification of the aerosol (40) within the targeted area(s) or treated space(s) (30), forming one or more of any layer(s) of the deployed aerosol (167) within the targeted area(s) or treated space(s) (30), can be effectively, reduced, eliminated, and/or mitigated, if the atmosphere or air/gas(s) within the targeted area(s) or treated space(s) (30) is effectively stirred, mixed, and/or homogenized, before the deployment of aerosol (40) into the targeted area(s) or treated space(s) (30), with one or more of any effective source(s) of pressurized air, for any effective amount of time, and preferably with one or more of any effective downward facing fan(s) (90).

However, and without being limited, sometimes the stratification or formation of one or more layer(s) (167) of the deployed aerosol (40) may still happen within the targeted area(s) or treated space(s) (30) after the air/gas(s) or atmosphere within that space has been effectively stirred, mixed, and/or homogenized, before the deployment of the aerosol (40), and the stratification of the deployed aerosol (40) can be effectively, reduced, eliminated, and/or mitigated, if the atmosphere or air/gas(s) within the targeted area(s) or treated space(s) (30) is effectively stirred, mixed, and/or homogenized, with one or more of any effective source(s) of pressurized air, for any effective amount of time, and with any effective velocity, and preferably with one or more of any effective downward facing fan(s) (90).

It is also preferred, without limitation, that the one or more of any effective source(s) of pressurized air and/or the downward facing fan(s) (90), is effectively located within the one or more layer(s) (167) of the deployed aerosol (40), and more preferably effectively located near and/or above the floor (95) of the targeted area(s) or treated space(s) (30). Without being limited, the air/gas(s) and aerosol (40) can be moved in one or more of any directions and angles, preferably that are at least effective, by the one or more of any effective source(s) of pressurized air and/or the downward facing fan(s) (90).

Without being limited, the one or more of any effective source(s) of pressurized air and/or the downward facing fan(s) (90) can also preferably move any effective amount or volume of air/gas(s) and aerosol (40) to one or more of any location(s) such as, but not limited to, initially across the floor (95), at any effective velocity, where the air/gas(s) and aerosol (40) that is moved, can then continue to move up and away from the floor (95) or be channeled up and away from the floor (95) and along the one or more of any effective vertical and/or angled surfaces, whereby the air/gas(s) and aerosol (40) that is moved by the one or more source(s) of pressurized air, and/or the downward facing fan(s) (90), is effectively moved or located to one or more of any effective location(s) above the stratified aerosol (40) or the one or more of any layer(s) of the deployed aerosol (167), including but not limited to, one or more of any location(s) at or effectively near the ceiling(s) of the targeted area(s) or treated space(s) (30), but at least effectively above the one or more layers (167) of the deployed aerosol (40). Without being limited, the aerosol (40) and air/gas(s) that is moved to the one or more of any location(s) above the stratified aerosol (40) or the one or more of any layer(s) (167) of the deployed aerosol (40), can then move freely into and effectively fill any other parts or locations of the targeted area(s) or treated space(s) (30). Also, and without being limited, the aerosol (40) and air/gas(s) that is moved or located to the one or more of any location(s) above the stratified aerosol (40) or the one or more of any layer(s) (167) of the deployed aerosol (40), can also help to effectively, mix, equalize, and/or homogenize, conditions or things such as, but not limited to, the temperature, the humidity, and/or the deployed aerosol (40), within the targeted area(s) or treated space(s) (30).

Without being limited, the movement of the air/gas(s) and deployed aerosol (40) effectively above the one or more layer(s) (167) of the deployed aerosol (40) or the one or more stratified layers (167) of deployed aerosol (40), can assist in the effective treatment of the targeted area(s) or treated space(s) (30) in ways including, but not limited to, (a) enabling and/or accelerating the effective, dispersion, full dispersion, homogenization, and/or movement, of the deployed aerosol (40) within and/or throughout the targeted area(s) or treated space(s) (30), and (b) effectively, reducing, eliminating, and/or mitigating, any temperature and/or humidity gradients that may be located within the targeted area(s) or treated space(s) (30).

With reference to FIG. 1, FIGS. 3-4, FIGS. 6-8, and FIGS. 9-12, and according to an embodiment, and without limitation, the following process(s) or step(s) is an example of using the present invention to improve the art for the effective disinfection and/or decontamination of one or more targeted area(s) (30) using any deployed aerosol(s) (40):

(1) The operator locates one or more of any aerosol generator apparatus(s) (1), into the one or more targeted area(s) (30).

(2) The operator powers the aerosol generator apparatus(s) (1) and activates it.

(3) The operator enters into any software, that controls the one or more aerosol generator apparatus(s) (1), various information and data such as, but not limited to, the one or more volume(s) of the one or more targeted area(s) (30). It is preferred, without limitation, that the one or more data or value(s) for the volume(s) of the targeted area(s) (30), is entered by any employee(s) and/or machine operator(s) at any effective time. In addition, and without limitation, this volume information or data can also be previously entered into any suitable database, software, and/or program, and be tied in a manner known to those skilled in the art, to any alphanumeric or any other descriptive value that is tied to any particular treated space(s), such as, but not limited to, any room number(s) or room name(s). This can allow, without limitation, the machine operator(s) to enter the room number(s) or room name(s) into any human machine interface (HMI) and/or software, and the one or more system control algorithms and/or software can be preprogrammed to begin one or more of any effective treatment operation(s) and/or sequence(s) of operation event(s) for that particular space or room, based on the entered data and the preprogrammed information such as, but not limited to, any pre-programmed volume value(s) for the targeted area(s) (30).

4) Various environmental sensor(s) (130, 132) collect and report data for environmental conditions in the one or more targeted area(s) (30) such as, but not limited to any, temperature, and/or relative humidity data. This data is then reported to any software that controls the one or more of any aerosol generating apparatus(s) (1).

5) One or more of any effective software, software function(s), and/or algorithm(s) can be used, preferably and without limitation, with any microprocessor based controller (22), to determine and/or establish various operational parameters for the various treatment cycle(s) (given various input(s) or data), and especially the primary or main treatment cycle, to carry out, such as, but not limited to any:

(a) The aerosol deployment time is calculated, and/or any effective amount or volume of liquid disinfectant (45) to deploy as an aerosol (40) into a given volume of the targeted area(s) (30), for any effective outcome or treatment, is determined and/or calculated, and the deployment time necessary to effectively deploy the liquid as an aerosol (40) is also determined and/or calculated, considering variables and data such as, but not limited to any, (i) volume of the treated area(s) (30), (ii) one or more relative humidity(s) level(s) in the targeted area(s) (30), (iii) one or more temperature(s) in the targeted area(s) (30).

Without being limited, in "warmer" atmospheric conditions within the targeted area(s) (30), where the atmospheric temperature is above ambient conditions of 72 degree Fahrenheit, "more" aerosol (40) and liquid (45) may be needed to effectively treat the targeted area(s) (30), and "less" aerosol (40) and liquid (15) may be needed to effectively treat the targeted area(s) (30) when the atmospheric temperature is below ambient conditions of 72 degree Fahrenheit. Also, without being limited, in "drier" atmospheric conditions within the targeted area(s) (30), when the atmospheric humidity level is below ambient conditions, "more" aerosol (40) and liquid (45) may be needed to effectively treat the targeted area(s) (30), and "less" aerosol (40) and liquid (45) may be needed to effectively treat the targeted area(s) (30) when the atmospheric humidity level is above ambient conditions.

(b) Any pre-treatment for the one or more targeted area(s) (30) that may be needed, with any effective quantity of aerosol (40) or effective aerosol (40) deployment time, including any use of the downward facing fan(s) (90) and/or blower(s) (85), to increase the humidity level(s) in the targeted area(s) (30) so that they are at least effective before the main or primary treatment cycle begins for the treatment of the targeted area(s) (30).

c) Any pre-conditioning of the one or more targeted area(s) (30) that may be needed, using one or more downward facing fan(s) (90) and/or blower(s) (85), to effectively stir and/or mix together the air/gas(s) and/or atmosphere within the targeted area(s) (30), to effectively mix, disrupt, and/or eliminate, one or more of any layer(s) of any air/gas(s) and/or atmosphere within the targeted area(s) (30), and allow full and complete movement of the deployed aerosol(s) throughout the targeted area(s).

(d) Any one or more of any breaks that may be needed during the aerosol (40) deployment, to effectively stir and/or mix together the air/gas(s) and/or deployed aerosol(s) (40) within the targeted area(s) with the at least one or more of any downward facing fan(s) (90) and/or blower(s) (85), where any effective duration of time for the stirring and/or mixing can be used at any time. Without being limited, the deployment of any aerosol (40) from the aerosol generating apparatus (1) can also be stopped or not stopped, when the downward facing fan(s) (90) and/or blower(s) (85) are operating during the main or primary treatment cycle and deployment of the aerosol (40) into the targeted area(s) (30).

(e) The dwell time, after the deployment of all of the aerosol (40) at the end of the main or primary deployment cycle of the aerosol (40), to give the deployed aerosol (40) any effective amount of time to efficaciously contact and/or treat the various surfaces and/or atmosphere within the targeted area(s) (30). The dwell time can be any effective amount of time.

(f) The operation time for the one or more of any dehumidification apparatus(s) (80) after the room treatment cycle is complete, and after the Dwell Time is completed. The dehumidification time can be any effective amount of time. Without limitation, the dehumidification apparatus(s) (80) can also operate until it is shut down by the operator, and/or the system shuts down automatically after any effective or desired amount of time has elapsed.

(g) The operation time for the one or more of any activated carbon filter(s) (120) after the room treatment cycle is complete, and after the Dwell Time is completed. The activated carbon filter(s) (120) can operate at any time. It is preferred, without limitation, that the activated carbon filter(s) (120) are not operated until the humidity in the targeted area(s) is reduced to at least 90 percent or less. The activated carbon filter(s) (120) can be used or operated for any effective amount of time. Without limitation, the activated carbon filter(s) (120) can also operate until it is shut down by the operator, and/or the system shuts down automatically after any effective or desired amount of time has elapsed.

6) The operation of the treatment cycle for the one or more aerosol generating apparatus(s) (1) is started.

7) Various environmental sensor(s) (130, 132) collect and continuously report more data for environmental conditions in the one or more targeted area(s) (30) such as, but not limited to any, temperature, and/or relative humidity data. This data is then reported to any software that controls the one or more of any aerosol generating apparatus(s) (1). The various environmental sensor(s) (130, 132) can report any data to the one or more aerosol generating apparatus(s) (1) and/or any supporting or control software, at any time.

8) If the reported data from the various environmental sensor(s) (130, 132) shows a relative humidity that is not effective and/or not within an effective range before aerosol deployment, within the targeted area(s) (30), it is preferred, without limitation, that the aerosol generating apparatus(s) (1) deploys aerosol (40) for any effective quantity of aerosol (40) and amount of time, to at least raise the humidity in the targeted area(s) to any effective point or level and/or to or within any effective range, to pre-treat the targeted area(s) (30) before the main or primary treatment cycle begins for the targeted area(s) (30). The one or more downward facing fan(s) (90) and/or blower(s) (85) can also be, without limitation, operated after and/or during the deployment of the pre-treatment aerosol (40) for any effective duration of time, in order to effectively stir and/or mix together the air/gas(s) and/or atmosphere within the targeted area(s) and effectively distribute the humidified air/gas(s).

9) Referring to FIG. 6, and without being limited, if the reported data from the various environmental sensor(s) (130, 132) in the targeted area(s) (30) before aerosol deployment, shows any difference(s) and/or significant difference(s), between the various temperature and/or humidity data that is reported, indicating one or more of any layer(s) of air/gas(s) is present within the targeted area(s) (30), then the one or more downward facing fan(s) (90) and/or blower(s) (85) can be operated for any effective duration of time, in order to effectively stir and/or effectively mix together the air/gas(s) within the targeted area(s) (30) in order to effectively disrupt, mix, and/or eliminate, any layer(s) of any air/gas(s) within the targeted area(s), in preparation for an effective deployment of the aerosol (40), and treatment of the targeted area(s) (30).

10) Aerosol deployment begins.

11) During deployment of the aerosol (40), various environmental sensor(s) (130, 132) continue to collect and report data for environmental conditions in the one or more targeted area(s) (30) such as, but not limited to any, temperature, and/or relative humidity data. This data is reported to any software that controls the one or more of any aerosol generating apparatus(s) (1). Without being limited, the various environmental sensor(s) (130, 132) can report data to the aerosol generating apparatus (1), and/or more specifically, any microprocessor based controller (22) and/or any associated system software, at one or more of any effective time(s).

12) Referring to FIG. 7, and without being limited, if the reported data from the various environmental sensor(s) (130, 132) in the targeted area(s) (30) during aerosol deployment, shows any difference(s) or significant difference(s), between the various temperature and/or humidity data that is reported, indicating one or more of any layer(s) of air/gas(s) and/or any one or more of any layer(s) of deployed aerosol (40), is present within the targeted area(s) (30) at any time during the deployment of the aerosol (40), then the one or more downward facing fan(s) (90) and/or blower(s) (85) can be operated at any effective time, and for any effective duration of time, in order to effectively stir and/or effectively mix together the air/gas(s) within the targeted area(s) (30) in order to effectively disrupt and/or eliminate any layer(s) of any air/gas(s) and/or aerosol(s) (40) within the targeted area(s), and allow or assist the aerosol (40) to interact with all of the targeted surfaces within the targeted area(s) (30).

Without being limited, the blower(s) and/or downward facing fan(s) (90) can be operated multiple times, for any effective time or duration(s) of time, and at any effective time(s), while the aerosol (40) is deployed into the targeted area(s) (30) and/or during any part of the main or primary treatment cycle. However, it is preferred, without limited, that if the operation of the blower(s) (85) and/or the downward facing fan(s) (90) is needed, they are preferably operated at least once, starting between about 0.1-99 percent of the way through to the completion of the aerosol deployment time, more preferably operated at least once, starting between about 5-90 percent of the way through to the completion of the aerosol deployment time, even more preferably operated at least once, starting between about 25-87 percent of the way through to the completion of the aerosol deployment time, even more preferably operated at least once, starting between about 30-87 percent of the way through to the completion of the aerosol deployment time.

Alternatively, and without being limited, the downward facing fan(s) (90) and/or blower(s) (85) can be preferably operated at least once, after the treated room(s) and/or targeted area(s) (30) have been at least effectively filled with the deployed aerosol (40). It is preferred, without limitation, that if the operation of the downward facing fan(s) (90) and/or blower(s) (85) is needed and/or desired, they can be operated at least once, after the treated room(s) and/or targeted area(s) (30) have been filled between about 0.1 to 100 percent full with the deployed aerosol (40). It is more preferred, without limitation, that if the operation of the downward facing fan(s) (90) and/or blower(s) (85) is needed and/or desired, they can be operated at least once, after the treated room(s) and/or targeted area(s) (30) have been filled between about 1 to 99.9 percent full with the deployed aerosol (40). It is even more preferred, without limitation, that if the operation of the downward facing fan(s) (90) and/or blower(s) (85) is needed and/or desired, they can be operated at least once, after the treated room(s) and/or targeted area(s) (30) have been filled between about 5 to 95 percent full with the deployed aerosol (40). It is very preferred, without limitation, that if the operation of the downward facing fan(s) (90) and/or blower(s) (85) is needed and/or desired, they can be operated at least once, after the treated room(s) and/or targeted area(s) (30) have been filled between about 30 to 95 percent full with the deployed aerosol (40). It is extremely preferred, without limitation, that if the operation of the downward facing fan(s) (90) and/or blower(s) (85) is needed and/or desired, they can be operated at least once, after the treated room(s) and/or targeted area(s) (30) have been filled between about 50 to 90 percent full with the deployed aerosol (40).

Also, and without limitation, the deployment of the aerosol (40) can also temporarily stop at any effective time(s) and for any effective duration(s), while the downward facing fan(s) are operating. It is preferred, without limitation, that the downward facing fan(s) (90) and/or blower(s) (85) operate during the deployment of the aerosol(s) (40), when they are needed to stir or mix the air/gas(s) or atmosphere within the targeted area(s) (40) for any effective outcome.

13) Referring to FIG. 8, and without being limited, if the aerosol (40) deployment is complete and/or the aerosol (40) deployment for the main or primary treatment cycle for the targeted area(s) (30) is complete, the reported data from the various environmental sensor(s) (130, 132) in the targeted area(s) (30), should preferably and without limitation, show no difference(s) or no significant difference(s), between the various temperature and/or humidity data that is reported, indicating that there are no layer(s) of air/gas(s) and/or one or more of any layer(s) of deployed aerosol (40), and/or or at least no significant layer(s) of air/gas(s) and/or one or more of any layer(s) of deployed aerosol (40), that can degrade the effectiveness of the aerosol (40) and/or the effectiveness of the treatment of the targeted area(s) by the deployment of the aerosol (40).

However, if the aerosol (40) deployment is complete and/or the aerosol (40) deployment for the main or primary treatment cycle for the targeted area(s) (30) is complete, and the reported data from the various environmental sensor(s) (130, 132) in the targeted area(s) (30), shows any difference(s) or significant difference(s), between the various temperature and/or humidity data that is reported, indicating one or more of any layer(s) of air/gas(s) and/or one or more of any layer(s) of deployed aerosol (40), is present within the targeted area(s) (30), then any effective additional amount of aerosol (40) can be deployed into the targeted area(s) (30) and/or the downward facing fan(s) (90) and/or blower(s) (85) can be operated one or more additional times, for any effective amount of time, until the aerosol (40) that is deployed is effectively distributed or dispersed within the targeted area(s) (30).

14) The aerosol deployment stops.

15) The dehumidification process starts and dehumidifies the atmosphere or space(s) within the targeted area(s) (30) to any desired or effective humidity level, point, data point, and/or range.

16) The atmosphere or space within the targeted area(s) (30) is filtered with one or more of any effective means to filter and remove any targeted substance(s), such as, but not limited to any vapor(s), from the air/gas(s) within the targeted area(s) (30), all in a manner known to those skilled in the art.

17) The dehumidification and the filtration of the air/gas(s) within the targeted area(s) stops.

With reference to FIGS. 13-19, and according to an embodiment, and without limitation, the one or more of any suitable and effective downward facing fan(s) (90) can also be located and positioned at one or more of any location(s) such as, but not limited to, those that are, at, approximate to, close to, directly and/or indirectly connected to, on, outside of, and/or near, one or more of any side(s) of any aerosol generating apparatus(s) (01). It is preferred, without limitation, that one or more of any suitable and effective downward facing fan(s) (90) are suitably and effectively positioned and located at one or more of any suitable and effective location(s) that are directly and/or indirectly connected and/or interfaced, at, to, and/or near, the exterior of any one or more of any suitable and effective side(s) of any aerosol generating apparatus(s) (01). Without being limited, the downward facing fan(s) (90) can be, located, positioned, connected and/or interfaced, with and/or at, one or more, but preferably, and without limitation, at least two side(s), of the aerosol generating apparatus(s) (90).

Without being limited, once the downward facing fan(s) (90) are suitably and effectively, extended, deployed, and/or positioned, to any suitable and effective, distance(s), location(s), and/or position(s), the downward facing fan(s) (90) can suitably and effectively operate at any suitable and effective time(s), and for any suitable and effective duration(s) of time(s).

The one or more of any downward facing fan(s) (90) can be located at one or more of any height(s) and/or angle(s), but is preferred, without limitation, that the downward facing fan(s) (90) are at least located and positioned at any suitable and effective distance(s) from the floor(s) (95) of the treated room(s) and/or targeted area(s) (30). It is also preferred, without limitation, that the downward facing fan(s) (90) are effectively angled downward toward the floor(s) (95) of the treated room(s) and/or targeted area(s) (30). It is more preferred, without limitation, that the output of the downward facing fan(s) (90) are effectively angled directly and/or about directly downward toward the floor(s) (95) of the treated room(s) and/or targeted area(s) (30).

Without being limited, the downward facing fan(s) (90) can be positioned, located, connected, and/or interfaced, with and/or at, one or more of any side(s) and/or outside of one or more of any side(s), of the aerosol generating apparatus(s) (90), in any suitable and effective manner known to those skilled in the art.

Also, and without being limited, the downward facing fan(s) (90) can be connected and/or interfaced with one or more of any means known to those skilled in the art, to allow or enable the downward facing fan(s) (90) to pivot, slide, and/or move, in any suitable and effective angle(s) and/or direction(s), such as, but not limited to any, hinge(s), ball joint(s), gimbal(s), and/or joint(s) (Herein called "Pivot Mechanism(s)") (180). It is preferred, without limitation, that the downward facing fan(s) (90) are directly and/or indirectly mounted and/or connected to the aerosol generating apparatus(s) (90) with one or more of any suitable and effective Pivot Mechanism(s)") (180). It is also preferred, without limitation, that the downward facing fan(s) (90) can move in any effective direction(s) such as, but not limited to, up, down, and/or across, when connected to the Pivot Mechanism(s)") (180). Also, and without being limited, the downward facing fan(s) (90) can be moved into one or more of any suitable and effective location(s) and/or position(s), either manually and/or automatically, via any suitable and effective mechanical and/or automated means known to those skilled in the art, at any suitable and effective time(s). Without being limited, the downward facing fan(s) (90) can also be held, supported, and/or maintained, in any suitable and effective location(s), angle(s), and/or position(s), at any suitable and effective time(s), and for any suitable and effective duration of time(s), with one or more of any suitable and effective, part(s), design(s), and/or means, all in a manner known to those skilled in the art.

Without being limited, any means known to those skilled in the art, such as, but not limited to any, releasable position locking apparatus(s) (185), can be used to connect and/or releasably connect to or with the downward facing fan(s) (90) and/or any other part(s) that are directly and/or indirectly connected to the downward facing fan(s) (90), to hold and/or support the downward facing fan(s) (90) in any suitable and effective orientation(s), position(s), and/or direction(s), such as, but not limited to any, upward, downward, and/or horizontal, orientation(s), position(s), and/or direction(s), for various uses and purposes including, but not limited to any, storage purposes, and/or for assisting in the effective operation of the downward facing fan(s) (90) including, but not limited to, maintaining the position(s) and location(s) of the downward facing fan(s) (90) during their operation. It is preferred, without limitation, that the releasable position locking apparatus(s) (185), includes various part(s) such as, but not limited to one or more of any, holding member mount point(s) (190), holding member(s) (195), and/or releasable holding member connector(s) (200). Without being limited, the holding member mount point(s) (190) can also function as releasable holding member connector(s) (200).

In a first aspect, and referring to FIGS. 13,14, and 17, and without limitation, the downward facing fan(s) (90) can be connected to one or more of any suitable and effective pivot mechanism(s) (180), where the downward facing fan(s) (90) can be located vertically upward when not in use, and then lowered into any suitable and effective position(s) for operation of the downward facing fan(s) (90), preferably, and without limitation, where the airflow out of the downward facing fan(s) (90) is directed at the floor(s) (95) of the treated room(s) and/or targeted area(s) (30), and more preferably and without limitation, where the airflow out of the downward facing fan(s) (90) is directed straight down or about straight down at the floor(s) (95) of the treated room(s) and/or targeted area(s) (30), when the downward facing fan(s) (90) is operated. It is also preferred, without limitation, that the pivot mechanism(s) (180) is any suitable and effective upward bending hinge(s) (230), and the upward bending hinge(s) (230) when folded, moved, and/or extended downward, stops the downward movement of the downward facing fan(s) (90) when the outlet(s) (225) of the downward facing fan(s) (90) is horizontal and/or about horizontal with the the floor(s) (95) of the treated room(s) and/or targeted area(s) (30).

It is preferred, without limitation, that the one or more releasable position locking apparatus(s) (185) is suitably and effectively used in any manner known to those skilled in the art, to maintain the downward facing fan(s) (90) in any effective orientation(s) and/or angle(s), at any time(s), and more preferably, and without limitation, so that the downward facing fan(s) (90) are located and/or stored vertically upward when the downward facing fan(s) (90) are not being operated.

According to FIGS. 13, 14, and 17, and without limitation, the pivot mechanism(s) (180) can provide any effective range of articulation, movement, and/or mechanical motion, so the downward facing fan(s) (90) can be stored vertically upward and/or close to vertically upward, and where any effective means known to those skilled in the art can be used to removably secure the downward facing fan(s) (90) into this position(s) or orientation(s) at any suitable and effective time(s). It is preferred, without limitation, that the downward facing fan(s) (90) is directly and/or indirectly connected to one or more of any suitable and effective holding member mount point(s) (190) at any suitable and effective location(s), and the holding member mount point(s) (190) is suitably and effectively connected to one or more of any suitable and effective holding member(s) (195) in any suitable and effective manner known to those skilled in the art so that the holding member(s) (195) can effectively rotate, pivot, move, and/or turn, at any effective time(s) and/or when needed, and where the the one or more any suitable holding member(s) (195) is removably attached to one or more of any suitable and effective releasable holding member connector(s) (200), at any suitable and effective time(s), that is located at any suitable and effective location(s). The holding member connector(s) (200) can releasably connect to the one or more holding member(s) (195), at any suitable and effective time(s), all in a manner known to those skilled in the art.

Figure 15:
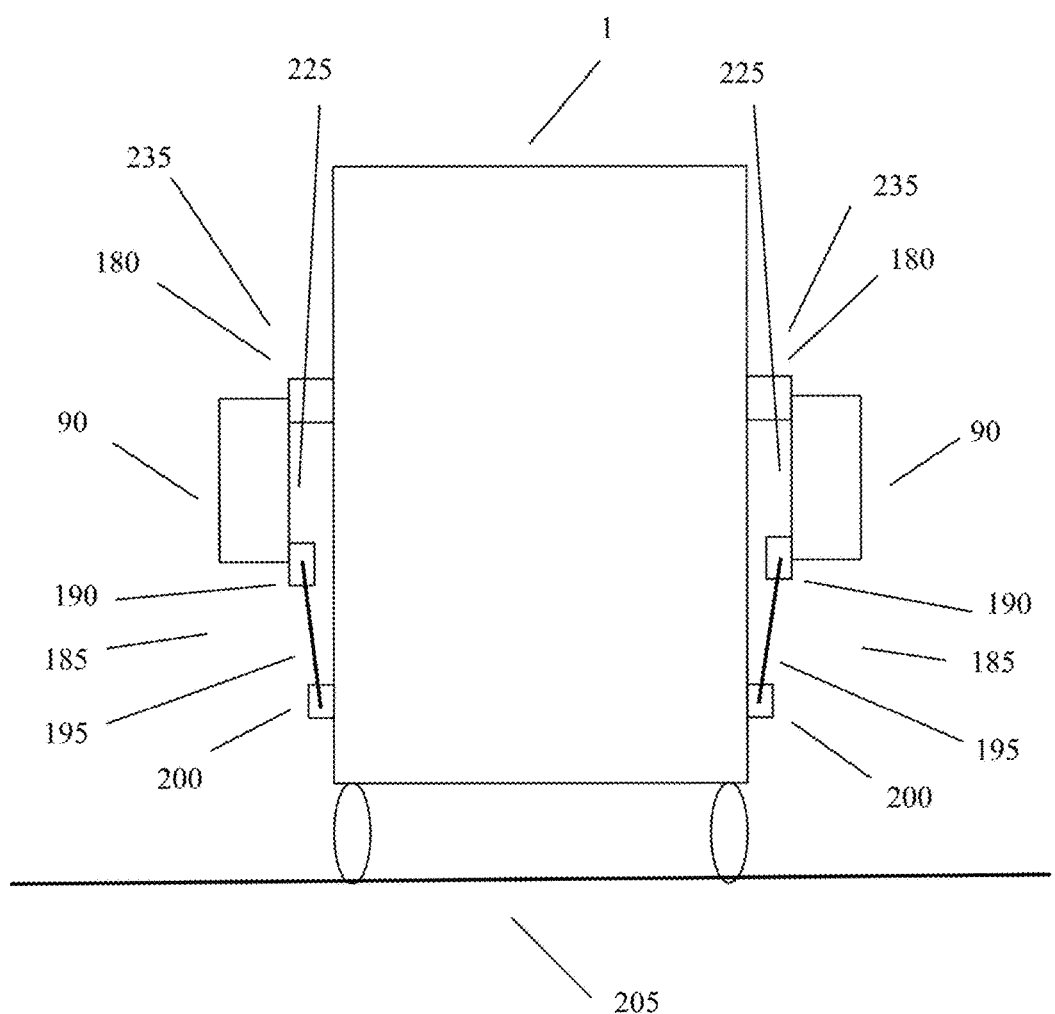
FIG. 15 is a front view of an ultrasonic aerosol generator with upward pivoting outboard fans in a stowed orientation.
Figure 16:
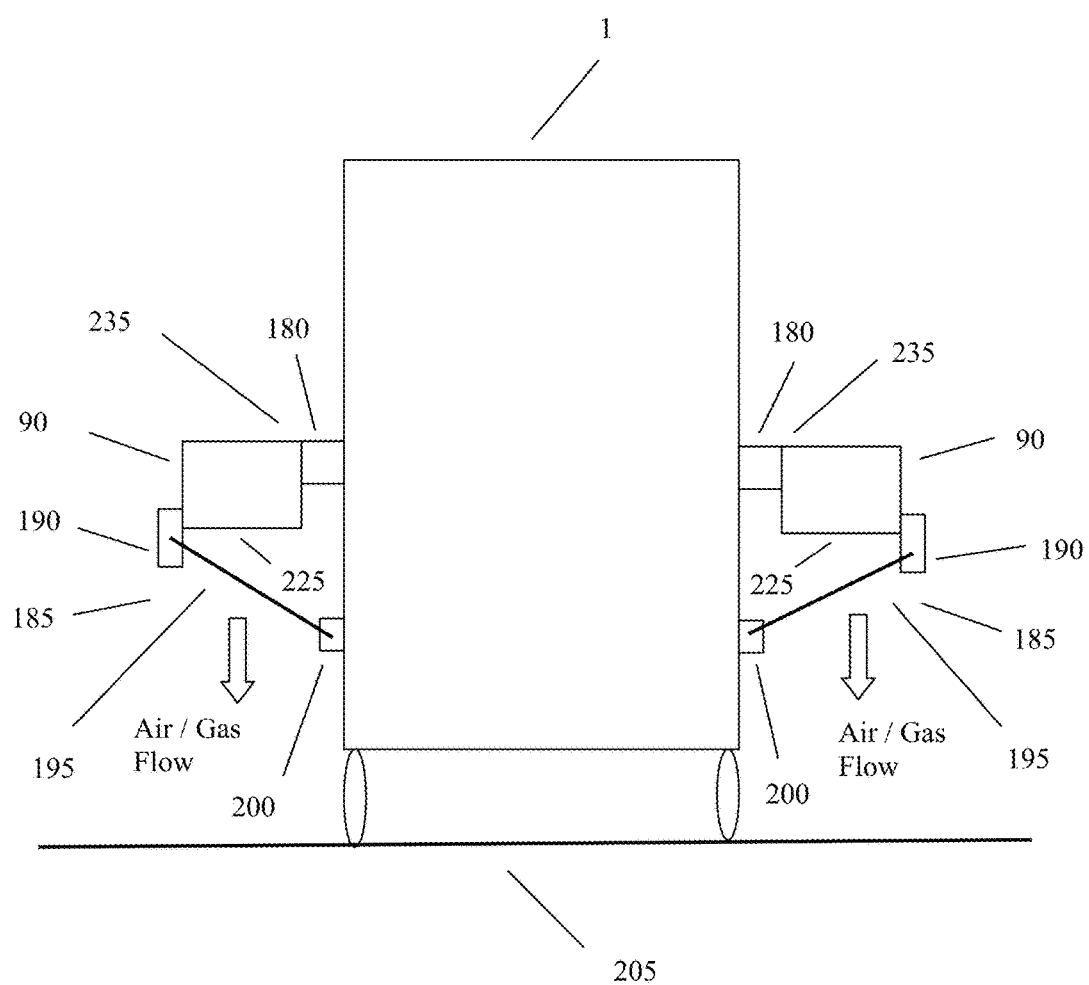
FIG. 16 is a front view of an ultrasonic aerosol generator with upward pivoting outboard fans in an activated orientation.
Figure 18:
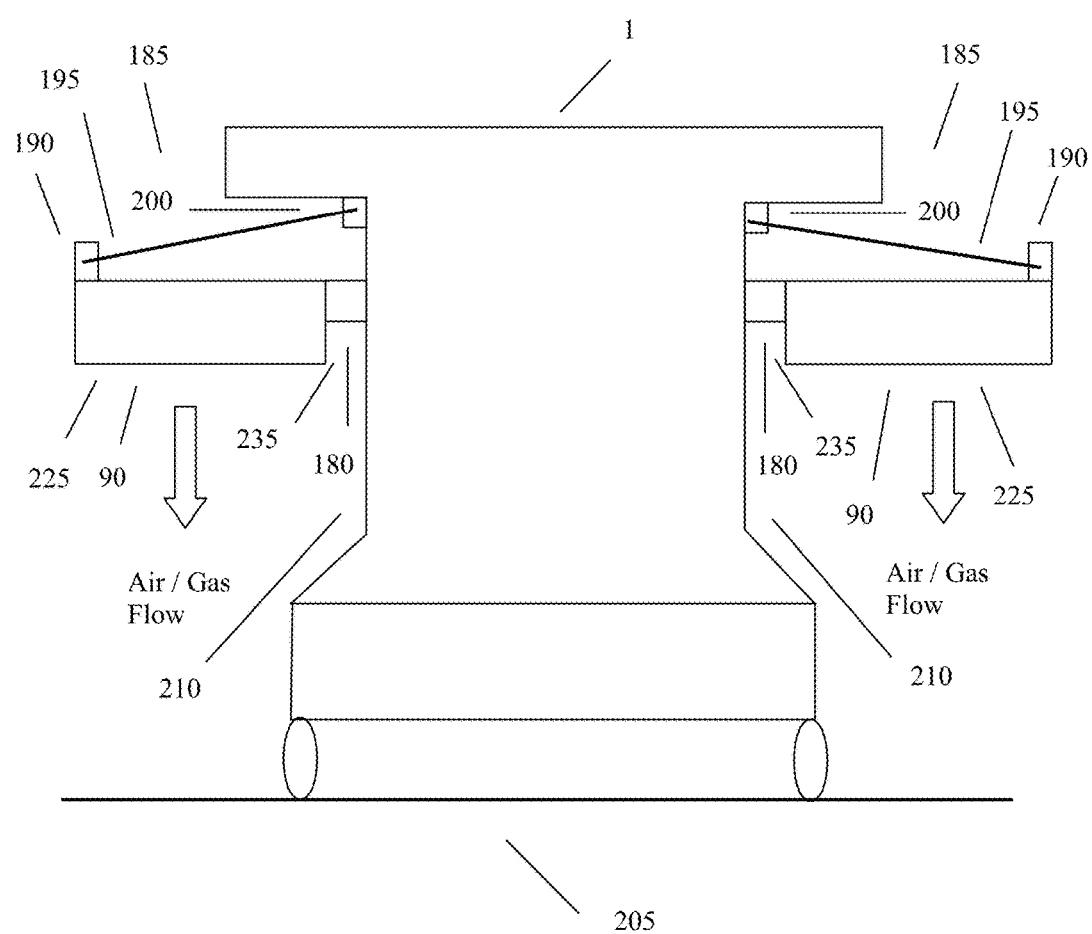
FIG. 18 is a front view of an ultrasonic aerosol generator with recessed downward pivoting outboard fans in an activated orientation.

In a second aspect, and referring to FIGS. 15, 16, and 18, and without limitation, the downward facing fan(s) (90) can be connected to one or more of any suitable and effective pivot mechanism(s) (180), where the downward facing fan(s) (90) can be located vertically downward when not in use, and then lifted, and/or supported, into any suitable and effective position(s) for operation of the downward facing fan(s) (90), preferably, and without limitation, where the airflow out of the downward facing fan(s) (90) is directed at the floor(s) (95) of the treated room(s) and/or targeted area(s) (30), and more preferably and without limitation, where the airflow out of the downward facing fan(s) (90) is directed straight down or about straight down at the floor(s) (95) of the treated room(s) and/or targeted area(s) (30), when the downward facing fan(s) (90) is operated. It is also preferred, without limitation, that the pivot mechanism(s) (180) is any suitable and effective downward bending hinge(s) (235), and the downward bending hinge(s) (235) when folded, moved, and/or extended upward, stops the upward movement of the downward facing fan(s) (90) when the outlet(s) (225) of the downward facing fan(s) (90) is horizontal and/or about horizontal with the the floor(s) (95) of the treated room(s) and/or targeted area(s) (30). The downward facing fan(s) (90) can be positioned, removably fixed into position, supported, and/or located, in one or more of any effective orientation(s) and/or angle(s), with any suitable and effective means known to those skilled in the art, at any time(s).

It is preferred, without limitation, that in this aspect, the one or more releasable position locking apparatus(s) (185) is suitably and effectively used in any manner known to those skilled in the art, to maintain the outlet(s) (225) of the downward facing fan(s) (90), in any effective orientation(s) and/or angle(s), and more preferably, and without limitation, so that the outlet(s) (225) of the downward facing fan(s) (90) is horizontal and/or about horizontal, with the floor(s) (95), when the downward facing fan(s) (90) are operated.

According to FIGS. 15, 16, and 18, and without limitation, the pivot mechanism(s) (180) can also provide any effective range of articulation, movement, and/or mechanical motion, so the downward facing fan(s) (90) can be stored vertically downward and/or close to vertically downward, and where any effective means known to those skilled in the art can be used to removably secure the downward facing fan(s) (90) into this position(s) or orientation(s) at any suitable and effective time(s). It is preferred, without limitation, that the downward facing fan(s) (90) is directly and/or indirectly connected to one or more of any suitable and effective holding member mount point(s) (190) at any suitable and effective location(s), and the holding member mount point(s) (190) is suitably and effectively connected to one or more of any suitable and effective holding member(s) (195) in any suitable and effective manner known to those skilled in the art so that the holding member(s) (195) can effectively rotate, pivot, move, and/or turn, at any effective time(s) and/or when needed, and where the the one or more holding member(s) (195) is removably attached to one or more of any suitable and effective releasable holding member connector(s) (200) that is located at any suitable and effective location(s). The holding member connector(s) (200) can releasably connect, at any suitable and effective time(s), to the one or more holding member(s) (195), all in a manner known to those skilled in the art. Without being limited, the downward facing fan(s) (90) can be effectively supported into any effective, location(s), position(s), and/or orientation(s), when the holding member(s) (195) is effectively interfaced with the holding member connector(s) (200).

Figure 17:
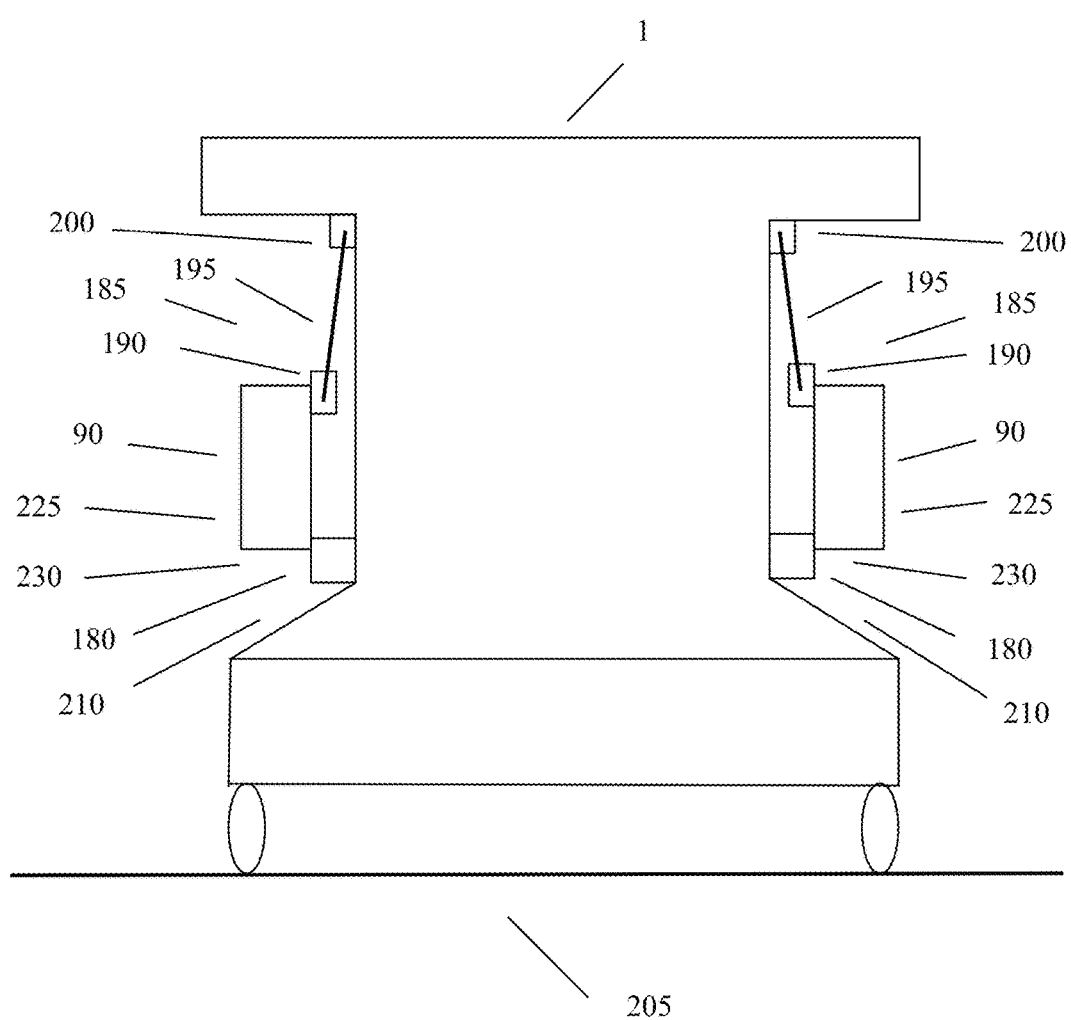
FIG. 17 is a front view of an ultrasonic aerosol generator with recessed downward pivoting outboard fans in a stowed orientation.

In a third aspect, and referring to FIGS. 17 and 18, and without limitation, the one or more downward facing fan(s) (90) can be located, positioned into, and/or stored in, one or more of any suitable and effective, indentations, impression(s), and/or space(s), (Herein called "Exterior Skin Indentation(s)") (210), formed in one or more of any side(s) of the aerosol generating apparatus(s) (01), when the downward facing fan(s) (90) are not being operated. Without being limited, the exterior skin indentation(s) (210) can be any, size(s), shape(s), depth(s), geometry(s), length(s), and/or width(s), that is preferably, and without limitation, at least suitable and effective. It is also preferred, without limitation that the exterior skin indentation(s) (210) are suitably and effectively located and positioned.

Without being limited, one or more of any part(s), surface(s), and/or area(s), of the exterior skin indentation(s) (210) and/or aerosol generating apparatus(s) (01), below the downward facing fan(s) (90), but preferably, and without limitation, at least any suitable and effective lower area(s) and/or surface(s) of the exterior skin indentation(s) (210), can also be slanted away from the aerosol generating apparatus(s) (01), at any suitable and effective angle(s) towards the floor(s) (95).

Figure 19:
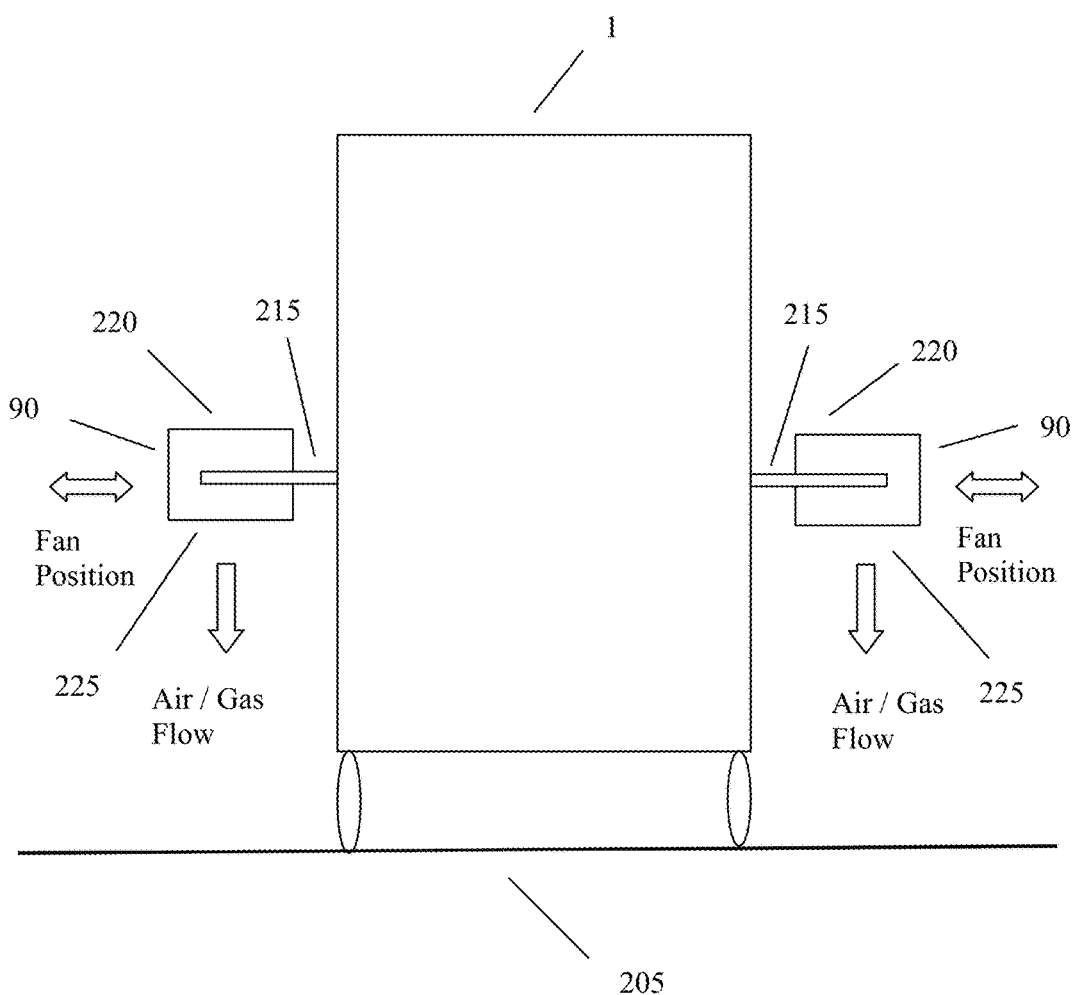
FIG. 19 is a front view of an ultrasonic aerosol generator with side pivoting outboard fans in an activated orientation.

In a fourth aspect, and referring to FIG. 19, and without limitation, the one or more of any suitable and effective downward facing fan(s) (90) can also be suitably stored within the aerosol generating apparatus(s) (01), and deployed outward from and/or outside of, the aerosol generating apparatus(s) (01), at any suitable and effective time(s). Without being limited, the downward facing fan(s) (90) can be extended outward from the aerosol generating apparatus(s) (01) to any suitable and effective distance(s) and/or location(s). It is preferred, without limitation, that the downward facing fan(s) (90) are deployed at least far enough outward so the downward facing fan(s) (90) can effectively operate. It is also preferred, without limitation, that when the downward facing fan(s) (90) are extended outside of the aerosol generating apparatus(s) (01), the outlet(s) (225) of the downward facing fan(s) (90) are orientated in any effective orientation(s) and/or angle(s), and it is more preferred, without limitation, that the outlet(s) (225) of the downward facing fan(s) (90) are oriented horizontally with or to the floor(s) (95) when the downward facing fan(s) (90) are operated, and the air/gas(s) that move out of the downward facing fan(s) (90) are directed towards the floor(s) (95). It is even more preferred, without limitation, that the air/gas(s) are directed straight down and/or about straight down from the downward facing fan(s) (90) towards the floor(s) (95) when the downward facing fan(s) (90) are operated.

Without being limited, the downward facing fan(s) (90) can be supported and/or deployed outward from the aerosol generating apparatus(s) (01) using, and/or being interfaced with, one or more of any suitable and effective, part(s), design(s), and/or means known in the art, such as, but not limited to any, rail(s), guide(s), movable shelve(s), movable support(s), pivot(s), side motion pivot(s), and/or track(s) (Herein called "Support Rail(s)") (215), that can preferably, and without limitation, suitably and effectively, extend and/or retract at any suitable and effective time(s). Without being limited, the support rail(s) (215) can be any suitable and effective design(s) known to those skilled in the art. It is preferred, without limitation, that the support rail(s) (215) can retractably extend with any suitable and effective design(s) and in any suitable and effective manner(s), known to those skilled in the art. Without being limited, the one or more downward facing fan(s) (90) can be suitably and effectively interfaced with the one or more of any suitable and effective support rail(s) (215), using one or more of any suitable and effective, part(s), design(s), and/or in any suitable and effective manner(s) known to those skilled in the art.

Also, and without being limited, the downward facing fan(s) (90) can be moved into one or more of any suitable and effective location(s) and/or position(s) either manually and/or automatically, using any suitable part(s) such as, but not limited to any, one or more of any support rail(s) (215), via any suitable and effective mechanical, motorized, and/or automated, means known to those skilled in the art, at any suitable and effective time(s). Without being limited, the downward facing fan(s) (90) can also be effectively, releasably locked, releasably maintained, and/or temporarily maintained, into any suitable and effective location(s) and/or position(s), at any suitable and effective time(s), and for any suitable and effective duration of time(s), all in a manner known to those skilled in the art.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A method of stratification removal and aerosol distribution inside an enclosure, comprising the steps of:
   deploying an aerosol into the enclosure for a period of time;
   measuring said period of time with a controller;
   providing at least one aerosol generating device for generating an aerosol inside the enclosure, said at least one aerosol generating device includes at least one air blowing device, said at least one air blowing device is located in the enclosure, said at least one air blowing device blowing said aerosol directly into the enclosure;
   providing at least one second air blowing device for blowing air downward directly into the enclosure during said period of time, wherein some of the air from said at least one second air blowing device is forced upward through contact with a floor of the enclosure toward a ceiling of the enclosure, upward traveling turbulent air from said at least one second air blowing device breaks-up at least one stratified layer in the enclosure to allow said deployed aerosol to fully homogenize an entire volume of the enclosure; and
   utilizing said controller to control a supply of electrical power to said at least one air blowing device and said at least one second air blowing device, for an effective amount of time to remove stratification and disperse the aerosol within said enclosure.

2. The method of stratification removal and aerosol distribution inside an enclosure of claim 1, further comprising the step of:
   providing each one of said at least one aerosol generating device with at least one ultrasonic transducer, at least one power amplifier, at least one transducer chamber and at least one outlet tube, said at least one ultrasonic transducer is powered by said at least one power amplifier, said at least one ultrasonic transducer is disposed in a bottom of said at least one transducer chamber, said at least one outlet tube is disposed adjacent to said at least one transducer chamber.

3. The method of stratification removal and aerosol distribution inside an enclosure of claim 2, further comprising the step of:
   operating said at least one ultrasonic transducer at a frequency between about 0.025 MHz to about 10 MHz and a voltage of between about 20 to about 300.

4. The method of stratification removal and aerosol distribution inside an enclosure of claim 1, further comprising the step of:
   retaining said at least one second air blowing device at a bottom of an intake compartment, said intake compartment is retained at a bottom of a cabinet of said aerosol generating device, said intake compartment is fed with air from inside the enclosure.

5. The method of stratification removal and aerosol distribution inside an enclosure of claim 4, further comprising the step of:
   drawing air from the enclosure through at least one activated carbon filter before input into said intake compartment.

6. The method of stratification removal and aerosol distribution inside an enclosure of claim 1, further comprising the step of:
   heating at least one activated carbon filter to remove moisture therefrom.

7. The method of stratification removal and aerosol distribution inside an enclosure of claim 5, further comprising the step of:
   dehumidifying air from the enclosure before inputting the air into said intake compartment.

8. The method of stratification removal and aerosol distribution inside an enclosure of claim 7, further comprising the step of:
   drawing air from the enclosure through at least one activated carbon filter, said at least one activated carbon filter is located in a cabinet of said aerosol generating device, an outlet of said at least one activated carbon filter is input into said intake compartment.

9. The method of stratification removal and aerosol distribution inside an enclosure of claim 1, further comprising the step of:
   applying a liquid to elements of a dehumidifier, said liquid being at least one of a sanitizer, a disinfectant, a high-level disinfectant and sterilant.

10. The method of stratification removal and aerosol distribution inside an enclosure of claim 1, further comprising the step of:
    retaining at least one second air blower device on at least one side of said aerosol generating device, said at least one second air blower blowing air downward.

11. The method of stratification removal and aerosol distribution inside an enclosure of claim 10, further comprising the step of:
    pivoting said at least one second air blower device from a vertical orientation to a horizontal orientation.

12. The method of stratification removal and aerosol distribution inside an enclosure of claim 1, further comprising the step of:
    recessing at least one side of said aerosol generating device to receive said at least one second air blower device.

13. The method of stratification removal and aerosol distribution inside an enclosure of claim 1, further comprising the step of:

pivoting at least one second air blower device in a horizontal plane from a side of said aerosol generating device.

14. A method of stratification removal and aerosol distribution inside an enclosure, comprising the steps of:
deploying an aerosol into the enclosure for a period of time;
measuring said period of time with a controller;
providing at least one aerosol generating device for generating an aerosol inside the enclosure, said at least one aerosol generating device includes at least one air blowing device, said at least one air blowing device blowing said aerosol directly into the enclosure;
providing at least one second air blowing device for blowing air downward directly into the enclosure during said period of time, said at least one second air blowing device is located in said at least one aerosol generating device, some of the air from said at least one second air blowing device is forced upward through contact with a floor of the enclosure toward a ceiling of the enclosure, upward traveling turbulent air from said at least one second air blowing device breaks-up at least one stratified layer in the enclosure to allow said deployed aerosol to fully homogenize an entire volume of the enclosure; and
utilizing said controller to control a supply of electrical power to said at least one air blowing device and said at least one second air blowing device for an effective amount of time to remove stratification and disperse the aerosol within said enclosure.

15. The method of stratification removal and aerosol distribution inside an enclosure of claim 14, further comprising the step of:
providing each one of said at least one aerosol generating device with at least one ultrasonic transducer, at least one power amplifier, at least one transducer chamber and at least one outlet tube, said at least one ultrasonic transducer is powered by said at least one power amplifier, said at least one ultrasonic transducer is disposed in a bottom of said at least one transducer chamber, said at least one outlet tube is disposed adjacent to said at least one transducer chamber.

16. The method of stratification removal and aerosol distribution inside an enclosure of claim 15, further comprising the step of:
operating said at least one ultrasonic transducer at a frequency between about 0.025 MHz to about 10 MHz and a voltage of between about 20 to about 300.

17. The method of stratification removal and aerosol distribution inside an enclosure of claim 14, further comprising the step of:
retaining said at least one second air blowing device at a bottom of an intake compartment, said intake compartment is retained at a bottom of a cabinet of said aerosol generating device, said intake compartment is fed with air from inside the enclosure.

18. The method of stratification removal and aerosol distribution inside an enclosure of claim 17, further comprising the step of:
drawing air from the enclosure through at least one activated carbon filter before input into said intake compartment.

19. The method of stratification removal and aerosol distribution inside an enclosure of claim 14, further comprising the step of:
heating at least one activated carbon filter to remove moisture therefrom.

20. The method of stratification removal and aerosol distribution inside an enclosure of claim 17, further comprising the step of:
dehumidifying air from the enclosure before inputting the air into said intake compartment.

21. The method of stratification removal and aerosol distribution inside an enclosure of claim 14, further comprising the step of:
applying a liquid to elements of a dehumidifier, said liquid being at least one of a sanitizer, a disinfectant, a high-level disinfectant and sterilant.

* * * * *